(12) United States Patent
Miyake et al.

(10) Patent No.: US 12,096,682 B2
(45) Date of Patent: Sep. 17, 2024

(54) ORGANIC ELECTROLUMINESCENCE DEVICE AND MONOAMINE COMPOUND FOR ORGANIC ELECTROLUMINESCENCE DEVICE

(71) Applicant: Samsung Display Co., Ltd., Yongin-Si (KR)

(72) Inventors: Hideo Miyake, Yokohama (JP); Masatsugu Ueno, Yokohama (JP); Xiulan Jin, Yokohama (JP); Ichinori Takada, Yokohama (JP); Hiroaki Itoi, Yokohama (JP); Takuya Uno, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 750 days.

(21) Appl. No.: 16/214,132

(22) Filed: Dec. 9, 2018

(65) Prior Publication Data

US 2019/0207117 A1    Jul. 4, 2019

(30) Foreign Application Priority Data

Jan. 4, 2018  (KR) .................. 10-2018-0001255

(51) Int. Cl.

| | |
|---|---|
| *H01L 51/00* | (2006.01) |
| *C07C 211/54* | (2006.01) |
| *C07C 211/60* | (2006.01) |
| *C07C 211/61* | (2006.01) |
| *C07D 307/91* | (2006.01) |
| *C07D 333/76* | (2006.01) |
| *C09B 57/00* | (2006.01) |
| *C09K 11/06* | (2006.01) |
| *H10K 85/60* | (2023.01) |
| *H10K 50/11* | (2023.01) |
| *H10K 50/15* | (2023.01) |
| *H10K 50/16* | (2023.01) |
| *H10K 50/17* | (2023.01) |
| *H10K 50/18* | (2023.01) |

(52) U.S. Cl.
CPC .......... *H10K 85/636* (2023.02); *C07C 211/54* (2013.01); *C07C 211/60* (2013.01); *C07C 211/61* (2013.01); *C07D 307/91* (2013.01); *C07D 333/76* (2013.01); *C09B 57/008* (2013.01); *C09K 11/06* (2013.01); *H10K 85/626* (2023.02); *H10K 85/631* (2023.02); *H10K 85/633* (2023.02); *H10K 85/6574* (2023.02); *C07C 2603/18* (2017.05); *C07C 2603/26* (2017.05); *C09K 2211/1007* (2013.01); *C09K 2211/1011* (2013.01); *C09K 2211/1014* (2013.01); *C09K 2211/1022* (2013.01); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02); *H10K 85/615* (2023.02)

(58) Field of Classification Search
None
See application file for complete search history.

(56) References Cited

U.S. PATENT DOCUMENTS

| | | | |
|---|---|---|---|
| 6,929,872 B2 | 8/2005 | Mori et al. | |
| 8,212,244 B2 | 7/2012 | Park et al. | |
| 8,686,406 B2 * | 4/2014 | Shin | C07C 255/58 428/917 |
| 9,065,060 B2 | 6/2015 | Hong et al. | |
| 9,799,833 B2 | 10/2017 | Mujica-Fernaud et al. | |
| 10,155,773 B2 | 12/2018 | Kim et al. | |
| 10,727,413 B2 | 7/2020 | Mujica-Fernaud et al. | |
| 2009/0230852 A1 | 9/2009 | Lee et al. | |
| 2013/0235552 A1* | 9/2013 | Nakazawa | F21V 9/14 362/19 |
| 2013/0334517 A1 | 12/2013 | Hong et al. | |
| 2016/0204352 A1* | 7/2016 | Adachi | C07D 219/02 544/102 |
| 2017/0018710 A1 | 1/2017 | Mujica-Fernaud et al. | |
| 2018/0105534 A1 | 4/2018 | Kim et al. | |

(Continued)

FOREIGN PATENT DOCUMENTS

| | | |
|---|---|---|
| CN | 101531565 | 9/2009 |
| CN | 103403125 | 11/2013 |

(Continued)

OTHER PUBLICATIONS

WO2016072690 machine translation from Google Patents downloaded Jan. 1, 2022.*

(Continued)

*Primary Examiner* — Alexander R Pagano
(74) *Attorney, Agent, or Firm* — Lewis Roca Rothgerber Christie LLP

(57) ABSTRACT

An organic electroluminescence device and a monoamine compound for an organic electroluminescence device are provided. The monoamine compound is represented by Formula 1. In Formula 1, FR is a phenanthryl group which is substituted with one phenyl group.

[Formula 1]

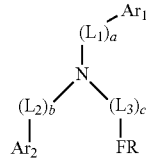

10 Claims, 2 Drawing Sheets

(56) References Cited

U.S. PATENT DOCUMENTS

| | | | |
|---|---|---|---|
| 2018/0114907 A1 | 4/2018 | Takada et al. | |
| 2021/0198214 A1 | 7/2021 | Mun et al. | |
| 2021/0355142 A1* | 11/2021 | Zhai | H10K 85/6572 |
| 2023/0212135 A1* | 7/2023 | Sakuma | H10K 85/631 257/40 |

FOREIGN PATENT DOCUMENTS

| | | | | |
|---|---|---|---|---|
| CN | 106132910 | | 11/2016 | |
| CN | 106866498 | | 6/2017 | |
| CN | 106893581 | | 6/2017 | |
| CN | 106986835 | | 7/2017 | |
| CN | 104364245 | | 10/2017 | |
| CN | 107880056 | | 4/2018 | |
| CN | 108084180 | | 5/2018 | |
| CN | 108084180 A | * | 5/2018 | |
| EP | 2100941 | | 9/2009 | |
| JP | 3915256 | | 5/2007 | |
| JP | 2009-029726 | | 2/2009 | |
| JP | 2009215333 | | 9/2009 | |
| JP | 2009227607 | | 10/2009 | |
| JP | 2009-267255 | | 11/2009 | |
| JP | 4377783 | | 12/2009 | |
| JP | 2015-529632 | | 10/2015 | |
| JP | 2017-513815 | | 6/2017 | |
| KR | 10-0817380 | | 3/2008 | |
| KR | 10-2010-0086672 | | 8/2010 | |
| KR | 20110047803 | | 5/2011 | |
| KR | 10-1072817 | | 10/2011 | |
| KR | 1072817 B1 | * | 10/2011 | C07D 209/82 |
| KR | 10-2012-0083245 | | 7/2012 | |
| KR | 10-1233379 | | 2/2013 | |
| KR | 20130133518 | | 12/2013 | |
| KR | 10-2014-0048021 | | 4/2014 | |
| KR | 20150102734 | | 9/2015 | |
| KR | 20160127864 | | 11/2016 | |
| KR | 20160143627 | | 12/2016 | |
| KR | 20160149879 | | 12/2016 | |
| KR | 10-1756611 | | 7/2017 | |
| KR | 10-1764907 | | 8/2017 | |
| WO | 2011/013959 | | 2/2011 | |
| WO | 2015131976 | | 9/2015 | |
| WO | WO2016072690 | * | 5/2016 | C09K 11/06 |
| WO | 2016175533 | | 11/2016 | |
| WO | 2017126818 | | 7/2017 | |
| WO | 2017204556 | | 11/2017 | |

OTHER PUBLICATIONS

CAS Abstract and Indexed Compound, H. Ji et al., KR 1072817 (2011) (Year: 2011).*
A European Search Report dated Apr. 17, 2019 issued in European Patent Application No. 18214542.5.
Korean Office Action dated Jan. 13, 2022, in Korean Patent Office for Korean Patent Application No. 10-2018-0001255.

* cited by examiner

ORGANIC ELECTROLUMINESCENCE DEVICE AND MONOAMINE COMPOUND FOR ORGANIC ELECTROLUMINESCENCE DEVICE

CROSS-REFERENCE TO RELATED APPLICATION

This application claims priority from and the benefit of Korean Patent Application No. 10-2018-0001255, filed on Jan. 4, 2018, which is hereby incorporated by reference for all purposes as if fully set forth herein.

BACKGROUND

Field

Exemplary embodiment/implementation of the invention relates to an organic electroluminescence device and a monoamine compound for an organic electroluminescence device.

Discussion of the Background

Researchers are actively pursuing the development of an organic electroluminescence display device as an image display device. Different from a liquid crystal display device, the organic electroluminescence display device is a self-luminescent display device in which holes and electrons injected from a first electrode and a second electrode recombine in an emission layer. A light emission material including an organic compound in the emission layer emits light to display an image.

However, an organic electroluminescence display device tends to have high driving voltage, low emission efficiency, and low lifespan when compared to other display devices. Thus, there is a need to develop a material that stably decreases the driving voltage, increases the emission efficiency, and increases the lifespan for an organic electroluminescence display device.

The above information disclosed in this Background section is only for understanding of the background of the inventive concepts, and, therefore, it may contain information that does not constitute prior art.

SUMMARY

Exemplary embodiments of the invention provide an organic electroluminescence device and a monoamine compound used as a material for a hole transport region of an organic electroluminescence device. Exemplary embodiments of the invention also provide that an organic electroluminescence device containing the monoamine compound used as a material for a hole transport region unexpectedly has a low (decreased) driving voltage, high (increased) emission efficiency and long (increased) lifespan compared with conventional organic electroluminescence devices.

Additional features of the inventive concepts will be set forth in the description which follows, and in part will be apparent from the description, or may be learned by practice of the inventive concepts.

An exemplary embodiment of the invention provides an organic electroluminescence device including a first electrode, a hole transport region disposed on the first electrode, an emission layer disposed on the hole transport region, an electron transport region disposed on the emission layer, and a second electrode provided on the electron transport region, wherein the hole transport region includes a monoamine compound represented by the following Formula 1:

[Formula 1]

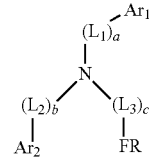

In Formula 1, $L_1$ to $L_3$ are each independently a direct linkage, a substituted or unsubstituted arylene group having 6 to 12 carbon atoms for forming a ring, or a substituted or unsubstituted heteroarylene group having 5 to 12 carbon atoms for forming a ring, "a" to "c" are each independently an integer of 0 to 2, $Ar_1$ and $Ar_2$ are each independently a substituted or unsubstituted aryl group having 6 to 30 carbon atoms for forming a ring, or a substituted or unsubstituted heteroaryl group having 5 to 12 carbon atoms for forming a ring, and FR is represented by one of the following Formulae 2-1 to 2-4:

[Formula 2-1]

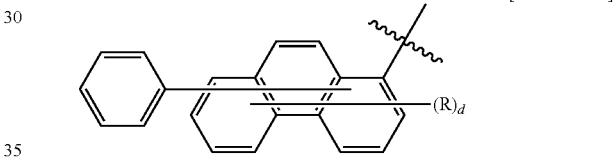

[Formula 2-2]

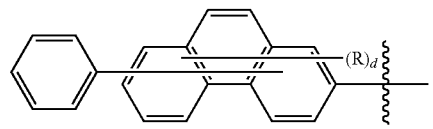

[Formula 2-3]

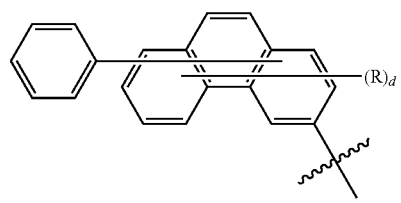

[Formula 2-4]

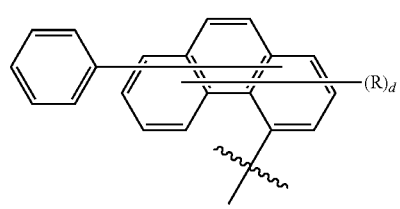

In Formulae 2-1 to 2-4, R is a hydrogen atom, a deuterium atom, a halogen atom, or a substituted or unsubstituted aryl group having 6 to 12 carbon atoms for forming a ring, and "d" is an integer of 0 to 6.

An exemplary embodiment of the invention provides the monoamine compound represented by the following Formula 1:

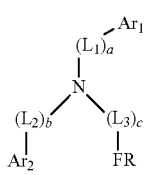

[Formula 1]

In Formula 1, $L_1$ to $L_3$ are each independently a direct linkage, a substituted or unsubstituted arylene group having 6 to 12 carbon atoms for forming a ring, or a substituted or unsubstituted heteroarylene group having 5 to 12 carbon atoms for forming a ring, "a" to "c" are each independently an integer of 0 to 2, $Ar_1$ and $Ar_2$ are each independently a substituted or unsubstituted aryl group having 6 to 30 carbon atoms for forming a ring, or a substituted or unsubstituted heteroaryl group having 5 to 12 carbon atoms for forming a ring, and FR is represented by one of the following Formulae 2-1 to 2-4:

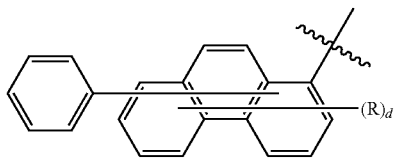

[Formula 2-1]

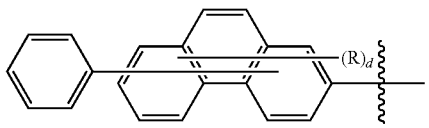

[Formula 2-2]

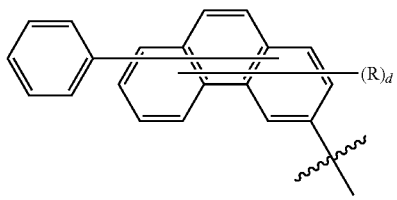

[Formula 2-3]

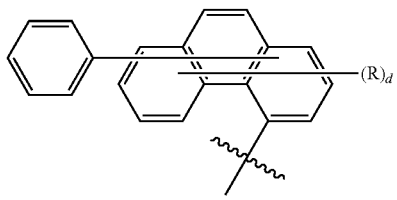

[Formula 2-4]

In Formulae 2-1 to 2-4, R is a hydrogen atom, a deuterium atom, a halogen atom, or a substituted or unsubstituted aryl group having 6 to 12 carbon atoms for forming a ring, and "d" is an integer of 0 to 6.

An exemplary embodiment of the invention provides a monoamine compound represented by the following Formula A:

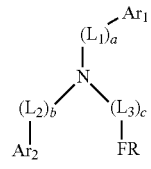

[Formula A]

In Formula A, $L_1$ to $L_3$ are each independently a direct linkage, a substituted or unsubstituted arylene group having 6 to 12 carbon atoms for forming a ring, or a substituted or unsubstituted heteroarylene group having 5 to 12 carbon atoms for forming a ring, "a" to "c" are each independently an integer of 0 to 2, $Ar_1$ and $Ar_2$ are each independently a substituted or unsubstituted aryl group having 6 to 30 carbon atoms for forming a ring, or a substituted or unsubstituted heteroaryl group having 5 to 12 carbon atoms for forming a ring, and FR is represented by the following Formula B:

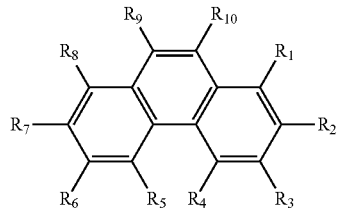

[Formula B]

In Formula B, at least one of $R_1$ to $R_4$ is a bonding part, the remainder of $R_1$ to $R_4$, and $R_5$ to $R_{10}$ are each independently a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 5 to 12 carbon atoms for forming a ring, and one of the remainder of $R_1$ to $R_4$, and $R_5$ to $R_{10}$ is a substituted or unsubstituted phenyl group.

It is to be understood that both the foregoing general description and the following detailed description are exemplary and explanatory and are intended to provide further explanation of the invention as claimed.

BRIEF DESCRIPTION OF THE FIGURES

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
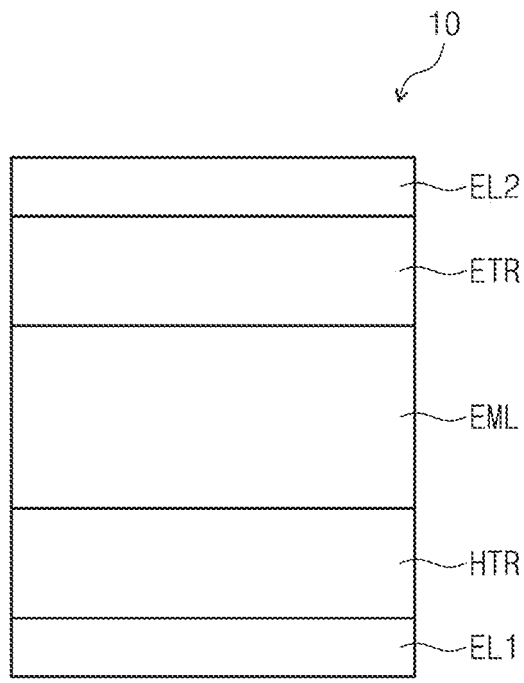
FIG. 1 is a cross-sectional view schematically illustrating an organic electroluminescence device according to an exemplary embodiment of the invention.

In the following description, for the purposes of explanation, numerous specific details are set forth in order to provide a thorough understanding of various exemplary embodiments of implementations of the invention. As used herein "embodiments" are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

In the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. For the purposes of this disclosure, "at least one of X, Y, and Z" "at least one selected from the group consisting of X, Y, and Z," and "at least one element selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items. However, the phrase "A, B, and C are each independently X, Y, or Z" may be construed as A is X only, Y only, or Z only, B is X only, Y only, or Z only, and C is X only, Y only, or Z only. In addition, the phrase "A is X, Y or Z" may be construed to mean A is X only, Y only, or Z only.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

First, organic electroluminescence devices according to exemplary embodiments of the invention will be explained referring to FIGS. 1, 2, and 3.

FIG. 1 is a cross-sectional view schematically illustrating an organic electroluminescence device according to an exemplary embodiment of the invention. FIG. 2 is a cross-sectional view schematically illustrating an organic electroluminescence device according to another exemplary embodiment of the invention. FIG. 3 is a cross-sectional view schematically illustrating an organic electroluminescence device according to a further exemplary embodiment of the invention.

Figure 2:
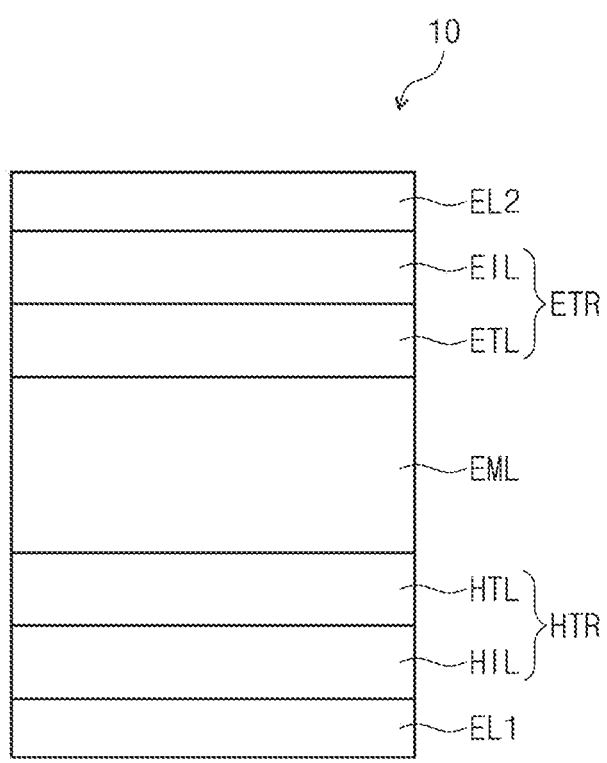
FIG. 2 is a cross-sectional view schematically illustrating an organic electroluminescence device according to an exemplary embodiment of the invention.
Figure 3:
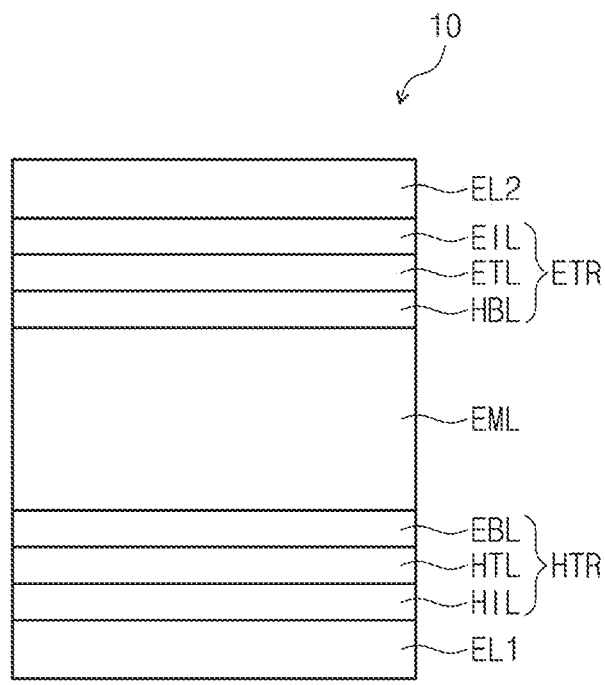
FIG. 3 is a cross-sectional view schematically illustrating an organic electroluminescence device according to an exemplary embodiment of the invention.

Referring to FIGS. 1, 2, and 3, an organic electroluminescence device 10 according to an exemplary embodiment of the invention includes a first electrode EL1, a hole transport region HTR, an emission layer EML, an electron transport region ETR, and a second electrode EL2.

The hole transport region HTR includes a monoamine compound according to an exemplary embodiment of the invention. Hereinafter, the monoamine compound according to an exemplary embodiment of the invention will be explained in detail and then, each layer of the organic electroluminescence device 10 will be explained.

The monoamine compound according to an exemplary embodiment of the invention is represented by the following Formula 1:

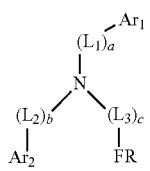

[Formula 1]

In Formula 1, $L_1$ to $L_3$ are each independently a direct linkage, a substituted or unsubstituted arylene group having 6 to 12 carbon atoms for forming a ring, or a substituted or unsubstituted heteroarylene group having 5 to 12 carbon atoms for forming a ring, "a" to "c" are each independently an integer of 0 to 2, $Ar_1$ and $Ar_2$ are each independently a substituted or unsubstituted aryl group having 6 to 30 carbon atoms for forming a ring, or a substituted or unsubstituted heteroaryl group having 5 to 12 carbon atoms for forming a ring.

In Formula 1, FR is represented by one of the following Formulae 2-1 to 2-4:

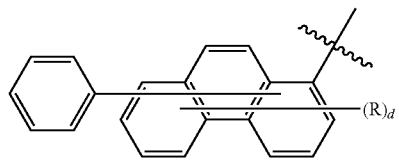

[Formula 2-1]

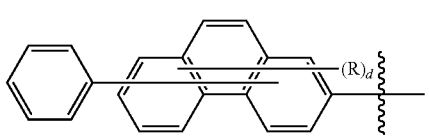

[Formula 2-2]

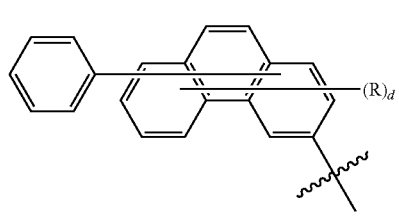

[Formula 2-3]

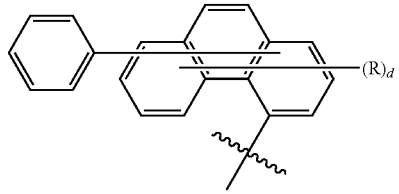

[Formula 2-4]

In each of Formulae 2-1 to 2-4, R is a hydrogen atom, a deuterium atom, a halogen atom, or a substituted or unsubstituted aryl group having 6 to 12 carbon atoms for forming a ring, and "d" is an integer of 0 to 6. In other words, in each of Formulae 2-1 to 2-4, a phenanthryl group may be substituted with up to six substituents other than a phenyl group. "d" may be, for example, 0, and in this case, FR is a phenanthryl group which is substituted with one phenyl group.

In the description,

means a part to be connected.

In the description, "substituted" means substituted with at least one substituent selected from the group consisting of a deuterium atom, a halogen group, a cyano group, a nitro group, a silyl group, a boron group, a phosphine group, an alkyl group, an alkenyl group, an aryl group, and a heterocycle. In addition, each of the substituents illustrated above may be substituted or unsubstituted. For example, a biphenyl group may be interpreted as an aryl group or a phenyl group substituted with a phenyl group.

In the description, examples of the halogen atom may include a fluorine atom, a chlorine atom, a bromine atom and an iodine atom.

In the description, the alkyl group may be a linear, branched or cyclic type. The carbon number of the alkyl group may be from 1 to 30, from 1 to 20, from 1 to 10, or from 1 to 4. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, c-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the aryl group means an optional functional group or substituent derived from an aromatic hydrocarbon ring. The aryl group may be a monocyclic aryl or a polycyclic aryl. The carbon number for forming a ring in the aryl group may be from 6 to 30, from 6 to 20, or from 6 to 12. Examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc., without limitation.

In the description, the fluorenyl group may be substituted, and two substituents may be combined with each other to form a spiro structure. Examples of the substituted fluorenyl group are shown below. However, an exemplary embodiment of the invention is not limited thereto.

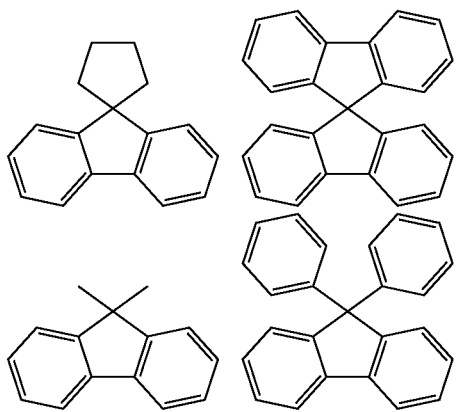

In the description, the heteroaryl group may be a heteroaryl including at least one of O, N, P, Si or S as a heteroatom. If the heteroaryl group includes two heteroatoms, two heteroatoms may be the same or different. The carbon number for forming a ring of the heteroaryl group may be 2 to 30, or 5 to 12. The heteroaryl group may be monocyclic heteroaryl or polycyclic heteroaryl. Examples of the polycyclic heteroaryl may have a dicyclic or tricyclic structure. Examples of the heteroaryl may include thiophene, furan, pyrrole, imidazole, thiazole, oxazole, oxadiazole, triazole, pyridine, bipyridine, pyrimidine, triazine, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, thiadiazole, phenothiazine, dibenzosilole, dibenzofuran, etc., without limitation.

In the description, the silyl group includes an alkyl silyl and an aryl silyl. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc. However, an exemplary embodiment of the invention is not limited thereto.

In the description, the boron group includes an alkyl boron group and an aryl boron group. Examples of the boron group include trimethylboron group, triethylboron group, t-butyldimethylboron group, triphenylboron group, diphenylboron group, phenylboron group, etc., without limitation.

In the description, the alkenyl group may be a linear chain or a branched chain. The carbon number is not specifically limited and may be 2 to 30, 2 to 20, or 2 to 10. Examples of the alkenyl group include vinyl, 1-butenyl, 1-pentenyl, 1,3-butadienyl aryl, styrenyl, styrylvinyl, etc., without limitation.

In the description, the explanation on the aryl group is applied to the arylene group except that the arylene group is a divalent group.

In the description, the explanation on the heteroaryl group is applied to the heteroarylene group except that the heteroarylene group is a divalent group.

First, the monoamine compound according to an exemplary embodiment of the invention will be explained.

In the description, "direct linkage" may include a single bond.

A phenanthryl group represented by Formulae 2-1 to 2-4 includes one phenyl group. In each of Formulae 2-1 to 2-4, R may not be a phenyl group.

In the description, the numbering of a phenanthryl group is as follows.

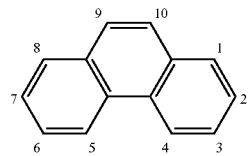

In Formula 1, if "a" is 1, $L_1$ may not be a direct linkage, if "b" is 1, $L_2$ may not be a direct linkage, and if "c" is 1, $L_3$ may not be a direct linkage.

In Formula 1, if "a" is 2, two $L_1$ groups are the same or different, if "b" is 2, two $L_2$ groups are the same or different, and if "c" is 2, two $L_3$ groups are the same or different. FR may be, for example, represented by the following Formula 2-1-1:

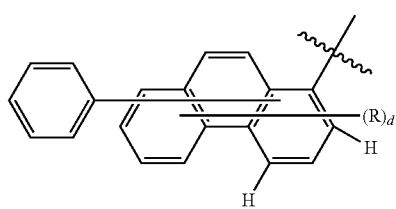

[Formula 2-1-1]

In Formula 2-1-1, R and "d" are the same as defined in Formula 2-1.

FR may be, for example, represented by the following Formula 2-2-1:

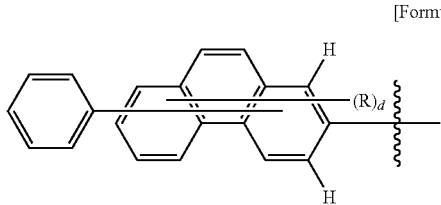

[Formula 2-2-1]

In Formula 2-2-1, R and "d" are the same as defined in Formula 2-2.

FR may be, for example, represented by the following Formula 2-3-1:

[Formula 2-3-1]

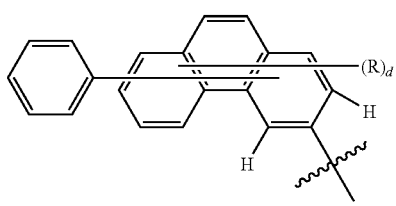

In Formula 2-3-1, R and "d" are the same as defined in Formula 2-3.

FR may be, for example, represented by the following Formula 2-4-1:

[Formula 2-4-1]

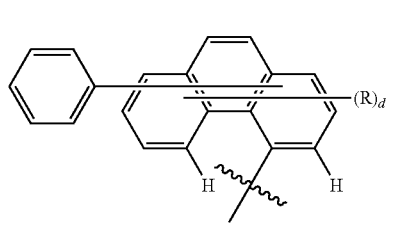

In Formula 2-4-1, R and "d" are the same as defined in Formula 2-4.

FR is preferably represented by Formula 2-2 or 2-3. For example, FR is preferably represented by Formula 2-2-1 or 2-3-1. However, an exemplary embodiment of the invention is not limited thereto, and FR may be represented by Formula 2-1 above.

FR may be, for example, represented by one of the following Formulae 3-1 to 3-3:

[Formula 3-1]

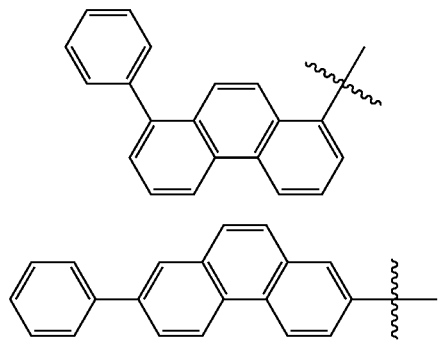

[Formula 3-2]

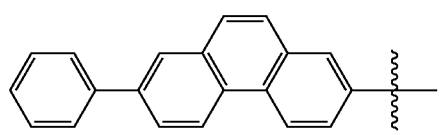

[Formula 3-3]

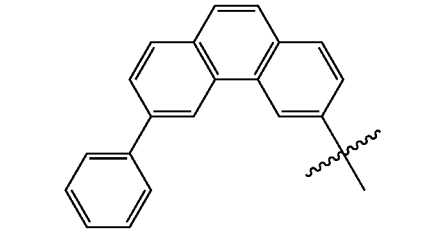

In Formula 1, "c" may be 1. That is, in Formula 1, FR may not make a direct linage with a nitrogen atom but may be bonded via $L_3$. For example, "c" may be 1, and $L_3$ may be a substituted or unsubstituted phenylene group or a substituted or unsubstituted naphthylene group. For example, "c" may be 1, and $L_3$ may be an unsubstituted phenylene group. For example, "c" may be 1, and $L_3$ may be an unsubstituted naphthylene group.

In Formula 1, $Ar_1$ and $Ar_2$ may be each independently a substituted or unsubstituted phenyl group, a substituted or unsubstituted biphenyl group, a substituted or unsubstituted fluorenyl group, a substituted or unsubstituted naphthyl group, a substituted or unsubstituted dibenzofuran group, or a substituted or unsubstituted dibenzothiophene group.

In Formula 1, $-(L_1)_a$-$Ar_1$ may include at least two benzene rings. Here, the benzene ring may be present in a monocyclic type, or may be included in a polycycle. For example, the benzene ring may include a benzene ring included in dibenzothiophene, naphthyl, dibenzofuran, etc., and may include at least two benzene rings.

In Formula 1, $-(L_1)_a$-$Ar_1$ may be represented by one of the structures below.

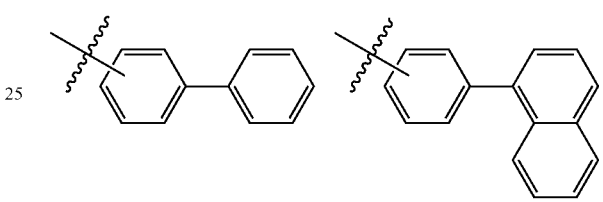

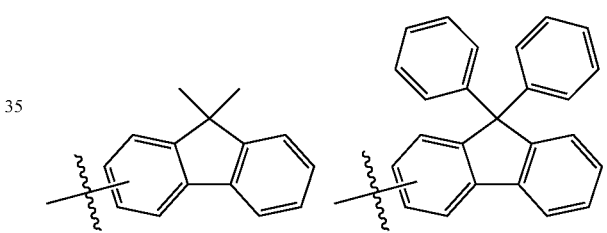

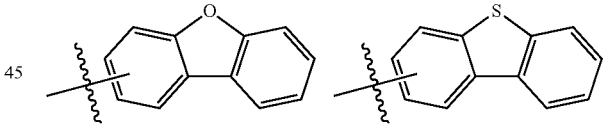

In Formula 1, $-(L_2)_a$-$Ar_1$ may include at least two benzene rings. Here, the benzene ring may be present in a monocyclic type, or may be included in a polycycle. For example, the benzene ring may include a benzene ring included in dibenzothiophene, naphthyl, dibenzofuran, etc., and may include at least two benzene rings.

In Formula 1, $-(L_2)_a$-$Ar_1$ may be represented by one of the structures below.

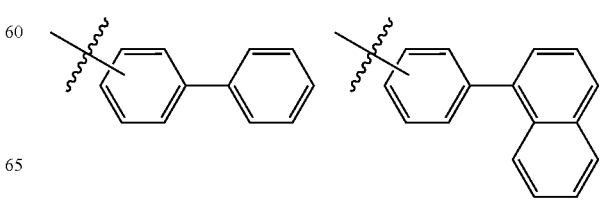

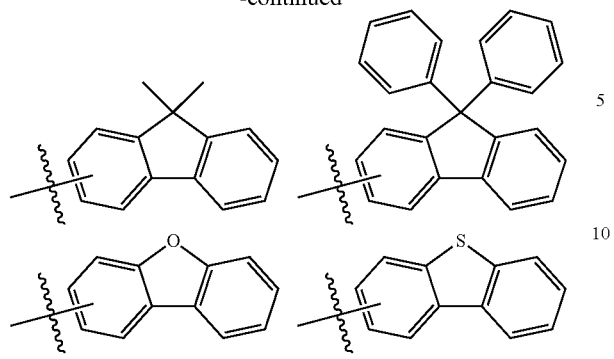

In Formula 1, at least one of $-(L_1)_a-Ar_1$ or $-(L_2)_b-Ar_2$ may include two or more benzene rings.

In Formula 1, at least one of $Ar_1$ or $Ar_2$ may be a substituted or unsubstituted heteroaryl group having 5 to 12 carbon atoms for forming a ring. In Formula 1, at least one of $Ar_1$ or $Ar_2$ may be a substituted or unsubstituted dibenzofuran group, or a substituted or unsubstituted dibenzothiophene group.

In Formula 1, "a" may be 0, and $Ar_1$ may be a substituted or unsubstituted heteroaryl group having 5 to 12 carbon atoms for forming a ring.

In Formula 1, "b" may be 0, and $Ar_2$ may be a substituted or unsubstituted heteroaryl group having 5 to 12 carbon atoms for forming a ring.

In Formula 1, at least one of $Ar_1$ or $Ar_2$ may be a substituted or unsubstituted aryl group having 10 to 30 carbon atoms for forming a ring, or a substituted or unsubstituted heteroaryl group having 10 to 12 carbon atoms for forming a ring.

In Formula 1, at least one of $Ar_1$ or $Ar_2$ may be a substituted or unsubstituted naphthyl group, a substituted or unsubstituted fluorenyl group, a substituted or unsubstituted dibenzofuran group, or a substituted or unsubstituted dibenzothiophene group.

The monoamine compound represented by Formula 1 according to an exemplary embodiment of the invention may be any one selected from the compounds represented in Compound Group 1 below. However, an exemplary embodiment of the invention is not limited thereto.

[Compound Group 1]

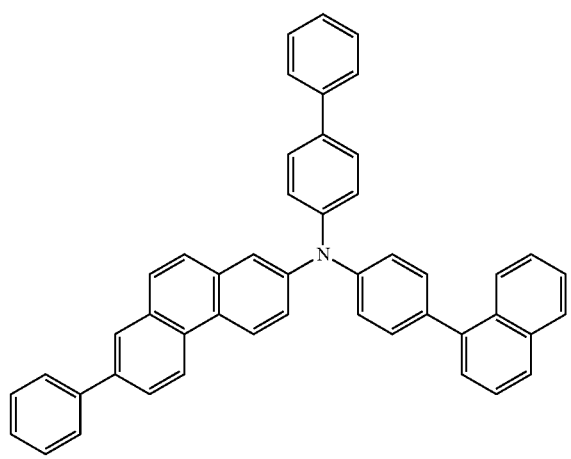

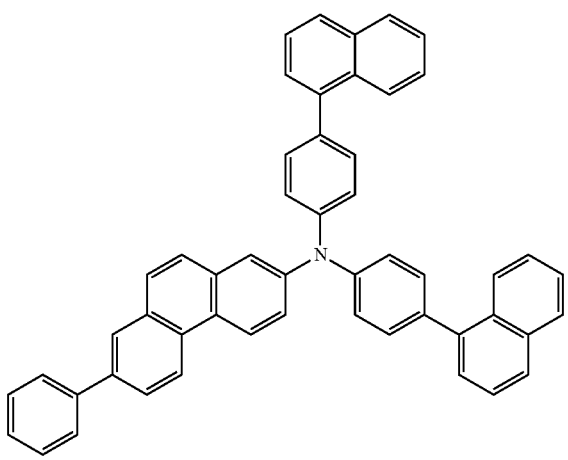

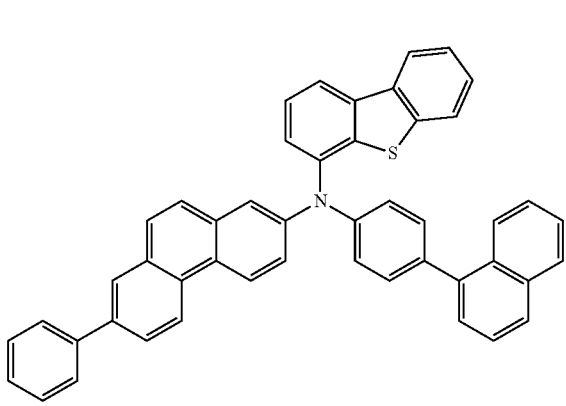

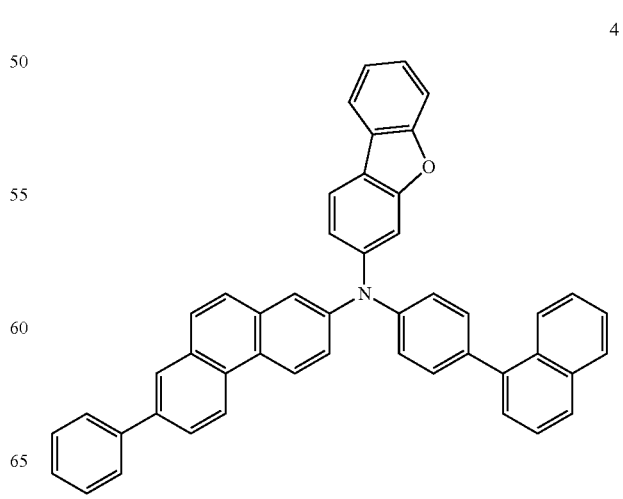

-continued
5
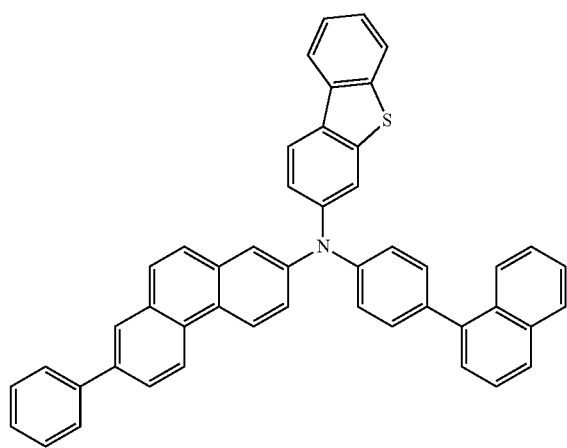
6
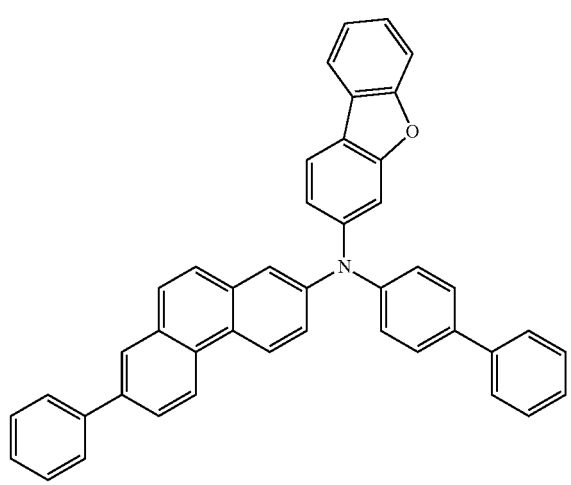
7
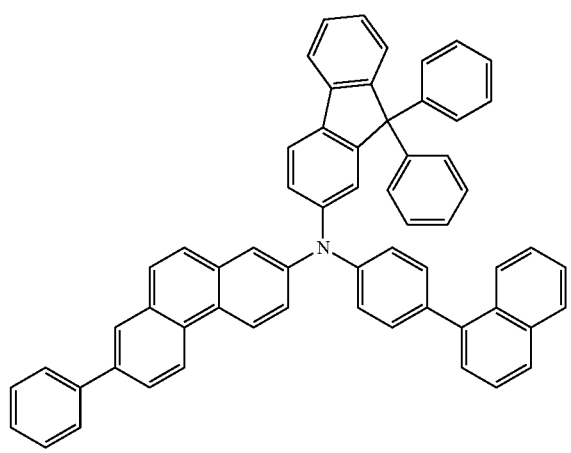
-continued
8
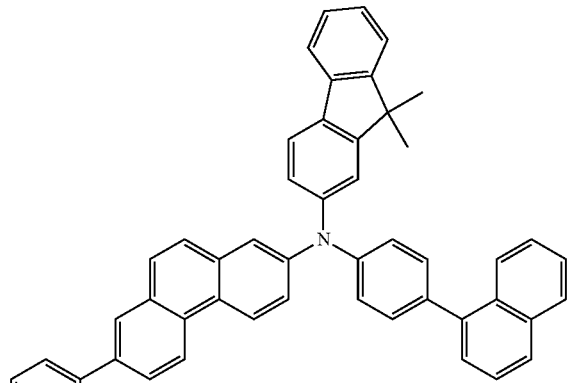
9
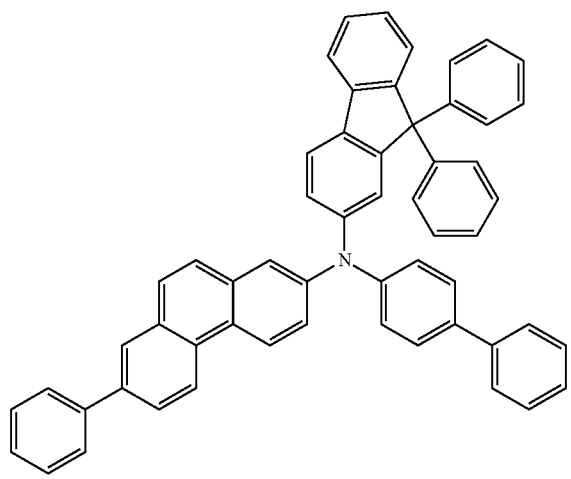
10
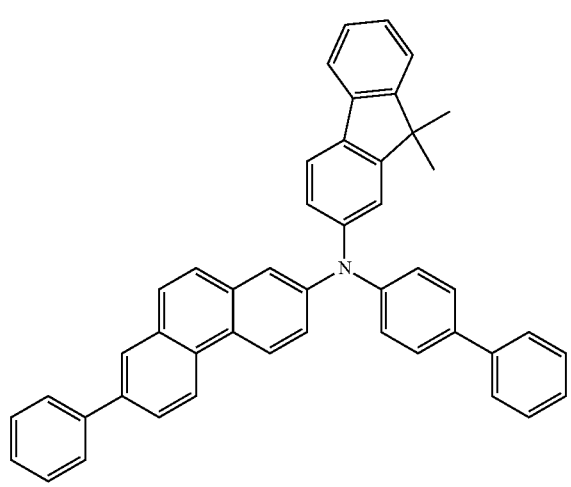

11
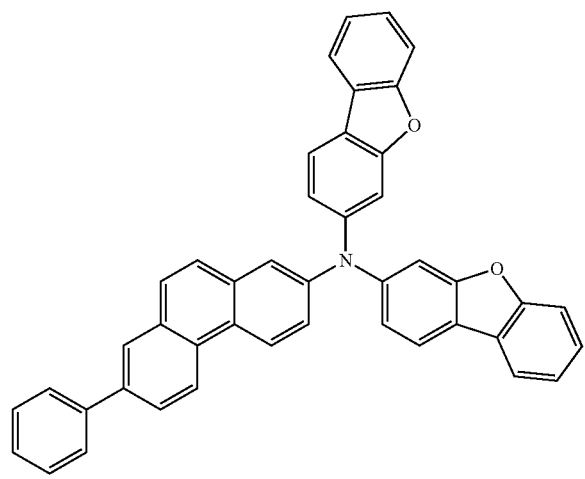
12
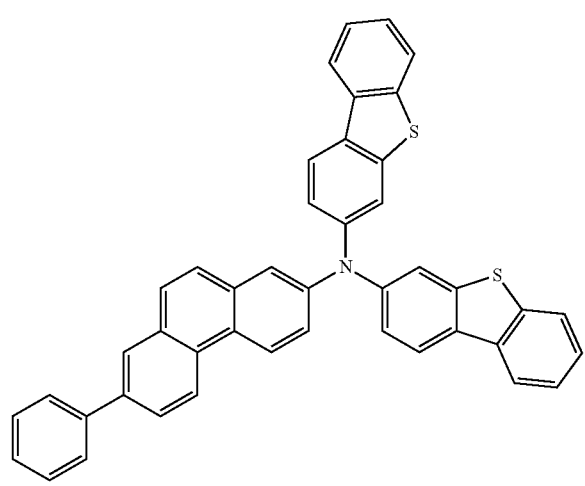
13
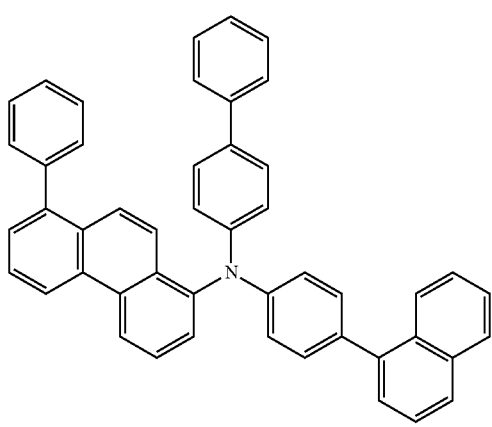
14
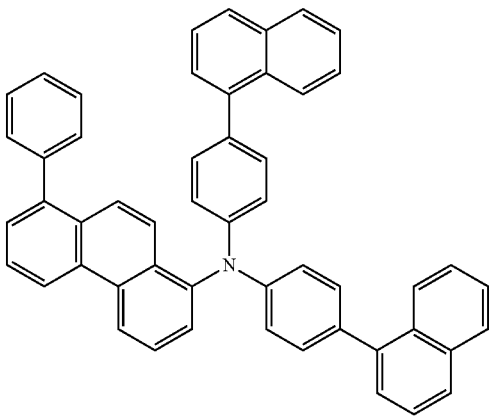
15
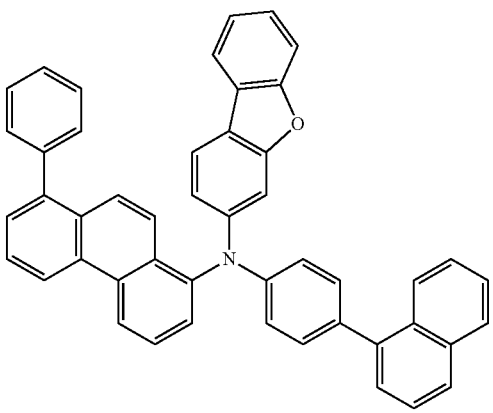
16
17

18
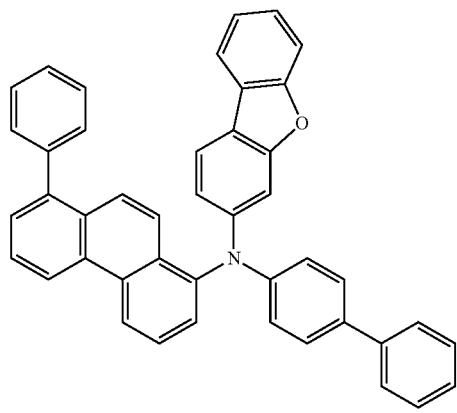
19
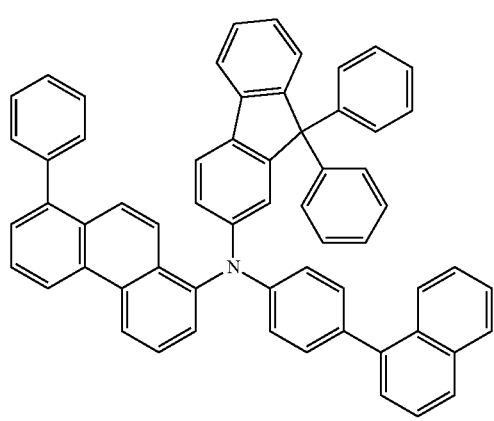
20
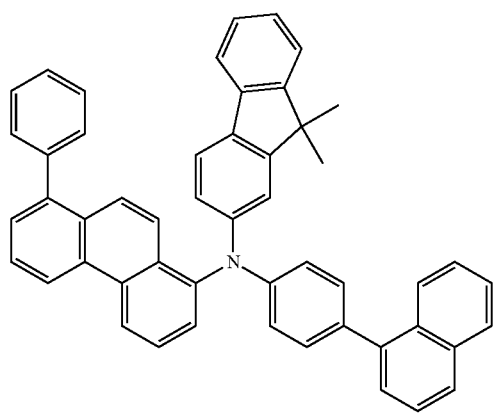
21
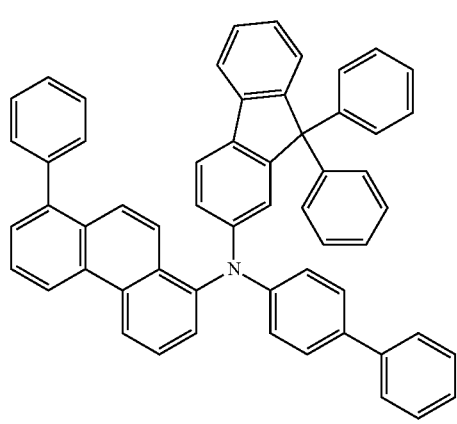
22
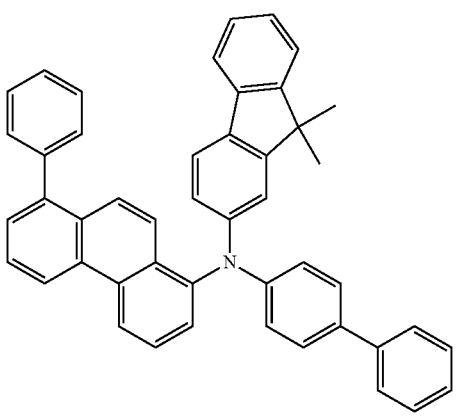
23
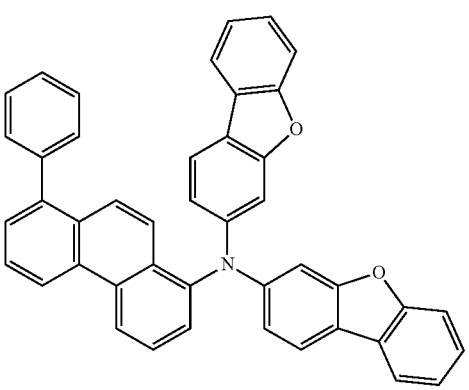
24
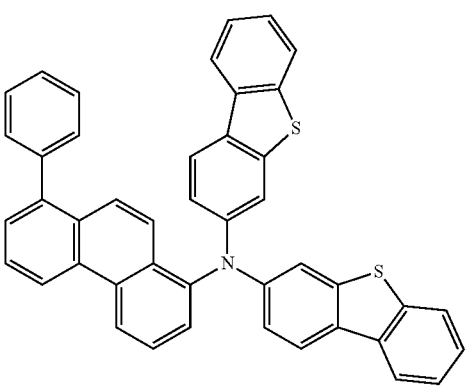
25
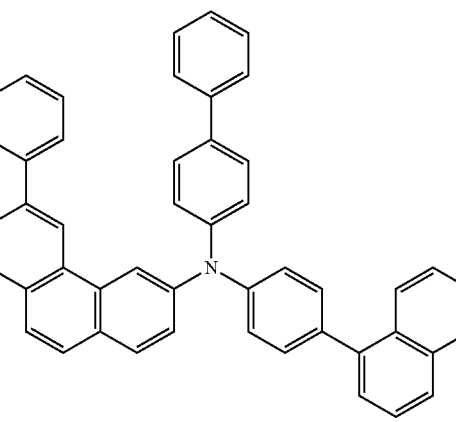

26
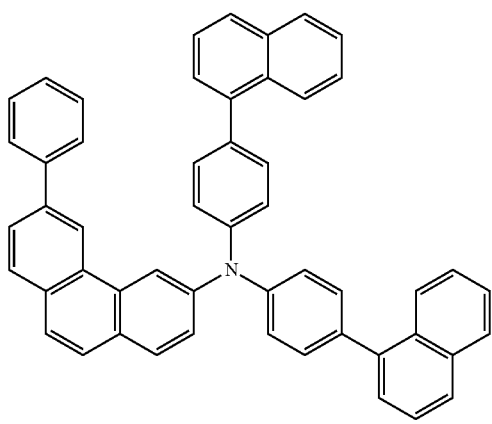
30
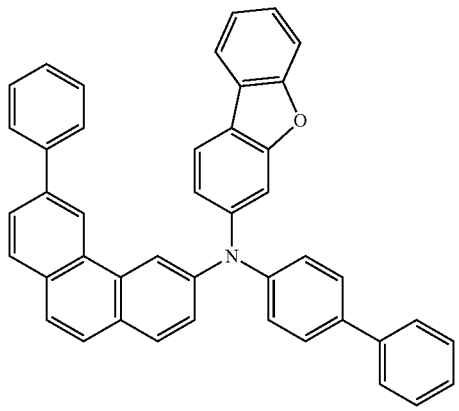
27
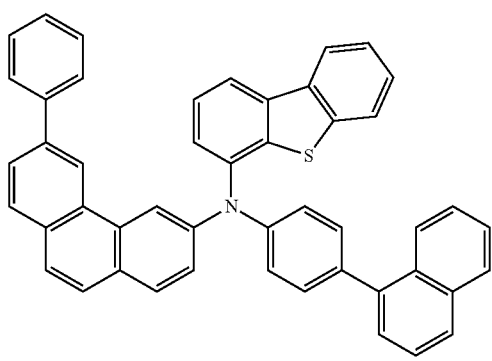
31
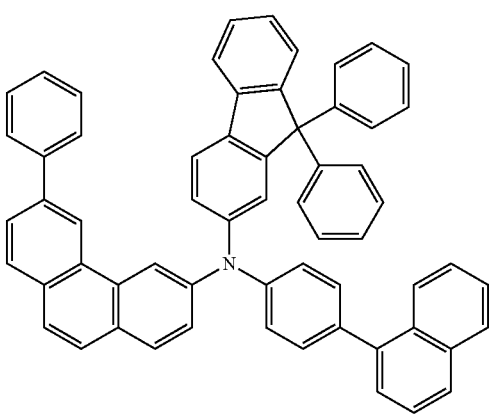
28
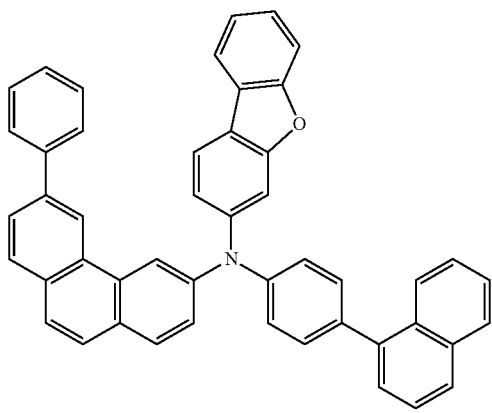
32
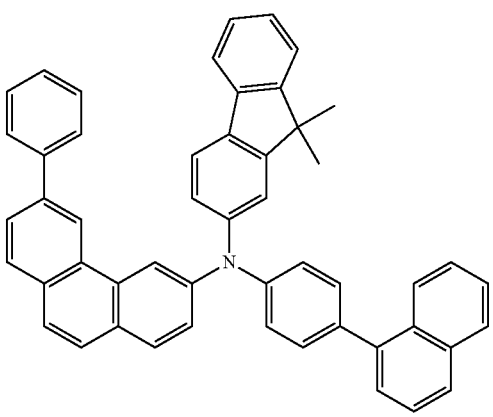
29
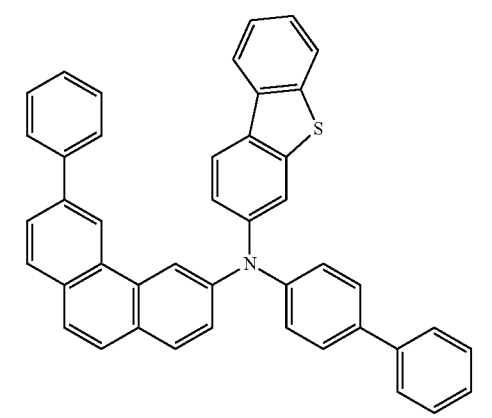
33
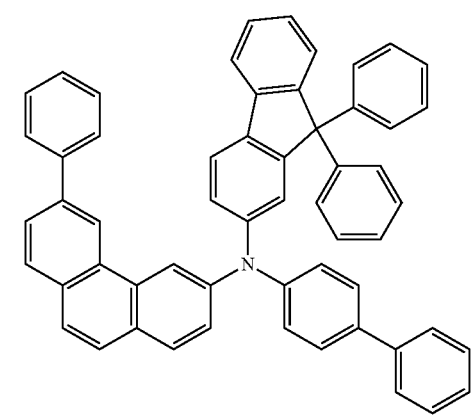

[Compound Group 2]
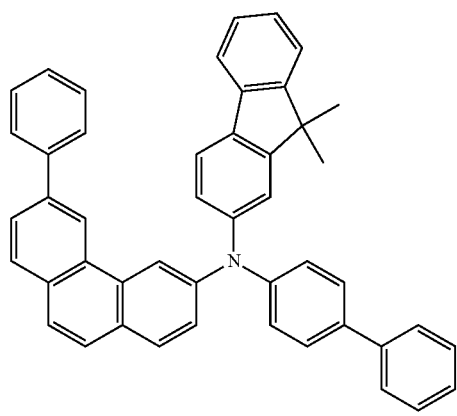
34
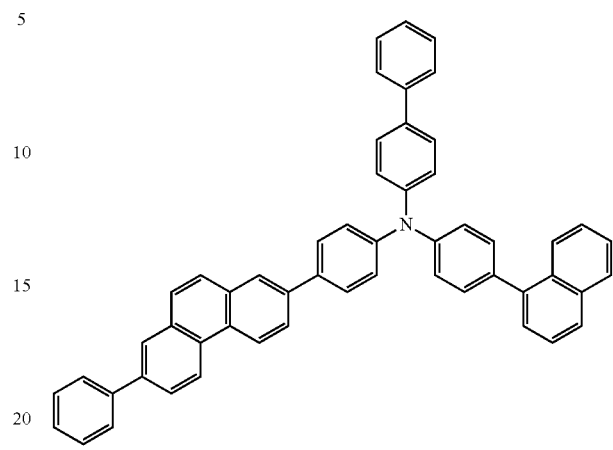
37
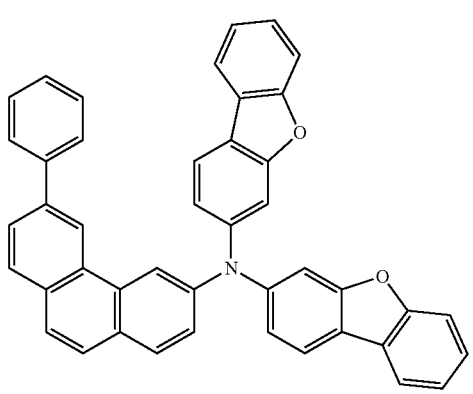
35
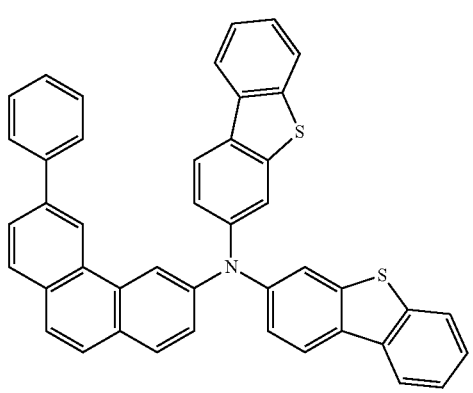
36
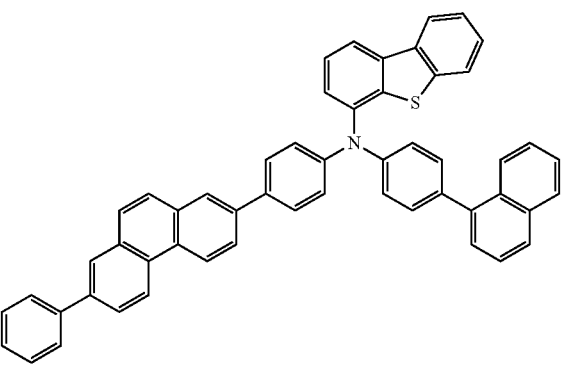
38
39
The monoamine compound represented by Formula 1 according to an exemplary embodiment of the invention may be any one selected from the compounds represented in Compound Group 2 below. However, an exemplary embodiment of the invention is not limited thereto.

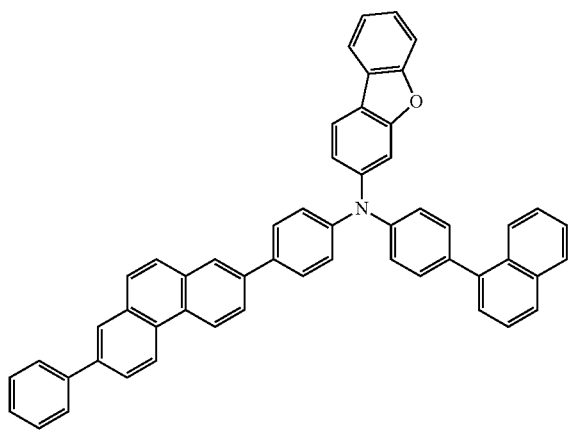
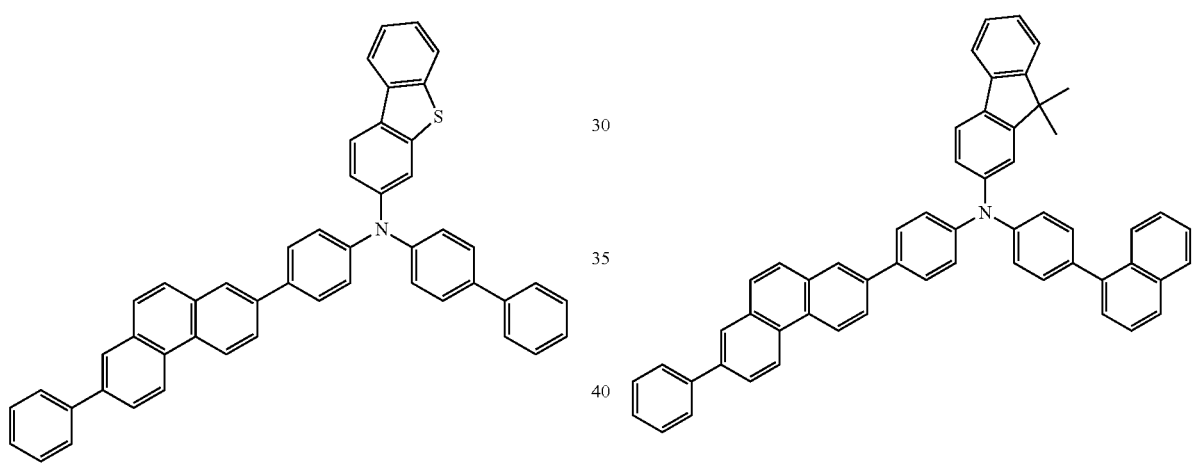
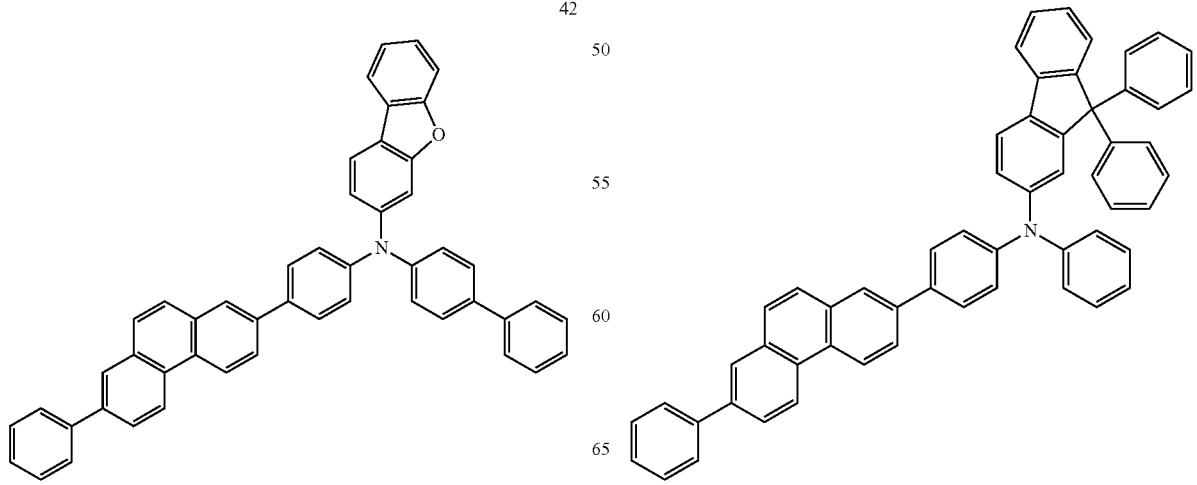

46
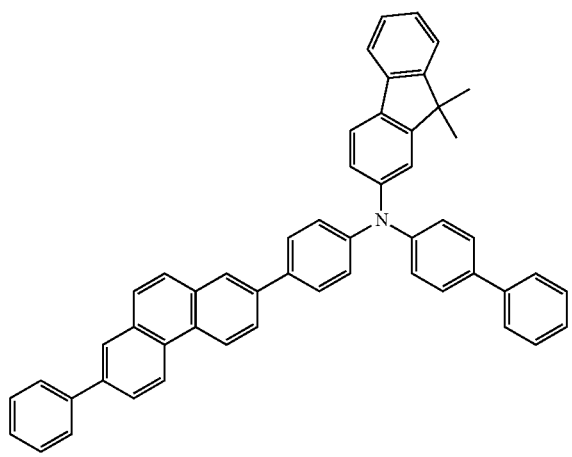
47
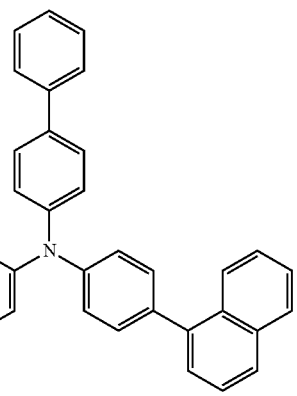
48
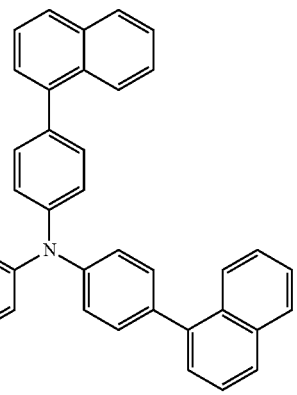
49
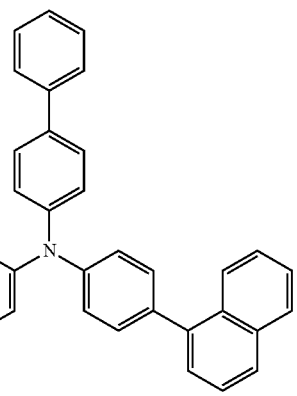
50
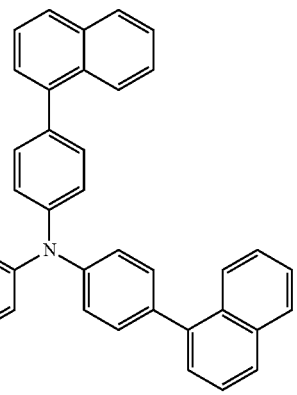
51
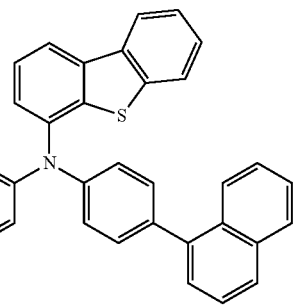
52
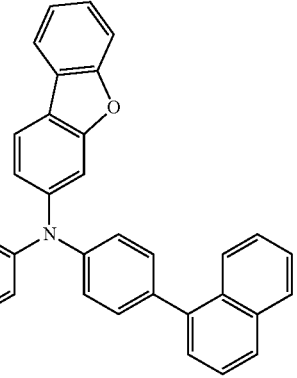

53
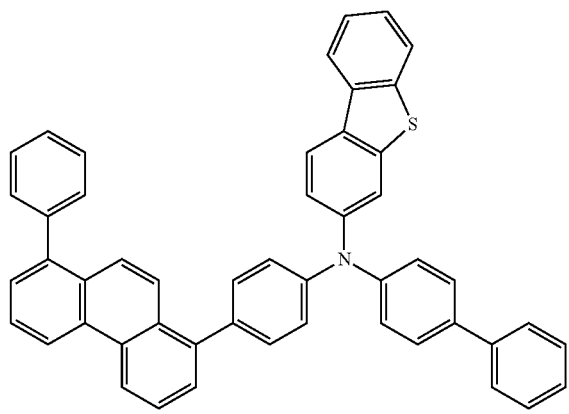
54
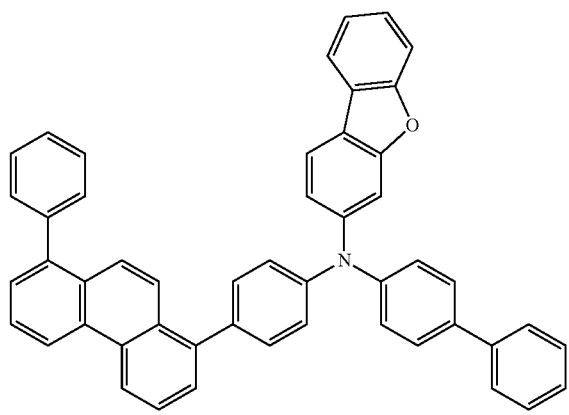
55
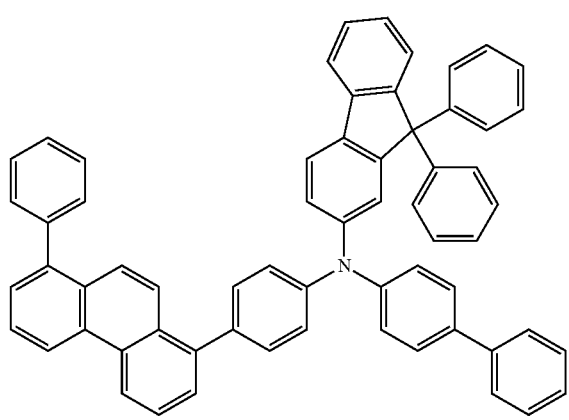
56
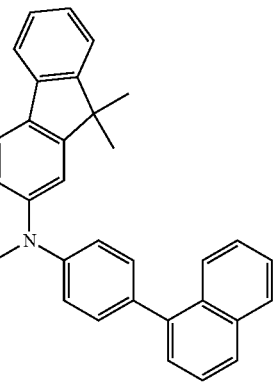
57
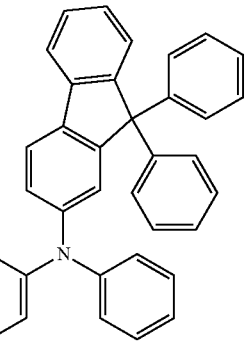
58
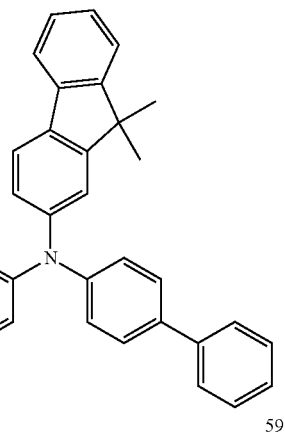
59
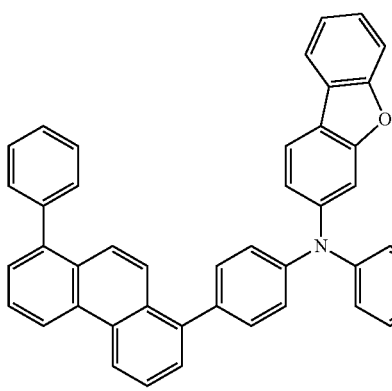

60
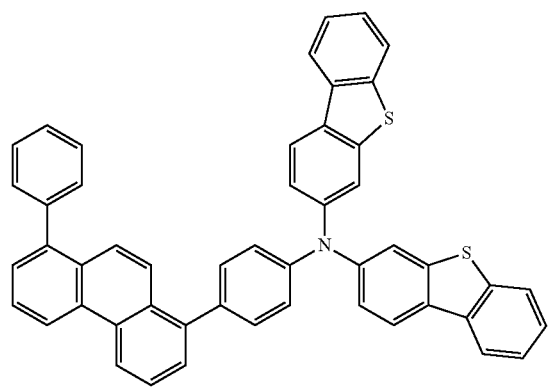
61
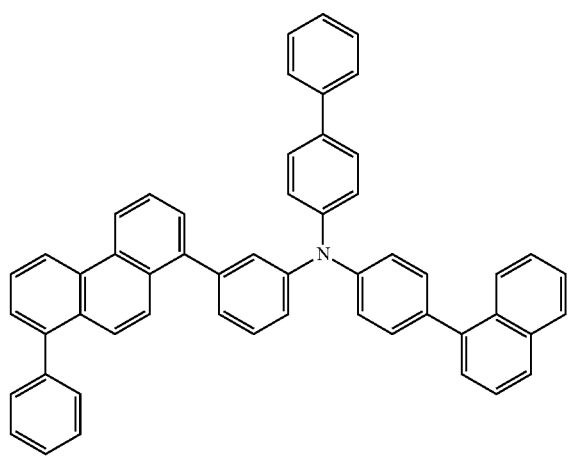
62
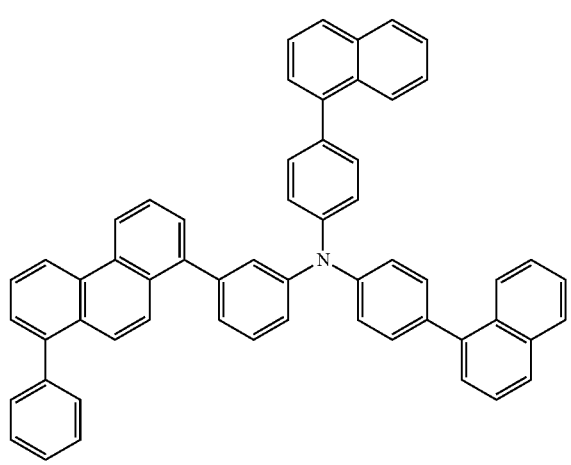
63
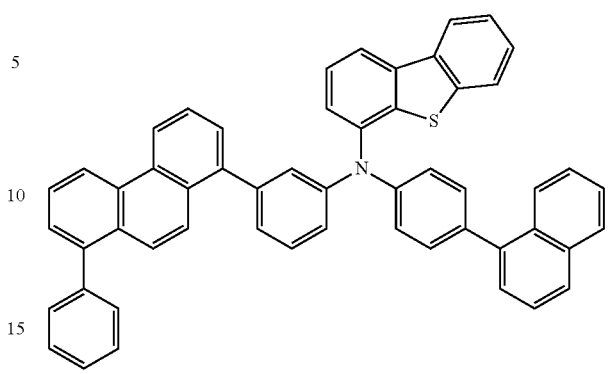
64
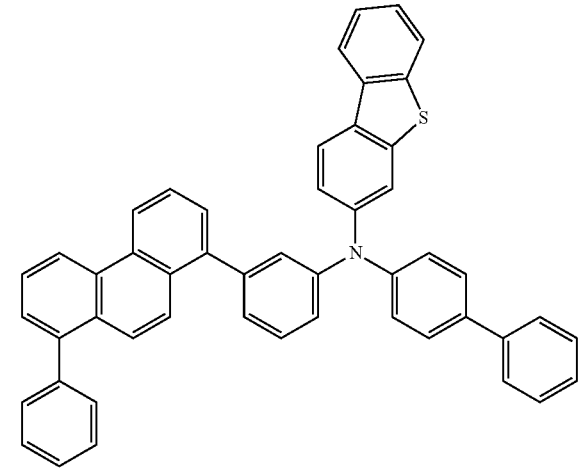
65

66
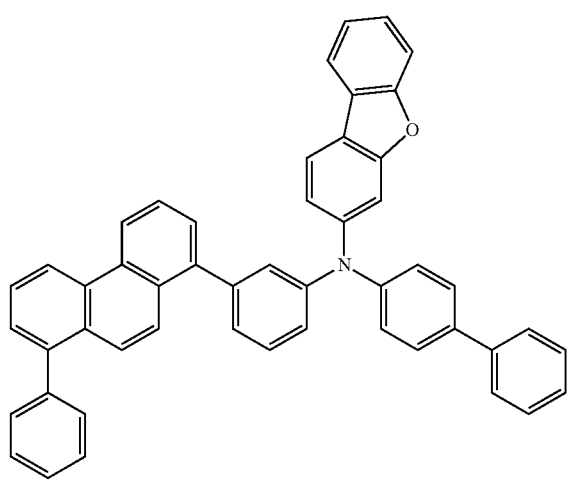
69
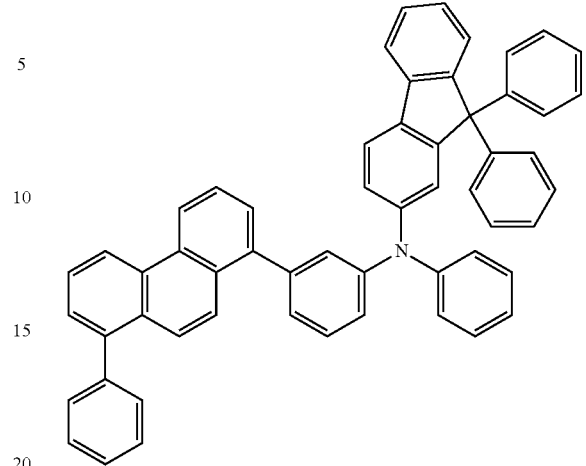
67
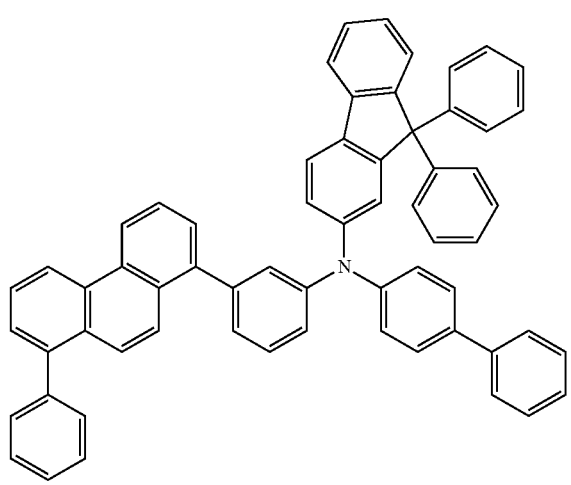
70
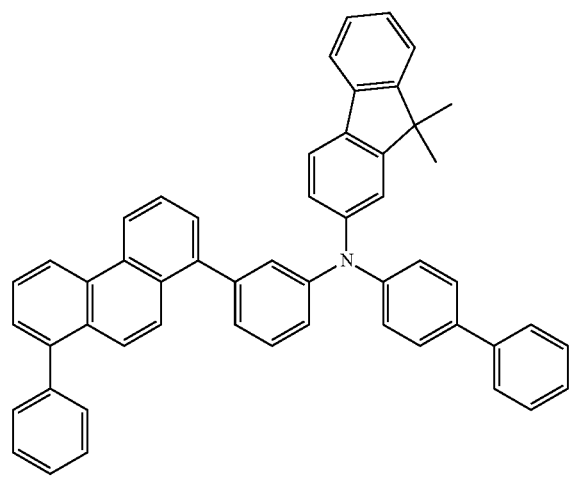
68
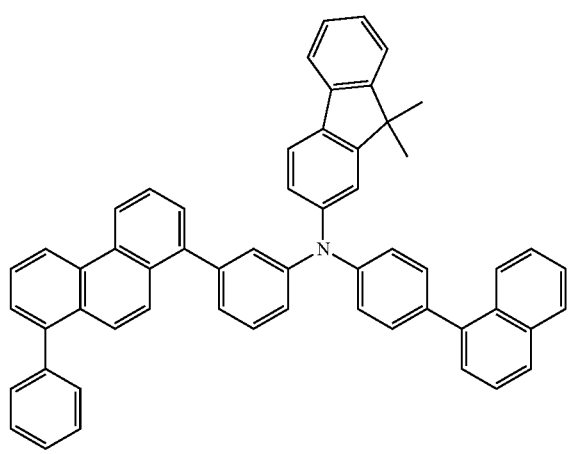
71
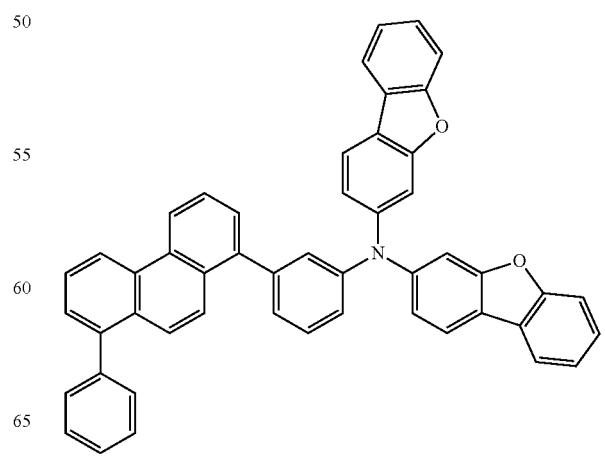

72
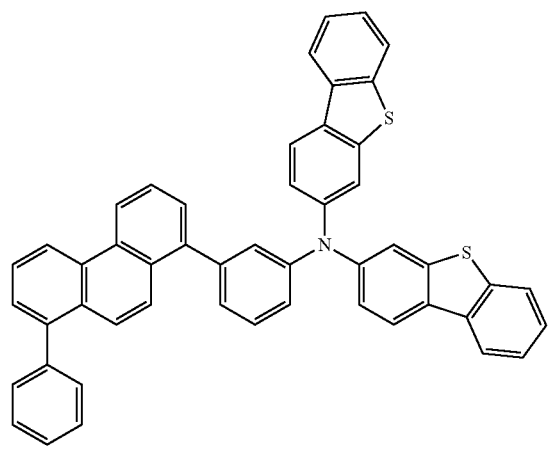
73
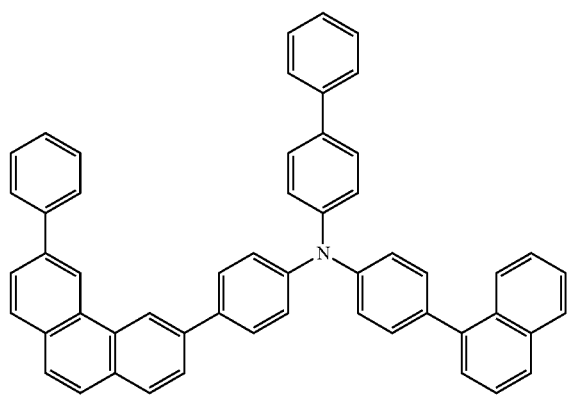
74
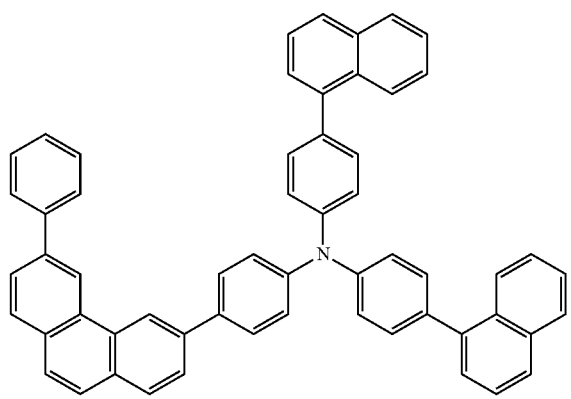
75
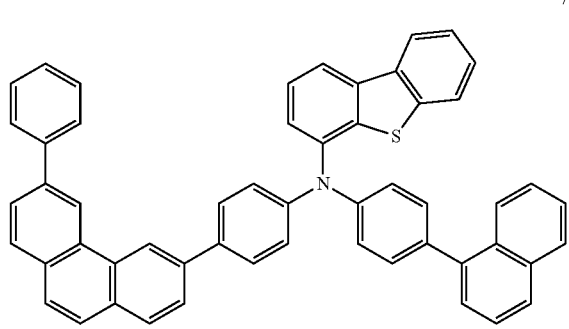
76
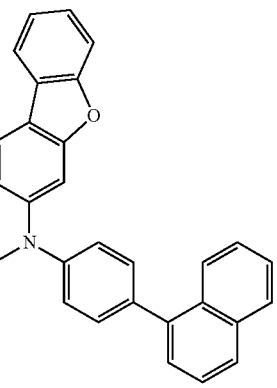
77
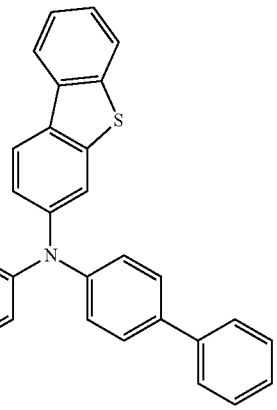
78
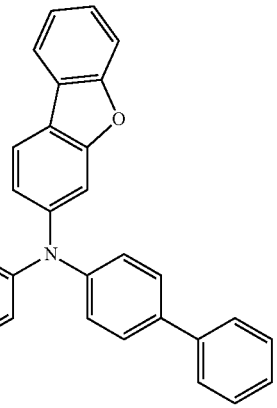

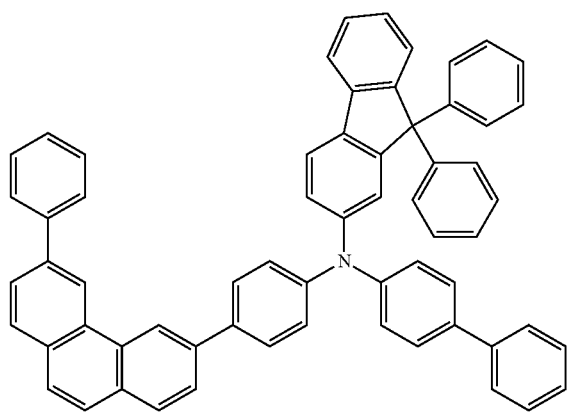
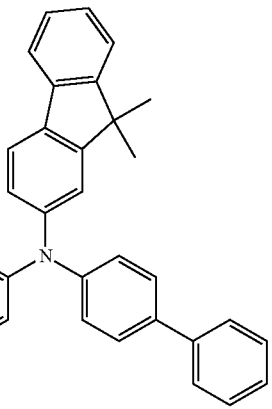
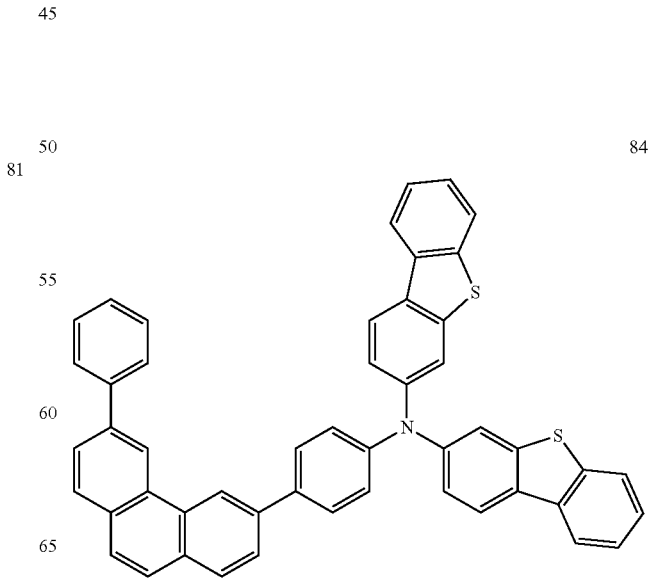

85
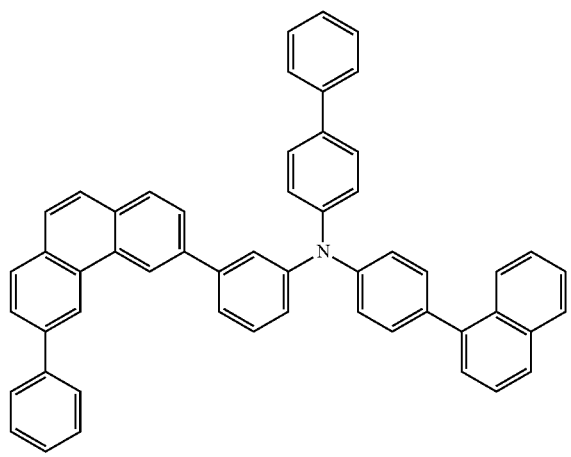
86
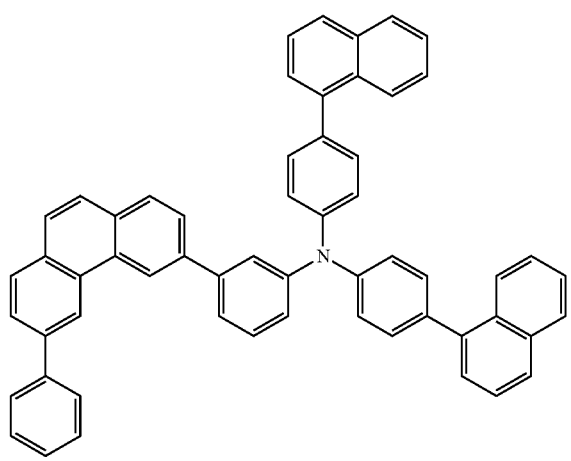
87
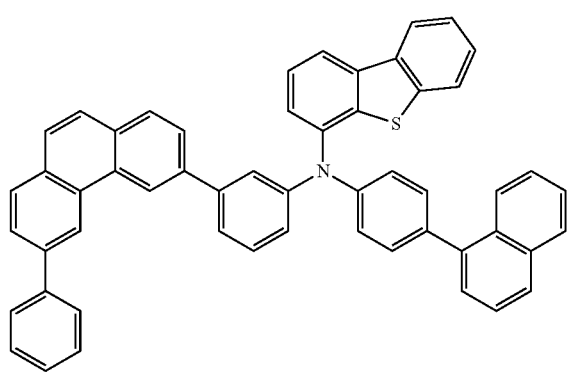
88
89
90
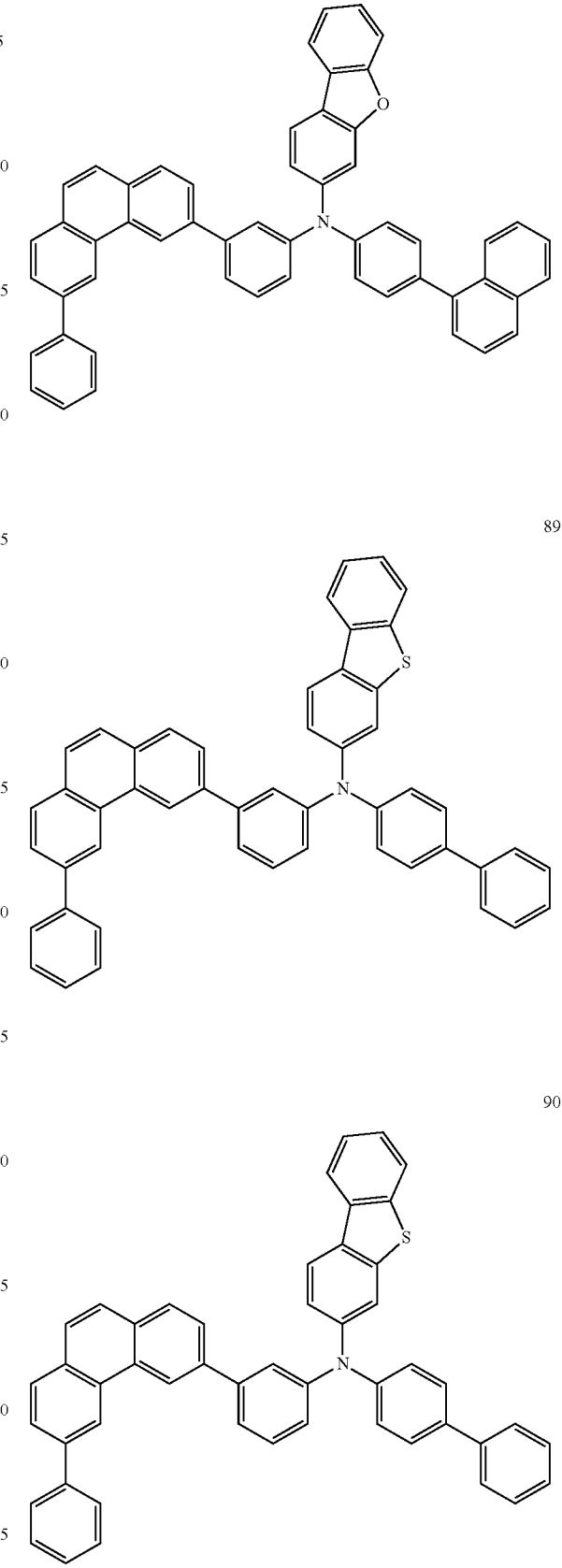

91
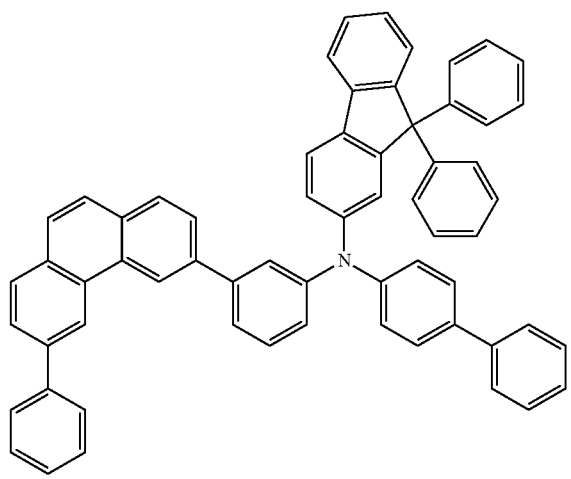
92
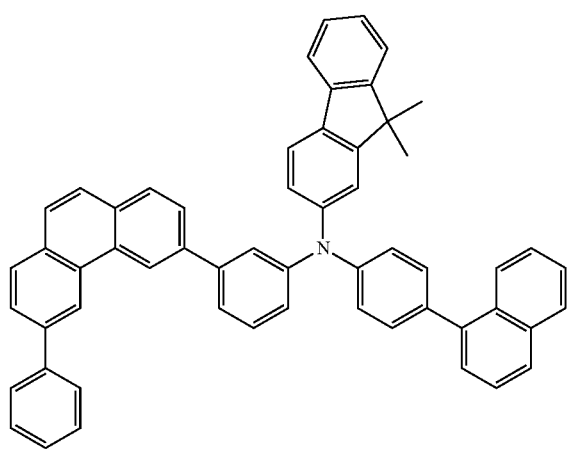
93
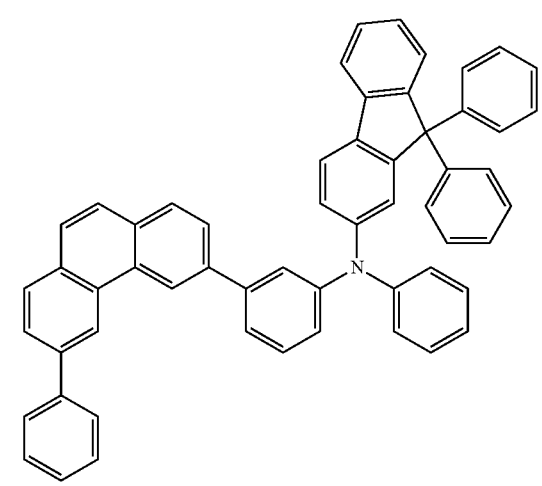
94
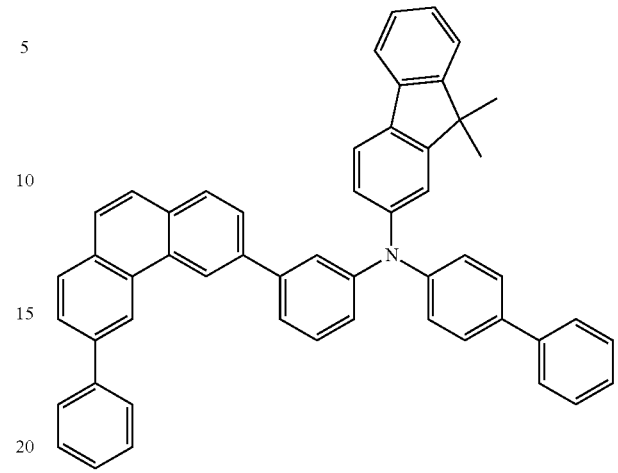
95
96
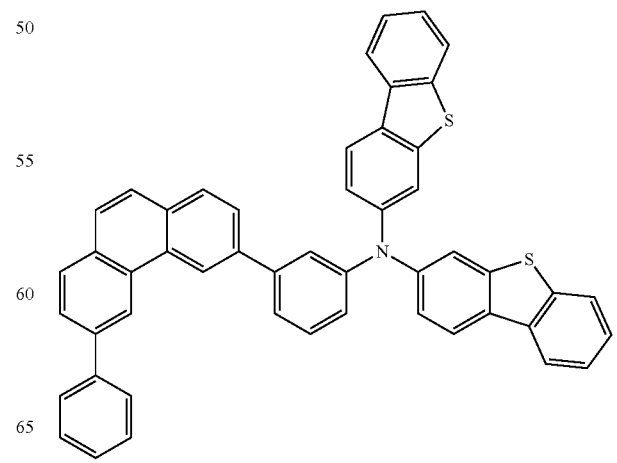

97
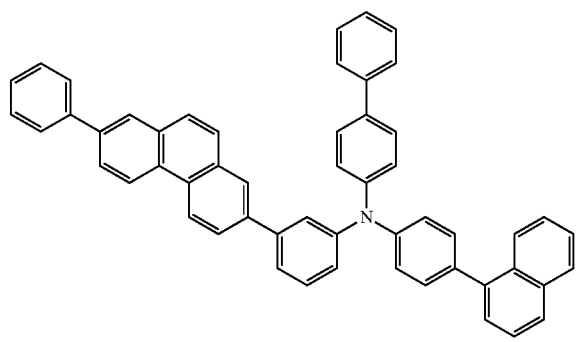
98
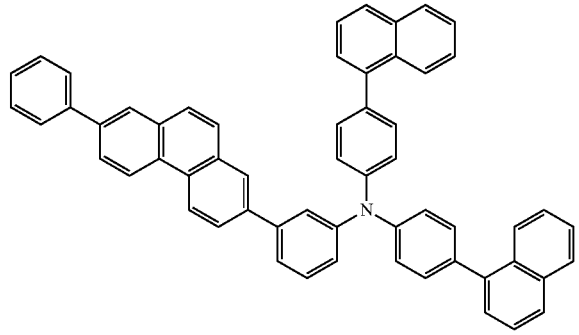
99
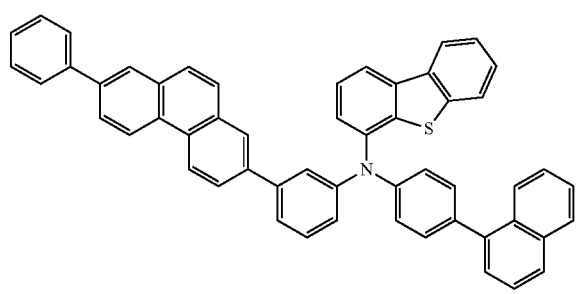
100
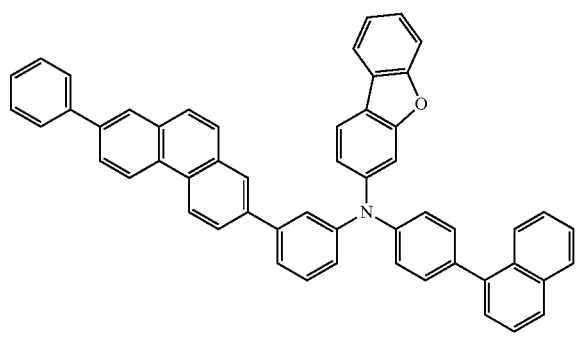
101
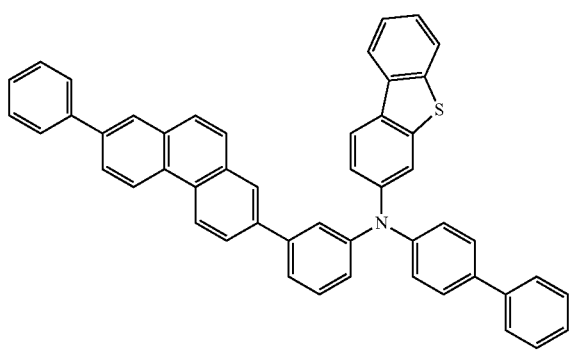
102
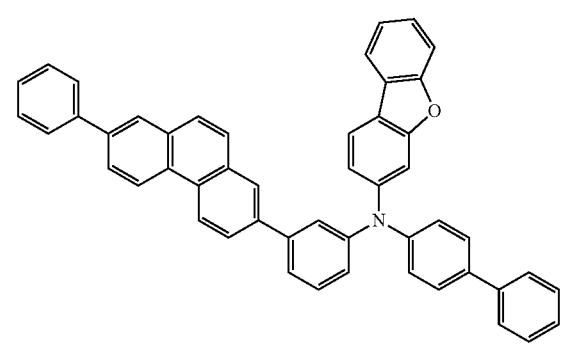
103
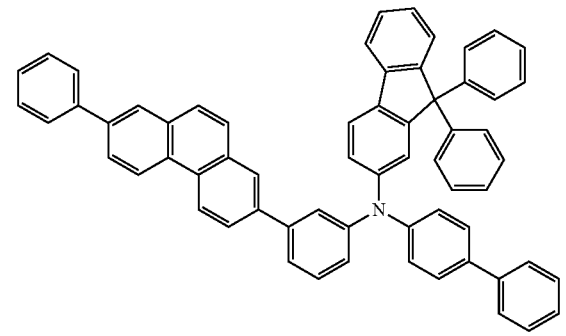
104

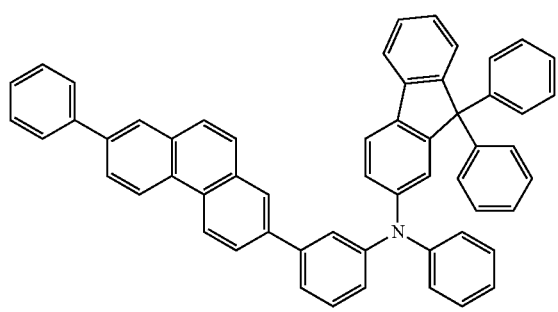

105

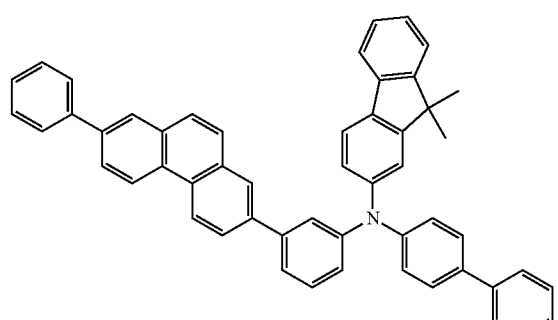

106

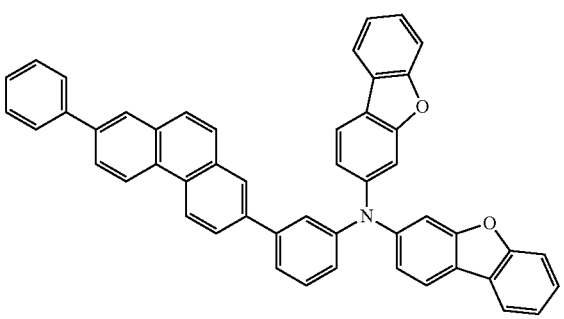

107

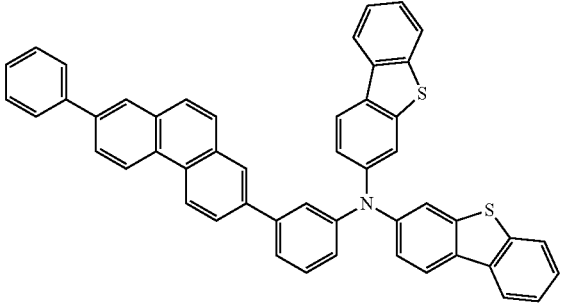

108

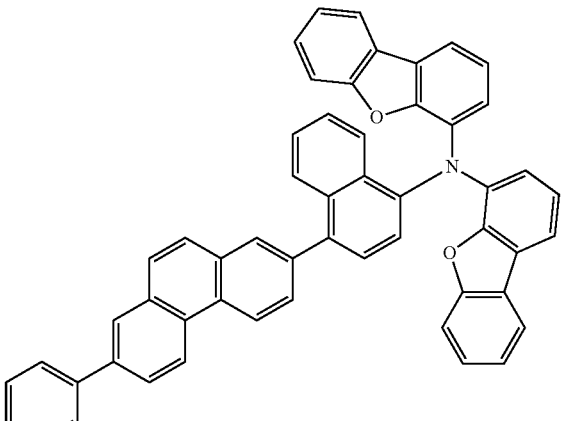

109

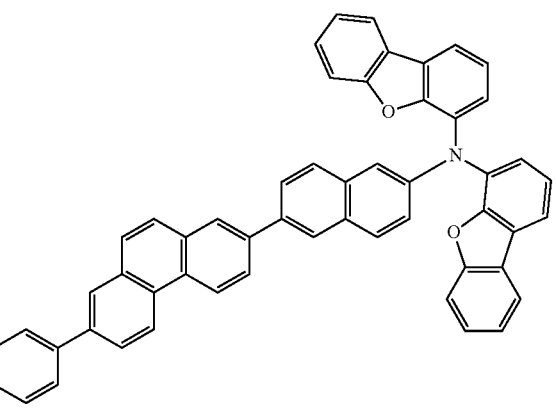

110

The monoamine compound according to an exemplary embodiment of the invention includes a phenanthryl group with high heat resistance and charge tolerance, and if applied to an organic electroluminescence device, the monoamine compound contributes to long life. In addition, since the phenanthryl group is substituted with one phenyl group, improving effect of layer quality may be obtained due to improving effect of charge tolerance and restraining effect of crystallization. Accordingly, the long life and high efficiency of the organic electroluminescence device may be achieved.

An exemplary embodiment of the invention provides a monoamine compound represented by the following Formula A:

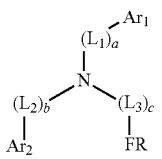

[Formula A]

In Formula A, $L_1$ to $L_3$ are each independently a direct linkage, a substituted or unsubstituted arylene group having 6 to 12 carbon atoms for forming a ring, or a substituted or unsubstituted heteroarylene group having 5 to 12 carbon atoms for forming a ring, "a" to "c" are each independently an integer of 0 to 2, $Ar_1$ and $Ar_2$ are each independently a substituted or unsubstituted aryl group having 6 to 30 carbon atoms for forming a ring, or a substituted or unsubstituted heteroaryl group having 5 to 12 carbon atoms for forming a ring.

The same explanation on $L_1$ to $L_3$, $Ar_1$, $Ar_2$ and "a" to "c" of Formula 1 may be applied to $L_1$ to $L_3$, $Ar_1$, $Ar_2$ and "a" to "c" of Formula A.

In Formula A, FR is represented by the following Formula B:

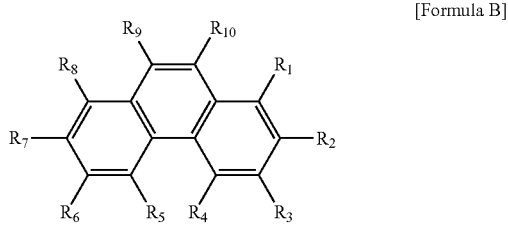

[Formula B]

In Formula B, at least one of $R_1$ to $R_4$ is a bonding part, the remainder of $R_1$ to $R_4$, and $R_5$ to $R_{10}$ are each independently a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 5 to 12 carbon atoms for forming a ring, and one of the remainder of $R_1$ to $R_4$, and $R_5$ to $R_{10}$ is a substituted or unsubstituted phenyl group.

The phenanthryl group represented by Formula B may be substituted with one or more substituents, and the number of a phenyl group among the substituents is one.

In Formula B, one of $R_1$ to $R_3$ is a bonding part, and the remainder of $R_1$ to $R_3$ may be hydrogen atoms.

The monoamine compound represented by Formula A may be, for example, any one selected from the compounds represented in Compound Group 1.

The monoamine compound represented by Formula A may be, for example, any one selected from the compounds represented in Compound Group 2.

The monoamine compound represented by Formula A includes a phenanthryl group which is substituted with one phenyl group, and if applied to an organic electroluminescence device, the monoamine compound may contribute to long life and high efficiency.

Referring to FIG. 1 to FIG. 3 again, an organic electroluminescence device according to an exemplary embodiment of the invention will be explained. An emission layer EML includes the monoamine compound according to an exemplary embodiment of the invention. For example, a hole transport region HTR includes a monoamine compound represented by Formula 1.

Hereinafter, different features from the above-described monoamine compound according to an exemplary embodiment of the invention will be explained in particular, and unexplained parts will follow the above explanation on the monoamine compound according to an exemplary embodiment of the invention.

A first electrode EL1 has conductivity. The first electrode EL1 may be a pixel electrode or an anode. The first electrode EL1 may be a transmissive electrode, a transflective electrode, or a reflective electrode. If the first electrode EL1 is the transmissive electrode, the first electrode EL1 may be formed using a transparent metal oxide such as indium tin oxide (ITO), indium zinc oxide (IZO), zinc oxide (ZnO), and indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including the reflective layer or transflective layer formed using the above materials, or a transparent layer formed using ITO, IZO, ZnO, or ITZO. For example, the first electrode EL1 may have a three-layer structure of ITO/Ag/ITO, but an exemplary embodiment of the invention is not limited thereto.

The thickness of the first electrode EL1 may be from about 1,000 Å to about 10,000 Å, for example, from about 1,000 Å to about 3,000 Å.

A hole transport region HTR is provided on the first electrode EL1. The hole transport region HTR may include at least one of a hole injection layer HIL, a hole transport layer HTL, a hole buffer layer, or an electron blocking layer EBL.

As described above, the hole transport region HTR includes the monoamine compound according to an exemplary embodiment of the invention. For example, the hole transport region HTR includes the monoamine compound represented by Formula 1. However, an exemplary embodiment of the invention is not limited thereto. The hole transport region HTR may include the monoamine compound represented by Formula A.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, and may have a single layer structure formed using a hole injection material and a hole transport material. Alternatively, the hole transport region HTR may have a single layer structure formed using a plurality of different materials, or a structure laminated from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, without limitation.

As described above, the hole transport region HTR may have a multilayer structure having a plurality of layers, and a layer making contact with the emission layer EML among the plurality of layers may include a monoamine compound represented by Formula 1. For example, the hole transport region HTR may include a hole injection layer HIL disposed on a first electrode EL1, a hole transport layer HTL disposed on the hole injection layer HIL, and an electron blocking layer EBL disposed on the hole transport layer HTL, wherein the electron blocking layer EBL may include a monoamine compound represented by Formula 1.

The hole transport region HTR may include one or two or more kinds of monoamine compounds represented by Formula 1. For example, the hole transport region HTR may include at least one selected from the compounds represented in Compound Group 1 and Compound Group 2.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4''-tris(3-methylphenylphenylamino) triphenylamine (m-MTDATA), 4,4',4''-tris(N,N-diphenylamino)triphenylamine (TDATA), 4,4',4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-(1,1'-benzidine (NPD), triphenylamine-containing polyether ketone (TPAPEK), 4-isopropyl-4'-methyldiphenyliodonium tetrakis(pentafluorophenyl)borate, dipyrazino[2,3-f: 2',3'-h] qunoxaline-2,3,6,7,10,11-hexacarbonitrile (HAT-CN), etc.

The hole transport layer HTL may include, for example, carbazole derivatives such as N-phenyl carbazole, and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4''-tris(N-carbazolyl)triphenylamine (TCTA), N,N'-di(1-naphthalene-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc.

The electron blocking layer EBL may include commonly known materials in the art. The electron blocking layer EBL may include, for example, carbazole derivatives such as N-phenyl carbazole, and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4''-tris(N-carbazolyl)triphenylamine (TCTA), N,N'-di(1-naphthalene-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), (1,3-Bis(N-carbazolyl)benzene)(mCP), etc. In addition, as described above, the electron blocking layer EBL may include the monoamine compound according to an exemplary embodiment of the invention.

The thickness of the hole transport region HTR may be from about 100 Å to about 10,000 Å, for example, from about 100 Å to about 5,000 Å. The thickness of the hole injection layer HIL may be from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be obtained without substantial increase of a driving voltage.

The hole transport region HTR may further include a charge generating material in addition to the above-described materials to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, without limitation. For example, non-limiting examples of the p-dopant may include quinone derivatives such as tetracyanoquinodimethane (TCNQ) and 2,3,5,6-tetrafluoro-7,7,8,8-tetracyanoquinodimethane (F4-TCNQ), metal oxides such as tungsten oxide, and molybdenum oxide, without limitation.

As described above, the hole transport region HTR may further include at least one of a hole buffer layer or an electron blocking layer EBL. The hole buffer layer may compensate a resonance distance according to the wavelength of light emitted from the emission layer EML and increase light emission efficiency. Materials included in the hole transport region HTR may be used as materials included in the hole buffer layer. The electron blocking layer EBL is a layer preventing electron injection from the electron transport region ETR to the hole transport region HTR.

An emission layer EML is provided on the hole transport region HTR. The emission layer EML may have a thickness of, for example, from about 100 Å to about 1,000 Å, or from about 100 Å to about 600 Å. The emission layer EML may have a single layer formed using a single material, a single layer formed using a plurality of different materials, or a multilayer structure having a plurality of layers formed using a plurality of different materials.

As the material of the emission layer EML, known luminescent materials may be used, and may be selected from fluoranthene derivatives, pyrene derivatives, arylacetylene derivatives, anthracene derivatives, fluorene derivatives, perylene derivatives, chrysene derivatives, etc., without limitation. Preferably, pyrene derivatives, perylene derivatives, anthracene derivatives, etc., may be used. For example, as the host material of the emission layer EML, anthracene derivatives represented by Formula 4 below may be used.

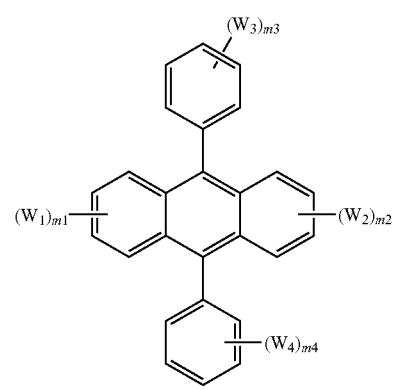

[Formula 4]

In Formula 4, $W_1$ to $W_4$ are each independently a hydrogen atom, a deuterium atom, a halogen atom, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, m1 and m2 are each independently an integer of 0 to 4, and m3 and m4 are each independently an integer of 0 to 5.

If m1 is 1, $W_1$ may not be a hydrogen atom, if m2 is 1, $W_2$ may not be a hydrogen atom, if m3 is 1, $W_3$ may not be a hydrogen atom, and if m4 is 1, $W_4$ may not be a hydrogen atom.

If m1 is 2 or more, a plurality of $W_1$ groups are the same or different. If m2 is 2 or more, a plurality of $W_2$ groups are the same or different. If m3 is 2 or more, a plurality of $W_3$ groups are the same or different. If m4 is 2 or more, a plurality of $W_4$ groups are the same or different.

The compound represented by Formula 4 may include, for example, the compounds represented by the structures a-1 to a-12 below. However, an exemplary embodiment of the compound represented by Formula 4 is not limited thereto.
a-1
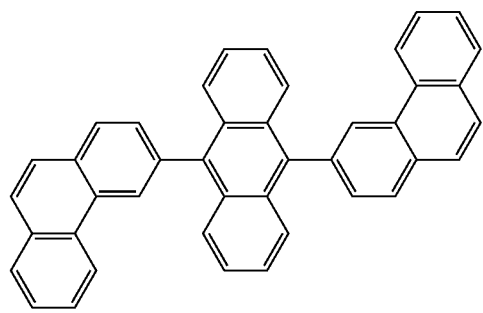
a-2
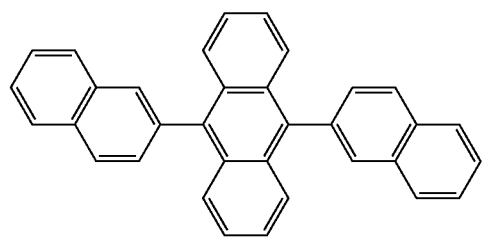
a-3
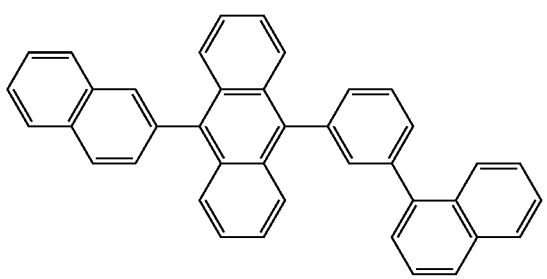
a-4
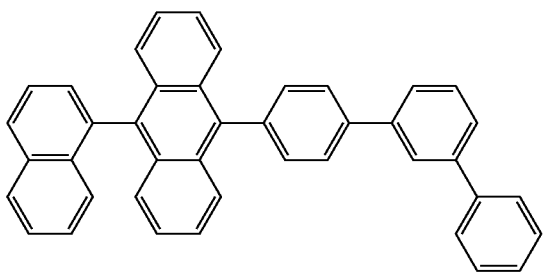
a-5
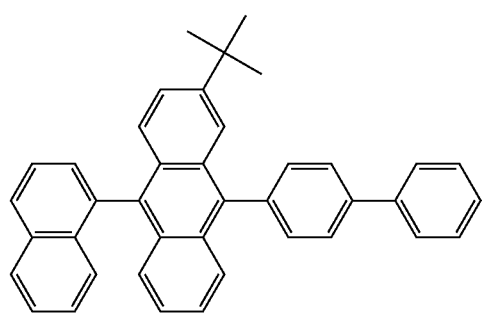
-continued
a-6
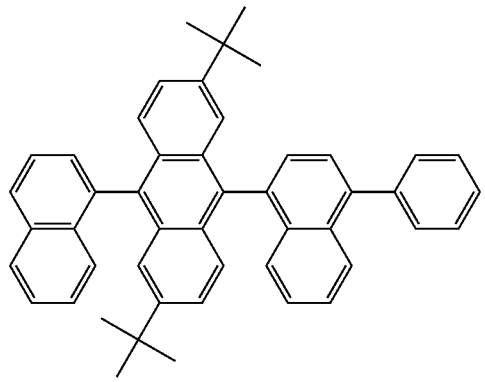
a-7
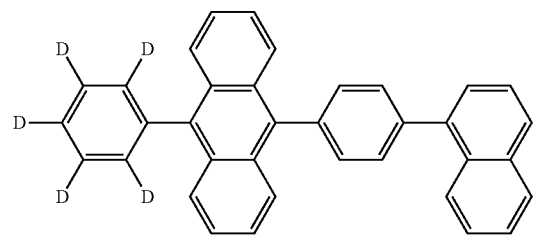
a-8
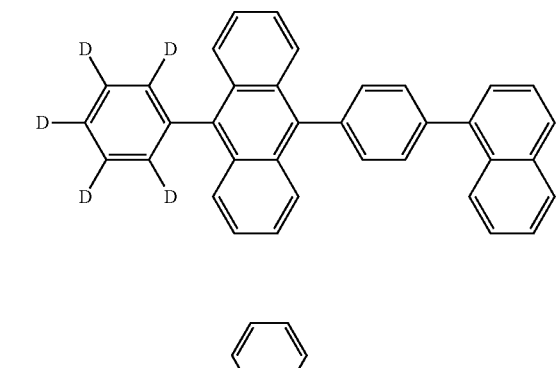
a-9
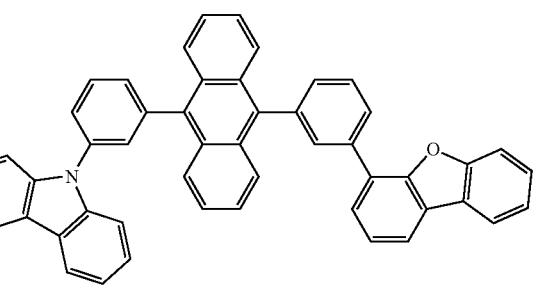
a-10
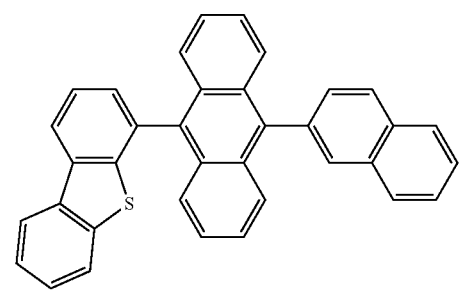

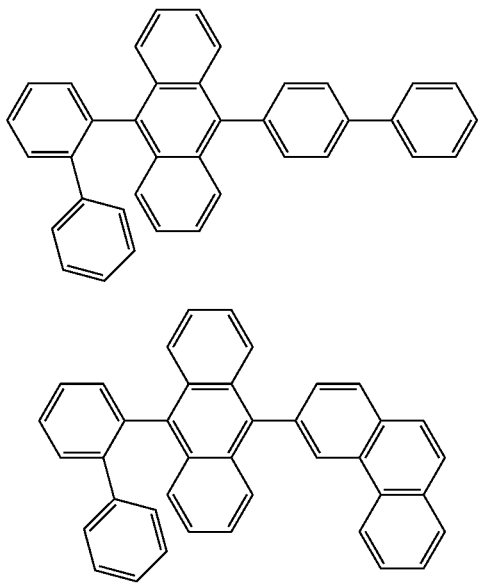

a-11 a-12

The emission layer EML may use a pyrene derivative as a dopant material. An exemplary embodiment of the pyrene derivative is not limited thereto, but may be a diamine compound.

The emission layer EML may include a fluorescence material including one selected from the group consisting of spiro-DPVBi, 2,2',7,7'-tetrakis(biphenyl-4-yl)-9,9'-spirobifluorene (spiro-sexiphenyl, spiro-6P), distyryl-benzene (DSB), distyryl-arylene (DSA), a polyfluorene (PFO)-based polymer and a poly(p-phenylene vinylene) (PPV)-based polymer.

The emission layer EML may further include a dopant, and the dopant may use a known material. For example, styryl derivatives (for example, 1,4-bis[2-(3-N-ethylcarbazoryl)vinyl]benzene (BCzVB), 4-(di-p-tolylamino)-4"-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi)), perylene and the derivatives thereof (for example, 2,5,8,11-tetra-t-butylperylene (TBPe)), pyrene and the derivatives thereof (for example, 1,1-dipyrene, 1,4-dipyrenylbenzene, 1,4-bis(N,N-diphenylamino)pyrene, 1,6-bis(N,N-diphenylamino)pyrene, 2,5,8,11-tetra-t-butylperylene (TPB), 1,3,5-tris(N-phenyl-benzimidazole-2-yl)benzene (TPBi)), etc. may be used as the dopant.

The emission layer EML may include, for example, tris(8-hydroxyquinolino)aluminum (Alq$_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4"-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO$_3$), octaphenylcyclotetra siloxane (DPSiO$_4$), 2,8-bis(diphenylphosphoryl)dibenzofuran (PPF), etc. may be further included.

An electron transport region ETR is provided on the emission layer EML. The electron transport region ETR may include at least one of a hole blocking layer HBL, an electron transport layer ETL, and an electron injection layer EIL, without limitation.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. Further, the electron transport region ETR may have a single layer structure having a plurality of different materials, or a structure laminated from the emission layer EML of electron transport layer ETL/electron injection layer EIL, or hole blocking layer HBL/electron transport layer ETL/electron injection layer EIL, without limitation. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes an electron transport layer ETL, the electron transport region ETR may include tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, bis[2-(diphenylphosphino)phenyl]ether oxide (DPEPO), 2-(4-(N-phenylbenzoimidazolyl-1-ylphenyl)-9,10-dinaphthyl-anthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebq2), 9,10-di(naphthalene-2-yl)anthracene (ADN), and a mixture thereof. However, an exemplary embodiment of the invention is not limited thereto.

The electron transport layer ETL may include triphenylene derivatives, without limitation.

The thickness of the electron transport layer ETL may be from about 100 Å to about 1,000 Å, for example, from about 150 Å to about 500 Å. If the thickness of the electron transport layer ETL satisfies the above-described range, satisfactory electron transport properties may be obtained without substantial increase of a driving voltage.

If the electron transport region ETR includes the electron injection layer EIL, the electron transport region ETR may use LiF, 8-hydroxyquinolinolato-lithium (LiQ), LizO, BaO, NaCl, CsF, a metal in lanthanoides such as Yb, or a metal halide such as RbCl, and RbI. However, an exemplary embodiment of the invention is not limited thereto. The electron injection layer EIL may also be formed using a mixture material of an electron transport material and an insulating organo metal salt. The organo metal salt may be a material having an energy band gap of about 4 eV or more. Particularly, the organo metal salt may include, for example, metal acetates, metal benzoates, metal acetoacetates, metal acetylacetonates, or metal stearates. The thickness of the electron injection layer EIL may be from about 1 Å to about 100 Å, from 3 Å to about 90 Å. If the thickness of the electron injection layer EIL satisfies the above-described range, satisfactory electron injection properties may be obtained without substantial increase of a driving voltage.

The electron transport region ETR may include a hole blocking layer HBL as described above. The hole blocking layer HBL may include, for example, 2,9-dimethyl-4,7-diphenyl-1,10-phenanthroline (BCP), 4,7-diphenyl-1,10-phenanthroline (Bphen), or bis[2-(diphenylphosphino)phenyl]ether oxide (DPEPO). However, an exemplary embodiment of the invention is not limited thereto.

A second electrode EL2 is provided on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

Though not shown, the second electrode EL2 may be connected with an auxiliary electrode. If the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light via transition from an excited state to a ground state.

If the organic electroluminescence device 10 is a top emission type, the first electrode EL1 may be a reflective electrode and the second electrode EL2 may be a transmissive electrode or a transflective electrode. If the organic electroluminescence device 10 is a bottom emission type, the first electrode EL1 may be a transmissive electrode or a transflective electrode and the second electrode EL2 may be a reflective electrode.

The organic electroluminescence device 10 according to an exemplary embodiment of the invention is characterized in including the monoamine compound, represented by Formula 1 or Formula A, and thus, high emission efficiency and long life may be achieved.

Hereinafter, the present disclosure will be explained in more detail with reference to particular exemplary embodiments and comparative examples. The following embodiments are only illustrations to assist the understanding of the invention, and the scope of the invention is not limited thereto.

SYNTHETIC EXAMPLES

The monoamine compounds according to exemplary embodiments of the invention may be synthesized, for example, as follows. However, an exemplary embodiment of the synthetic method of the monoamine compound according to an exemplary embodiment of the invention is not limited thereto.

1. Synthesis of Compound 11

Compound 11, which is a monoamine compound according to an exemplary embodiment of the invention, may be synthesized, for example, by the reaction below.

(Synthesis of Intermediate Compound A)

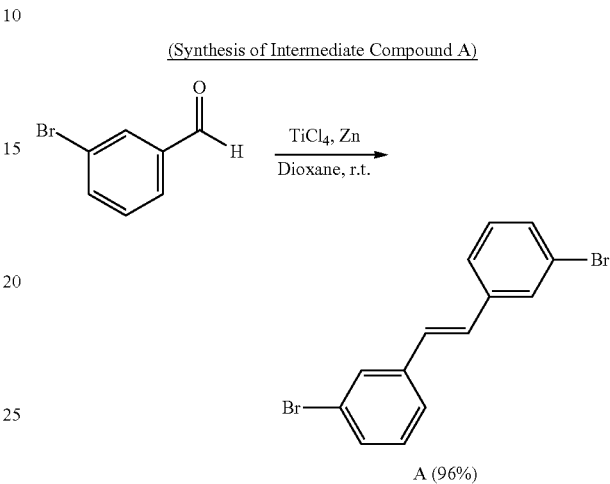

Under an argon (Ar) atmosphere, to a 200 ml three-neck flask, 7.40 g of 3-bromo-benzaldehyde, 5.30 ml of titanium (IV) chloride, and 60 ml of a THF solution in which 6.31 g of a zinc powder was dissolved, were added, followed by heating in a microwave oven with about 10 W, at about 110° C. for about 10 minutes. After cooling in the air, dichloromethane was added, an organic layer was separately taken, and solvents were removed by distillation. The crude product thus obtained was separated by silica gel chromatography (using hexane and toluene), and 1.30 g (yield 96%) of Compound A was obtained as a white solid.

The molecular weight of Compound A measured by GC-MS was 338.

(Synthesis of Intermediate Compound B)

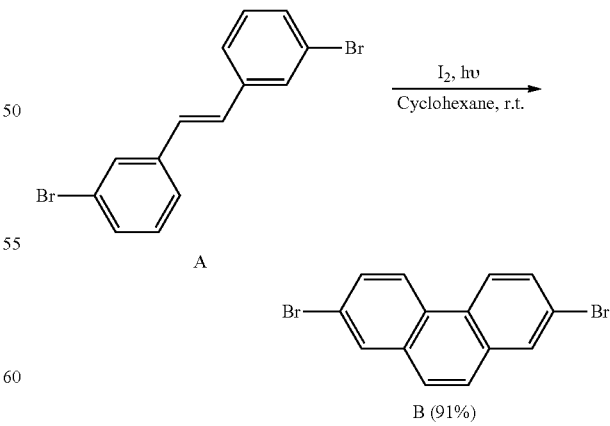

Under the atmosphere, 4.00 g of Intermediate Compound A, and 100 ml of a cyclohexane solution in which 0.17 g of iodine was dissolved were added to a 300 ml reaction container, and a 450-W, high-pressure Hg arc lamp (>280 nm) was irradiated for about 10 hours. After the irradiation, a solid in the reaction solution was filtered with suction to obtain 3.62 g (yield 91%) of Compound B as a white solid.

The molecular weight of Compound B measured by FAB-MS was 336.

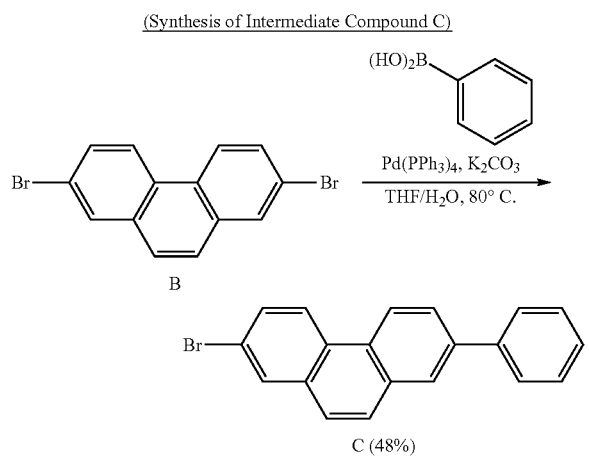

(Synthesis of Intermediate Compound C)

Under an argon (Ar) atmosphere, to a 500 ml three-neck flask, 11.1 g of Intermediate Compound B (2,7-dibromophenanthrene), 2.02 g of phenylboronic acid, 0.574 g of Pd(PPh$_3$)$_4$, and 190 ml of a mixture solution of THF/water (8:2) in which 4.58 g of K$_2$CO$_3$ was dissolved, were added, followed by heating and stirring at about 70° C. for about 5 hours. After cooling in the air, dichloromethane was added, an organic layer was separately taken, and solvents were removed by distillation. The crude product thus obtained was separated by silica gel chromatography (using hexane) to obtain 2.65 g (yield 48%) of Compound C as a white solid.

The molecular weight of Compound C measured by GC-MS was 332.

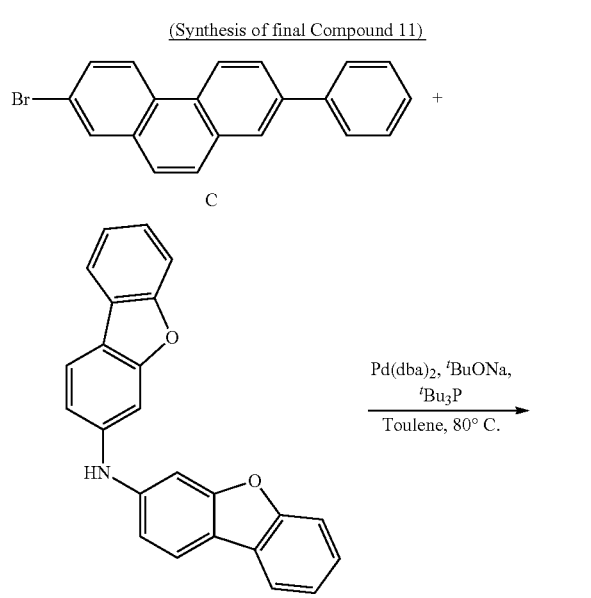

(Synthesis of final Compound 11)

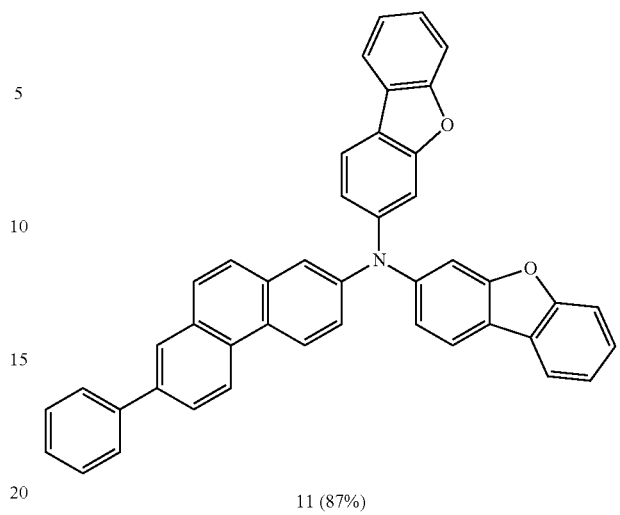

11 (87%)

Under an argon (Ar) atmosphere, to a 100 ml three-neck flask, 2.50 g of N-3-dibenzofuranyl-3-dibenzofuranamine, 2.38 g of Intermediate Compound C, 0.10 g of tBu$_3$P, and 33 ml of an anhydrous toluene solution in which 1.36 g of tBuONa was dissolved, were added, followed by heating and stirring at about 80° C. for about 5 hours. After cooling in the air, dichloromethane was added, an organic layer was separately taken, and solvents were removed by distillation. The crude product thus obtained was separated by silica gel chromatography (using toluene and hexane) to obtain 3.75 g (yield 87%) of Compound 11 as a pale yellow solid.

The molecular weight of Compound 11 measured by FAB-MS was 602.

2. Synthesis of Compound 13

Compound 13, which is a monoamine compound according to an exemplary embodiment of the invention, may be synthesized, for example, by the reaction below.

(Synthesis of Intermediate Compound D)

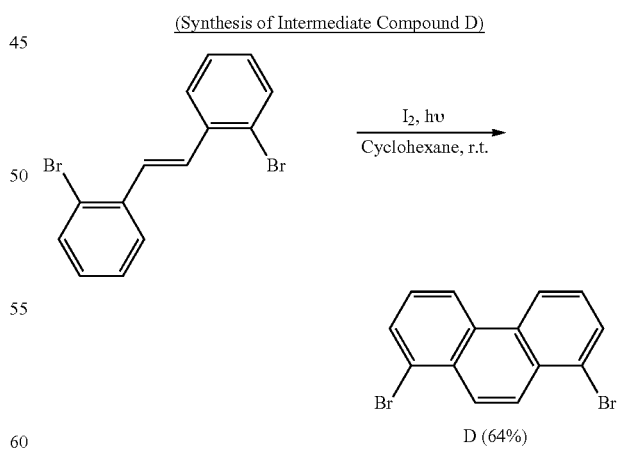

D (64%)

Intermediate Compound D was synthesized by the same synthetic method of Intermediate Compound B except for using 1,1'-(1,2-ethenediyl)bis[2-bromobenzene] instead of Intermediate Compound A. The molecular weight of Intermediate Compound D measured by FAB-MS was 336.

(Synthesis of Intermediate Compound E)

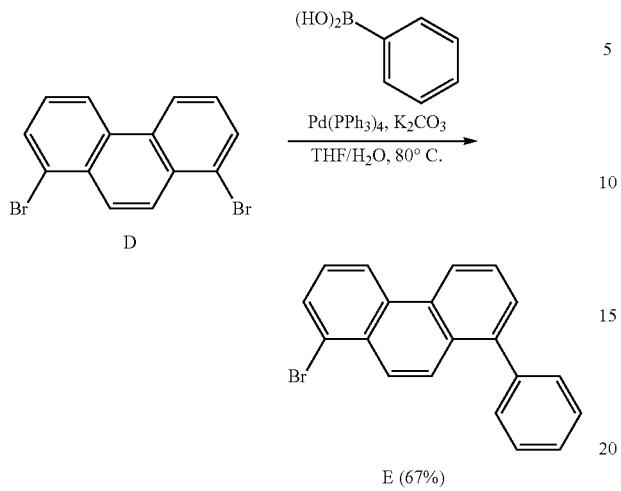

E (67%)

Intermediate Compound E was synthesized by the same synthetic method of Intermediate Compound C except for using Intermediate Compound D instead of Intermediate Compound B. The molecular weight of Intermediate Compound E measured by GC-MS was 334.

(Synthesis of final Compound 13)

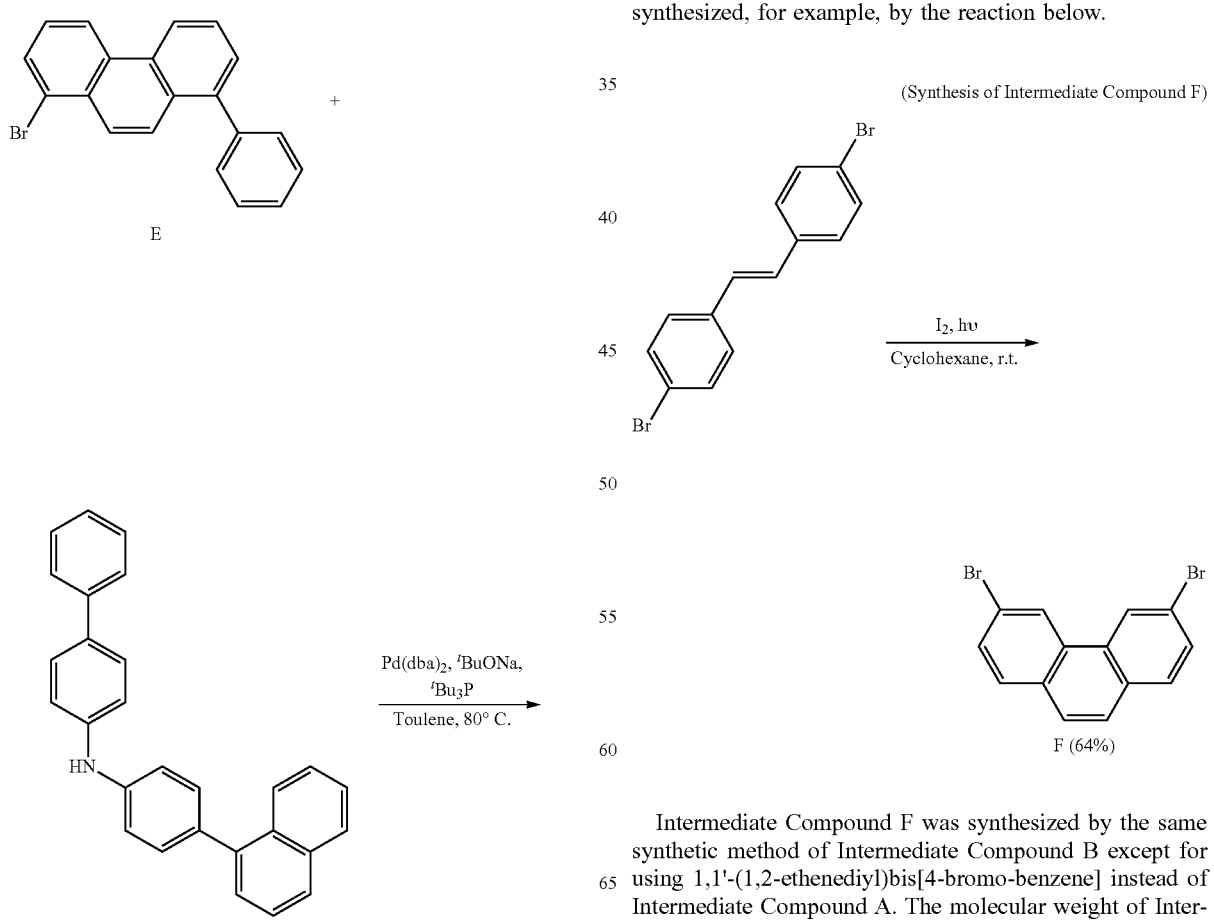

13 (91%)

Compound 13 was synthesized by the same synthetic method of Compound 11 except for using Intermediate Compound E instead of Intermediate Compound C and N-[4-(1-naphthalenyl)phenyl]-[1,1'-biphenyl]-4-amine instead of N-3-dibenzofuranyl-3-dibenzofuranamine. The molecular weight of Compound 13 measured by FAB-MS was 624.

3. Synthesis of Compound 25

Compound 25, which is a monoamine compound according to an exemplary embodiment of the invention, may be synthesized, for example, by the reaction below.

(Synthesis of Intermediate Compound F)

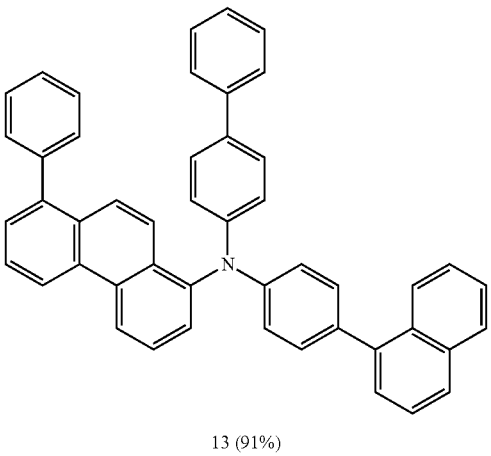

F (64%)

Intermediate Compound F was synthesized by the same synthetic method of Intermediate Compound B except for using 1,1'-(1,2-ethenediyl)bis[4-bromo-benzene] instead of Intermediate Compound A. The molecular weight of Intermediate Compound F measured by GC-MS was 334.

(Synthesis of Intermediate Compound G)

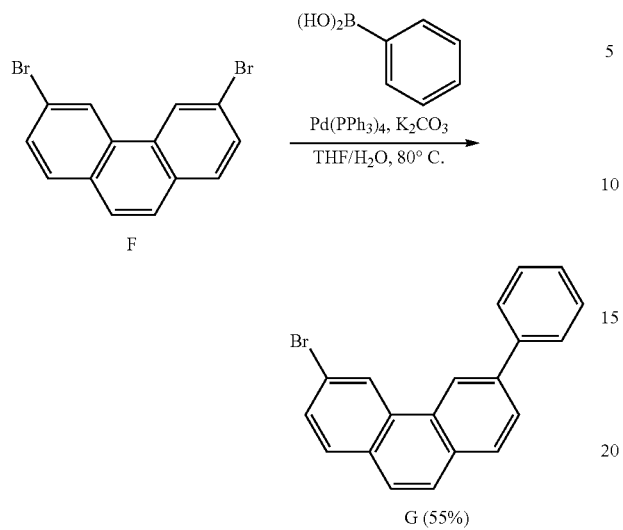

Intermediate Compound G was synthesized by the same synthetic method of Intermediate Compound C except for using Intermediate Compound F instead of Intermediate Compound B. The molecular weight of Intermediate Compound G measured by GC-MS was 332.

(Synthesis of final Compound 25)

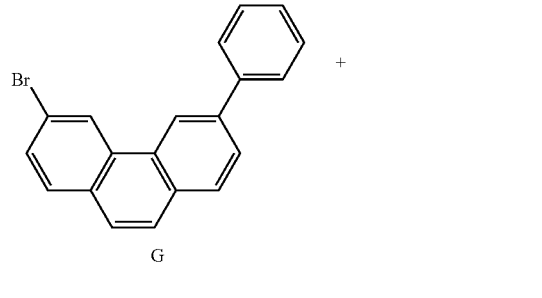

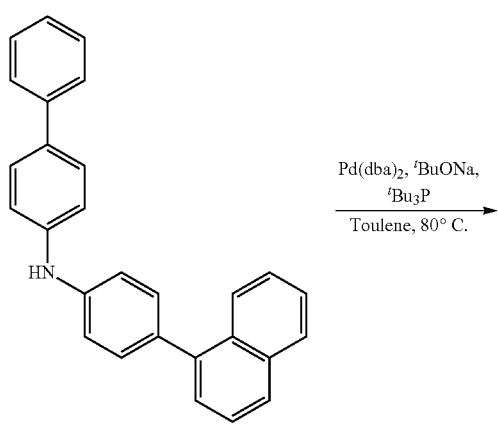

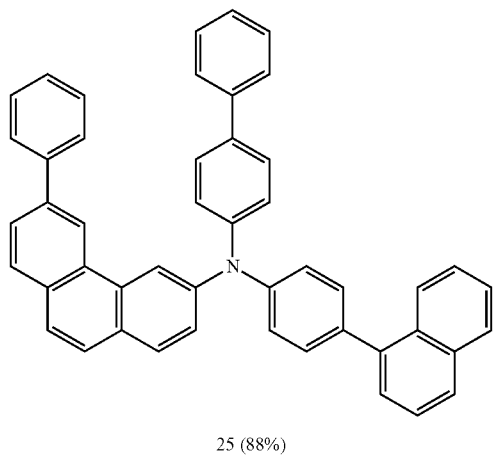

Compound 25 was synthesized by the same synthetic method of Compound 13 except for using Intermediate Compound G instead of Intermediate Compound E. The molecular weight of Compound 25 measured by FAB-MS was 623.

4. Synthesis of Compound 57

Compound 57, which is a monoamine compound according to an exemplary embodiment of the invention, may be synthesized, for example, by the reaction below.

(Synthesis of Intermediate Compound H)

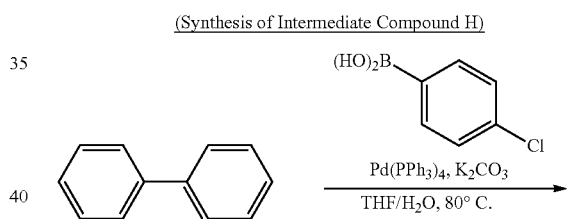

Intermediate Compound H was synthesized by the above-described synthetic method of Intermediate Compound E except for using 4-chlorophenylboronic acid instead of phenylboronic acid. The molecular weight of Intermediate Compound H measured by GC-MS was 364.

(Synthesis of final Compound 57)

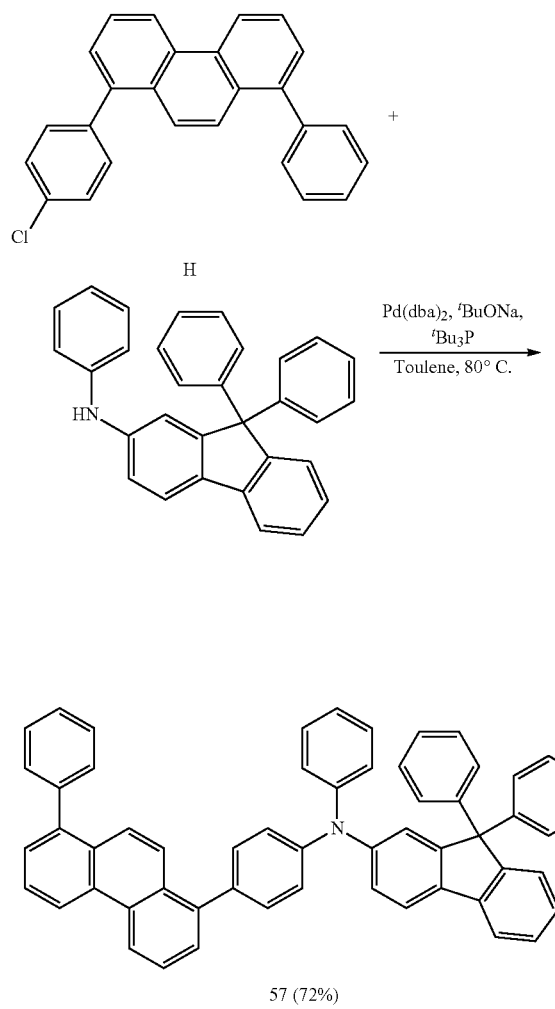

57 (72%)

Compound 57 was synthesized by the same synthetic method of Compound 11 except for using Intermediate Compound H instead of Intermediate Compound C and N-9,9-triphenyl-9H-fluoren-2-amine instead of N-3-dibenzofuranyl-3-dibenzofuranamine. The molecular weight of Compound 57 measured by GC-MS was 737.

5. Synthesis of Compound 69

Compound 69, which is a monoamine compound according to an exemplary embodiment of the invention, may be synthesized, for example, by the reaction below.

(Synthesis of Intermediate Compound I)

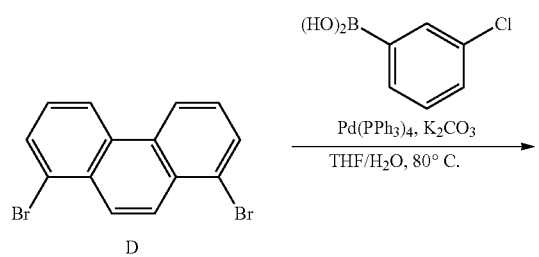

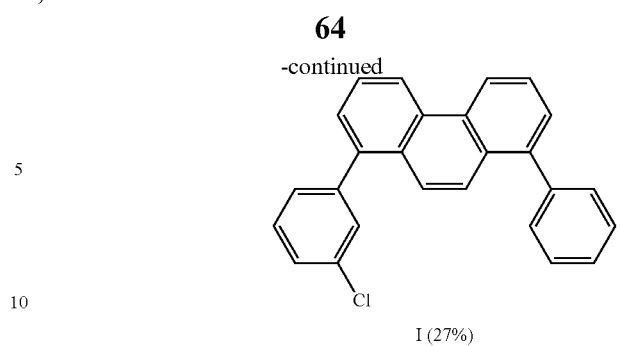

I (27%)

Intermediate Compound I was synthesized by the same synthetic method of Intermediate Compound H except for using 3-chlorophenylboronic acid instead of 4-chlorophenylboronic acid. The molecular weight of Intermediate Compound I measured by GC-MS was 364.

(Synthesis of final Compound 69)

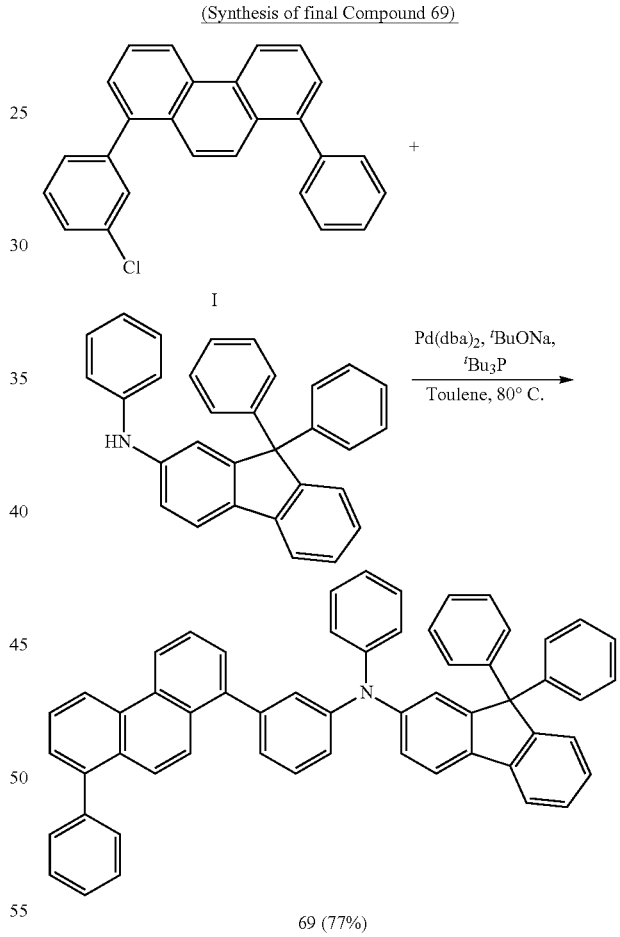

69 (77%)

Compound 69 was synthesized by the above-described synthetic method of Compound 57 except for using Intermediate Compound I instead of Intermediate Compound H. The molecular weight of Compound 69 measured by FAB-MS was 737.

[1H NMR (CDCl$_3$, 25° C., 300 Hz) δ=8.32-8.22 (m, 6H), 7.96 (d, J=7.0 Hz, 2H), 7.93-7.86 (m, 5H), 7.73-7.68 (m, 5H), 7.55 (d, J=7.2 Hz, 4H), 7.36-7.25 (m, 5H), 7.25-7.15 (m, 6H), 7.12-7.01 (m, 6H)]

6. Synthesis of Compound 73

Compound 73, which is a monoamine compound according to an exemplary embodiment of the invention, may be synthesized, for example, by the reaction below.

(Synthesis of Intermediate Compound J)

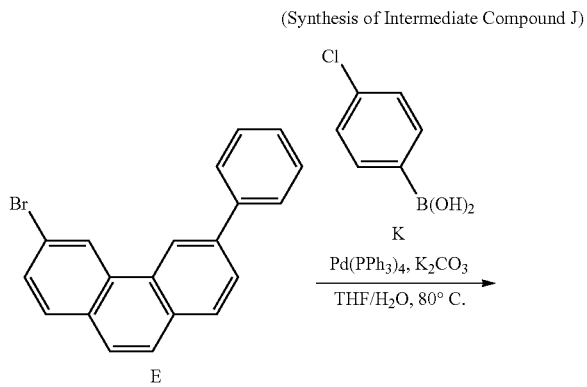

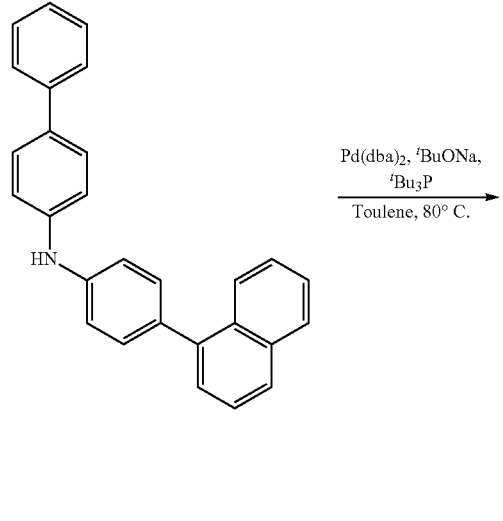

To Intermediate Compound E, 1.48 g of Compound K and 700 ml of a mixture solution of THF/water (8:2) in which 35.0 g of potassium carbonate was dissolved, were added and deaerated, followed by heating and stirring under an argon (Ar) atmosphere at about 70° C. for about 5 hours. After cooling in the air, dichloromethane was added, an organic layer was separated and taken, and solvents were removed by distillation. The crude product thus obtained was separated by silica gel chromatography to obtain 7.80 g (yield 83%) of Intermediate Compound J as a pale yellow solid. The molecular weight of Intermediate Compound J measured by GC-MS was 334.

(Synthesis of final Compound 73)

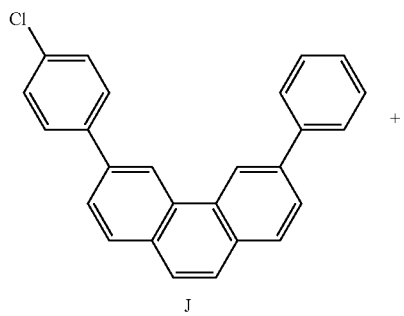

+

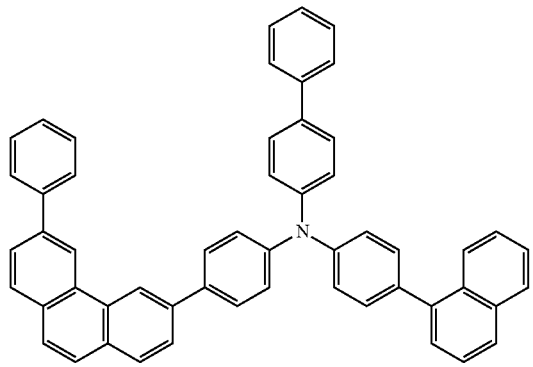

8.75 g (yield 76%) of final Compound 73 was synthesized by the same synthetic method of Compound 13 except for using Intermediate Compound J instead of Intermediate Compound C. The molecular weight of Compound 73 measured by FAB-MS was 699.

Device Manufacturing Examples

Organic electroluminescence devices of Examples 1 to 6 were manufactured using each of Compounds 11, 13, 25, 57, 69 and 73 as a material for an electron blocking layer.

Example Compounds
11
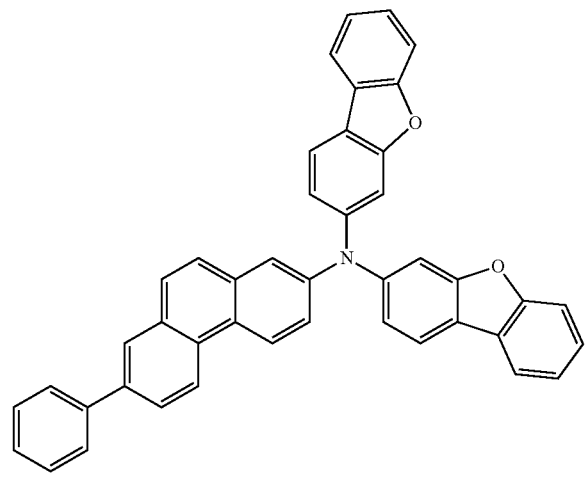
13
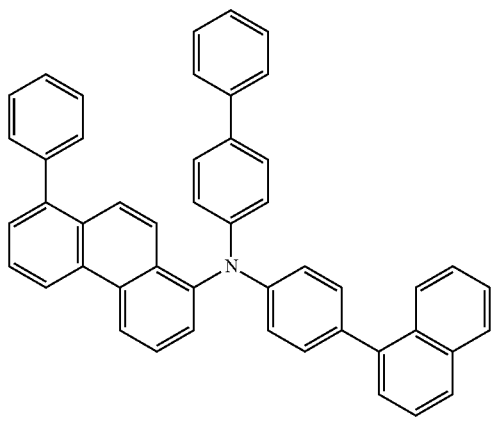
25
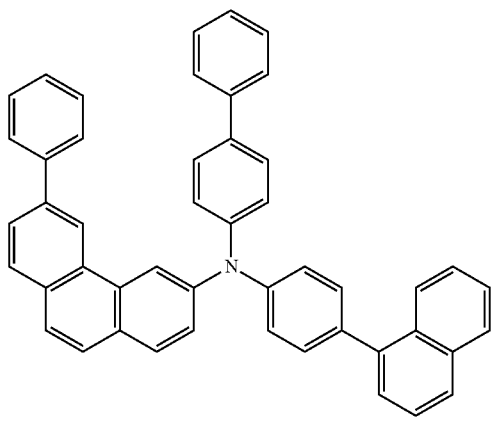
57
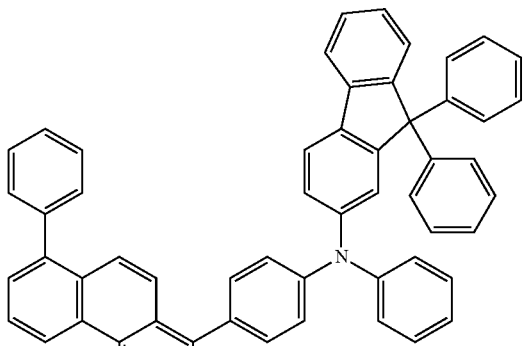
69
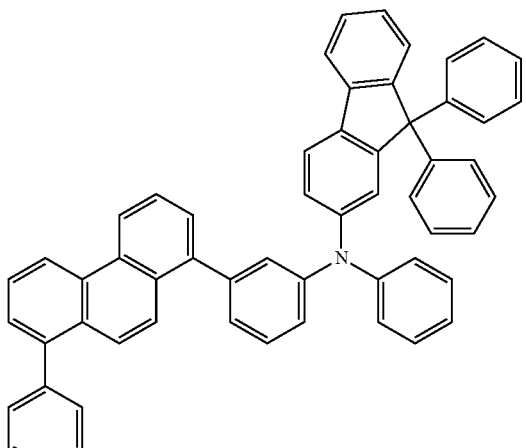
73
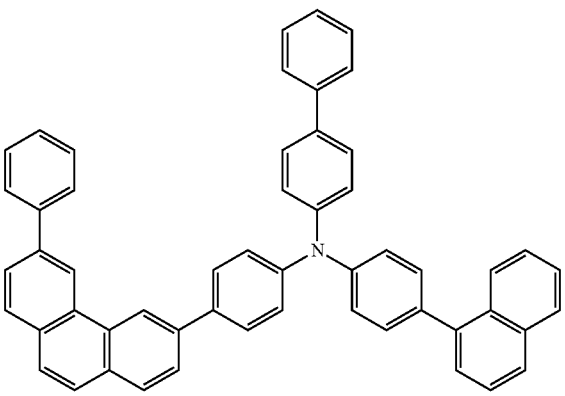
Using each of Comparative Compounds A-1 to A-8 as a material for an electron blocking layer, organic electroluminescence devices of Comparative Examples 1 to 8 were manufactured.

[Comparative Compounds]
A-1
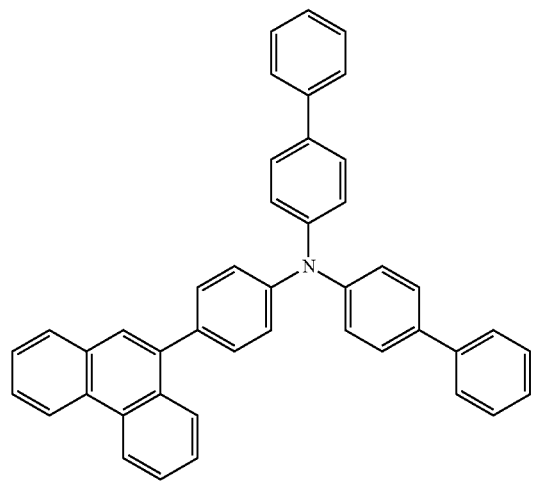
A-2
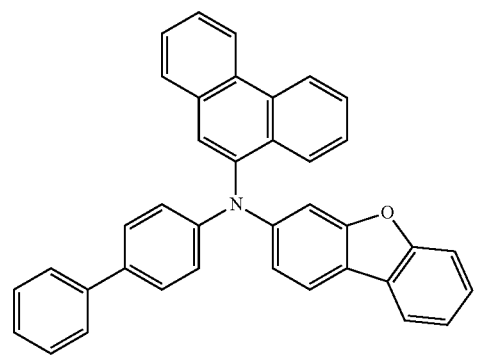
A-3
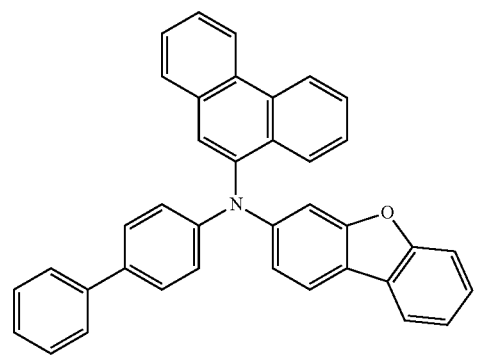
A-4
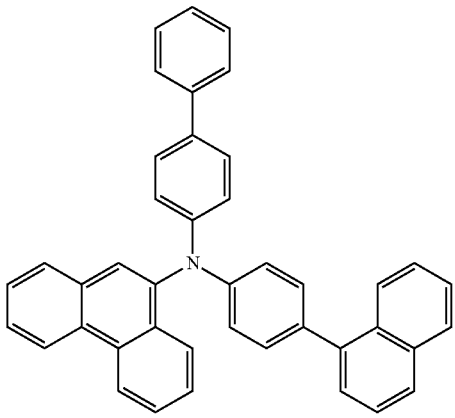
A-5
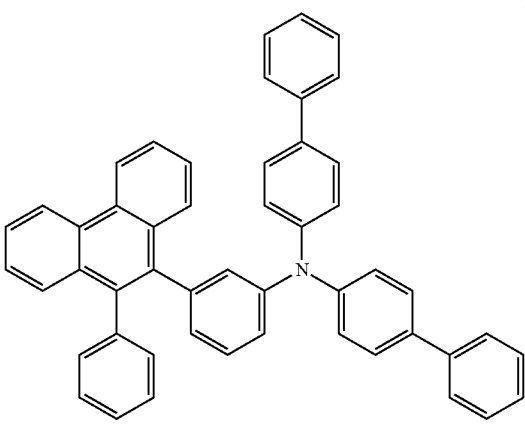
A-6
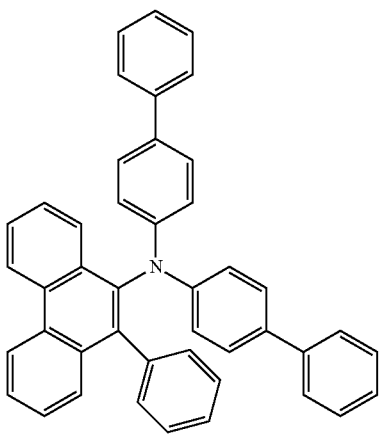

A-7

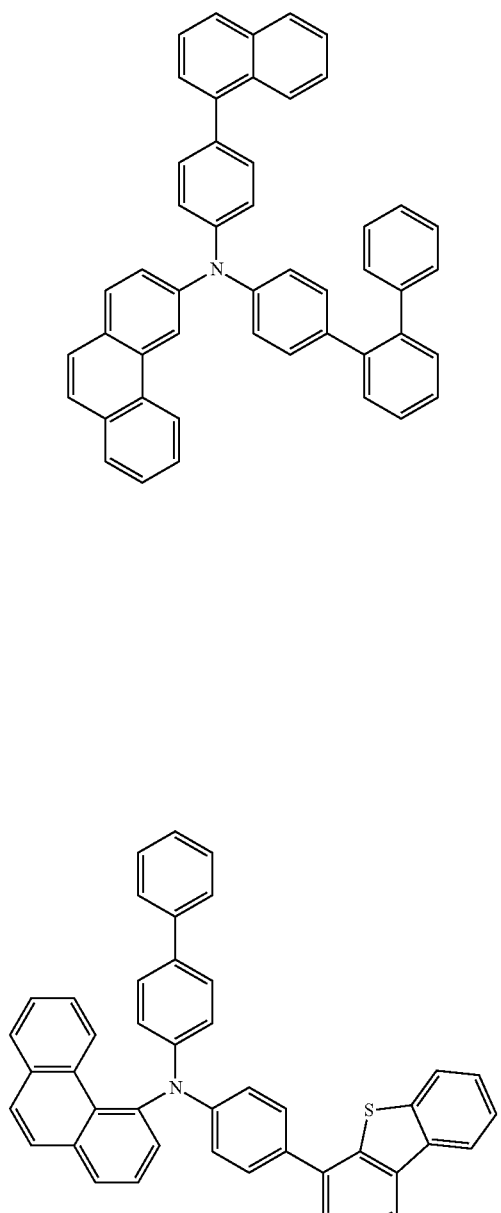

A-8

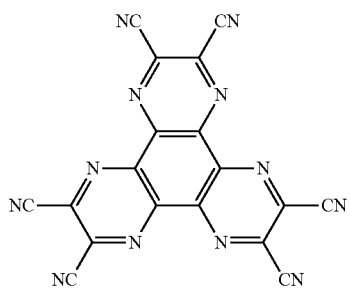
HT2

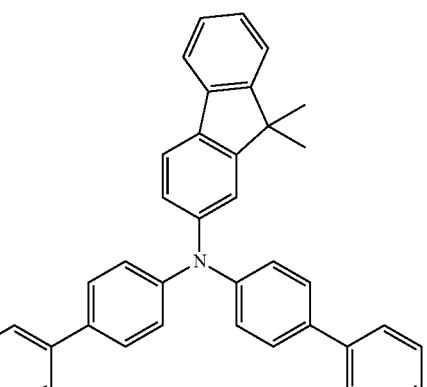
HT1

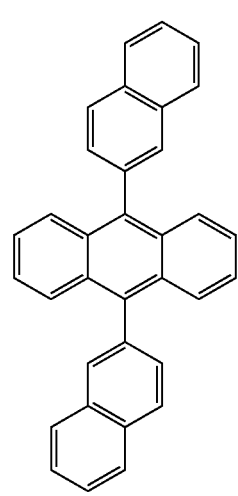
BH

Organic electroluminescence devices of Examples 1 to 6 and Comparative Examples 1 to 8 were manufactured by forming a first electrode using ITO to a thickness of about 150 nm, a hole injection layer using HT1 doped with 10% HT2 to a thickness of about 10 nm, a hole transport layer using HT1 to a thickness of about 120 nm, an electron blocking layer using each of the example compounds or the comparative compounds to a thickness of about 10 nm, an emission layer using BH doped with 2% BD to a thickness of about 30 nm, a hole blocking layer using ET1 to a thickness of about 10 nm, an electron transport layer using ET2 to a thickness of about 20 nm, an electron injection layer using LiF to a thickness of about 1 nm, and a second electrode by co-depositing magnesium (Mg) and silver (Ag) in a ratio of 9:1 (volume ratio) to a thickness of about 120 nm. Each layer was formed by a vacuum deposition method.

-continued

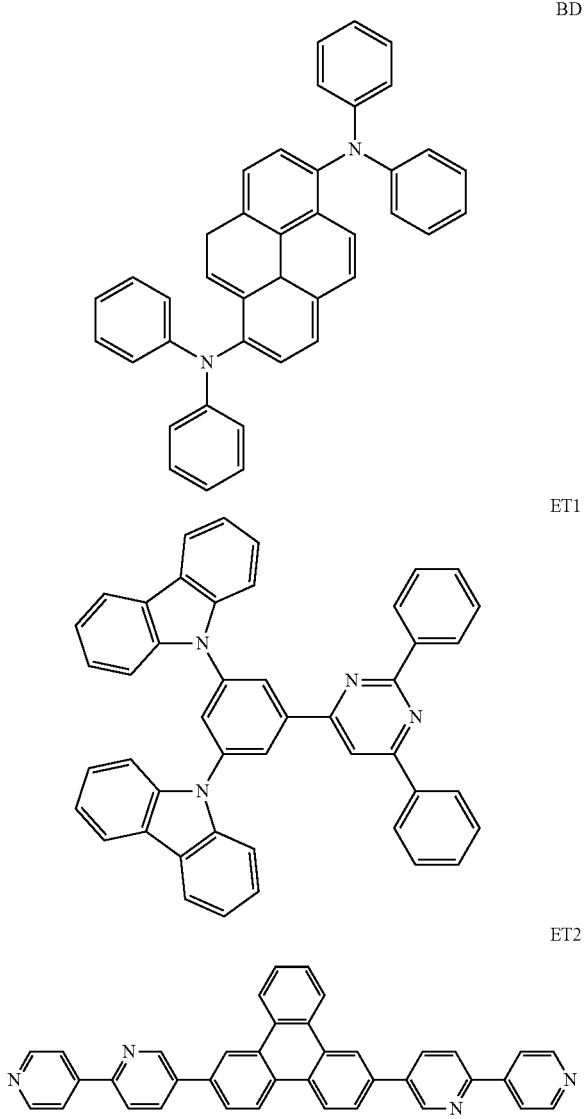

The voltage, half life, emission efficiency, and color coordinate of each of the organic electroluminescence devices according to Examples 1 to 6 and Comparative Examples 1 to 8 are listed in Table 1 below.

TABLE 1

| | Electron blocking layer | Voltage (V) | Life LT50 (h) | Emission efficiency (cd/A) | Color coordinate CIE (x, y) |
|---|---|---|---|---|---|
| Example 1 | Example Compound 11 | 4.5 | 196 | 5.0 | 0.140, 0.051 |
| Example 2 | Example Compound 13 | 4.7 | 189 | 5.4 | 0.142, 0.051 |
| Example 3 | Example Compound 25 | 4.5 | 182 | 5.0 | 0.140, 0.050 |
| Example 4 | Example Compound 57 | 4.6 | 193 | 5.3 | 0.140, 0.051 |
| Example 5 | Example Compound 69 | 4.8 | 188 | 5.4 | 0.140, 0.050 |
| Example 6 | Example Compound 73 | 4.5 | 192 | 5.1 | 0.140, 0.050 |
| Comparative Example 1 | Comparative Compound A-1 | 4.9 | 163 | 3.9 | 0.140, 0.052 |
| Comparative Example 2 | Comparative Compound A-2 | 4.9 | 160 | 3.8 | 0.141, 0.051 |
| Comparative Example 3 | Comparative Compound A-3 | 4.8 | 164 | 3.9 | 0.141, 0.052 |
| Comparative Example 4 | Comparative Compound A-4 | 5.1 | 161 | 4.0 | 0.140, 0.051 |
| Comparative Example 5 | Comparative Compound A-5 | 4.8 | 163 | 4.1 | 0.140, 0.050 |
| Comparative Example 6 | Comparative Compound A-6 | 5.1 | 160 | 4.1 | 0.141, 0.051 |
| Comparative Example 7 | Comparative Compound A-7 | 4.9 | 163 | 4.0 | 0.140, 0.050 |
| Comparative Example 8 | Comparative Compound A-8 | 5.0 | 161 | 3.9 | 0.141, 0.051 |

The emission efficiency is a value measured at 10 mA/cm$^2$, and the half life is a value at 1.0 mA/cm$^2$.

Referring to Table 1, Examples 1 to 6 unexpectedly showed decreased driving voltage, increased life and improved efficiency when compared to Comparative Examples 1 to 8. In Examples 1, 3 and 6, the bond position of a phenanthryl group was 2, 3 and 3, respectively, and amine conjugation was increased to stabilize radical state, thereby increasing life span. Meanwhile, in Examples 2, 4 and 5, the bond position of a phenanthryl group was 1, and the whole volume of a molecule increased, a hole transport degree was controlled to increase the recombination probability of holes and electrons in an emission layer, thereby achieving high efficiency.

In Comparative Examples 1 to 4, 7 and 8, the amine compound included a phenanthryl group, but the phenanthryl group was not substituted with a phenyl group, and charge tolerance was insufficient and molecular stacking was promoted to facilitate crystallization, thereby resulting in decreased device life and emission efficiency. In Comparative Examples 5 and 6, a phenanthryl group was substituted with a phenyl group, but the substitution position of the phenanthryl group was different from the position of the phenanthryl group in the exemplary embodiments, and the molecular volume was large. Thus, the decomposition of the amine compound was easy and the device life was short.

The monoamine compound according to an exemplary embodiment of the invention is used in a hole transport region and contributes to the low driving voltage, high efficiency and long life of an organic electroluminescence device.

The organic electroluminescence device according to an exemplary embodiment of the invention has excellent efficiency.

The organic electroluminescence device according to an exemplary embodiment of the invention has long life.

The monoamine compound according to an exemplary embodiment of the invention may be used as a material for a hole transport region of an organic electroluminescence device and may contribute to the increase of the efficiency and the life of the organic electroluminescence device.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

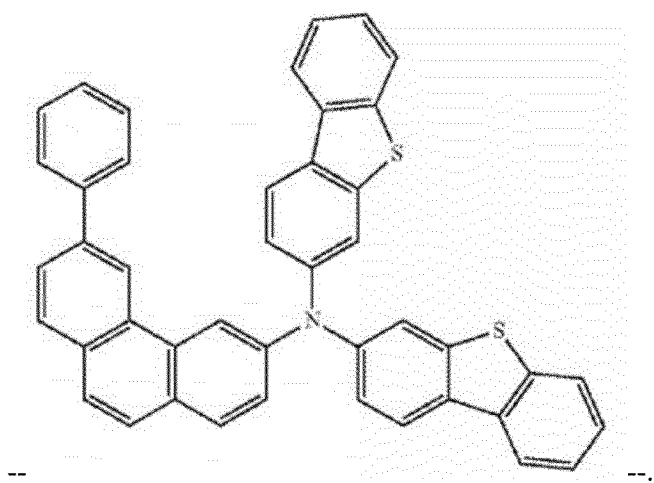

What is claimed is:

1. An organic electroluminescence device, comprising:
a first electrode;
a hole transport region disposed on the first electrode;
an emission layer disposed on the hole transport region;
an electron transport region disposed on the emission layer; and
a second electrode disposed on the electron transport region,
wherein the first electrode and the second electrode each independently comprises at least one material selected from the group consisting of Ag, Mg, Cu, Al, Pt, Pd, Au, Ni, Nd, Ir, Cr, Li, Ca, LiF/Ca, LiF/Al, Mo, Ti, In, Sn, and Zn, or a compound of two or more materials selected therefrom, a mixture of two or more materials selected therefrom, or oxides thereof,
wherein the hole transport region comprises a monoamine compound represented by the following Formula 1:

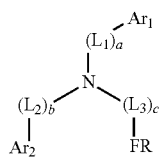

[Formula 1]

wherein in Formula 1,
$L_2$ and $L_3$ are each independently a direct linkage or an unsubstituted arylene group having 6 to 12 carbon atoms for forming a ring,
"b" to "c" are each independently an integer of 0 to 2,
$Ar_2$ is a substituted or unsubstituted aryl group having 6 to 30 carbon atoms for forming a ring, or a substituted or unsubstituted heteroaryl group having 5 to 12 carbon atoms for forming a ring, and
FR is represented by one of the following Formulae 3-1 or 3-3:

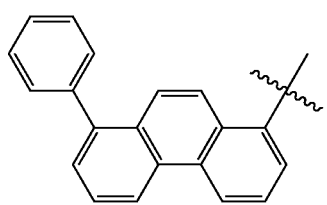

[Formula 3-1]

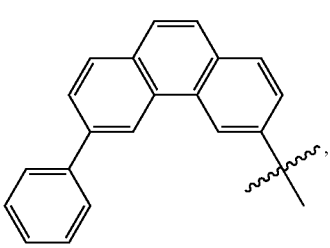

[Formula 3-3]

and $-(L_1)_a-Ar_1$ is represented by one of the following structures:

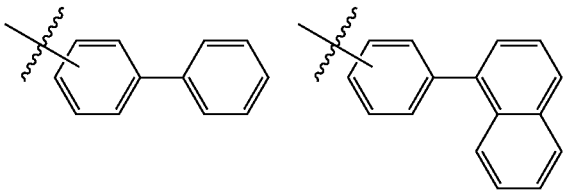

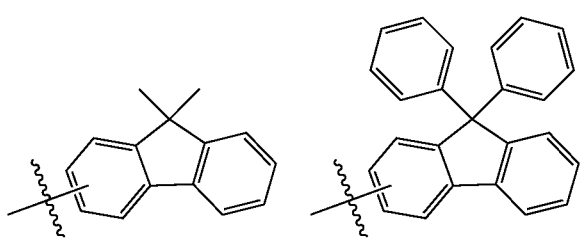

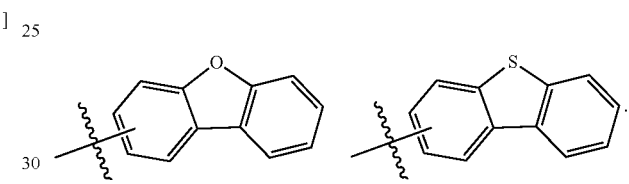

2. The organic electroluminescence device of claim 1, wherein
the hole transport region has a multilayer structure having a plurality of layers, and
a layer making contact with the emission layer among the plurality of layers comprises the monoamine compound represented by Formula 1.

3. The organic electroluminescence device of claim 1, wherein the hole transport region comprises:
a hole injection layer disposed on the first electrode;
a hole transport layer disposed on the hole injection layer; and
an electron blocking layer disposed on the hole transport layer, and
the electron blocking layer comprises the monoamine compound represented by Formula 1.

4. The organic electroluminescence device of claim 1, wherein "c" is 1, and $L_3$ is a substituted or unsubstituted phenylene group, or a substituted or unsubstituted naphthylene group.

5. The organic electroluminescence device of claim 1, wherein the emission layer comprises a pyrene-based compound, and
wherein the electron transport region comprises a triphenylene-based compound.

6. The organic electroluminescence device of claim 1, wherein the monoamine compound represented by Formula 1 is at least one compound selected from compounds represented in the following Compound Group 1 and Compound Group 2:

[Compound Group 1]
13
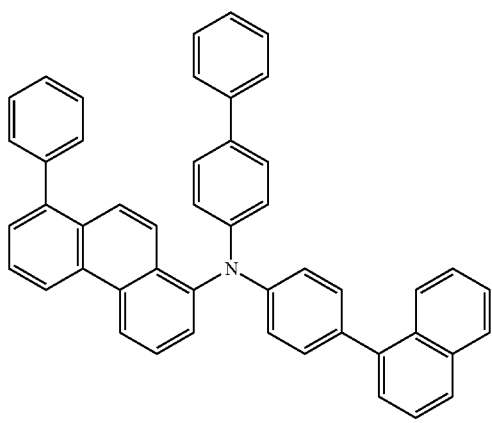
14
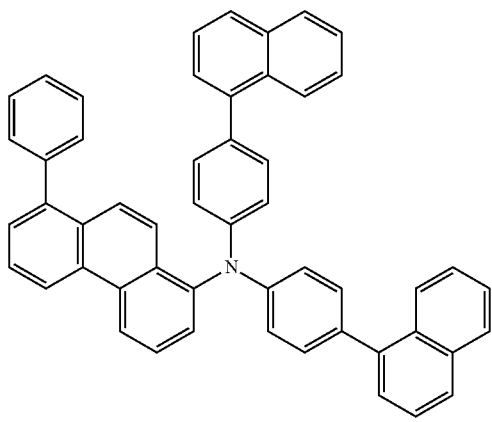
15
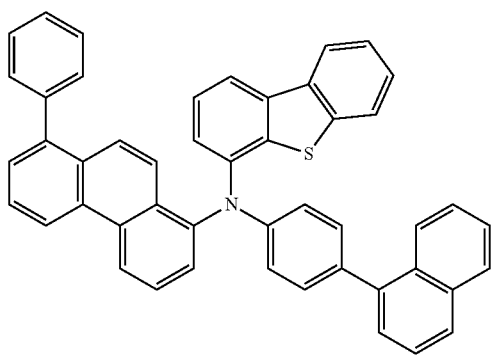
16
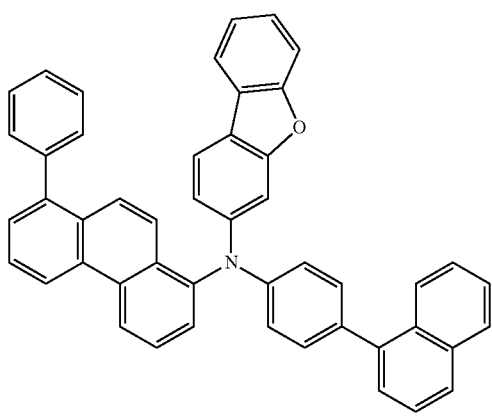
17
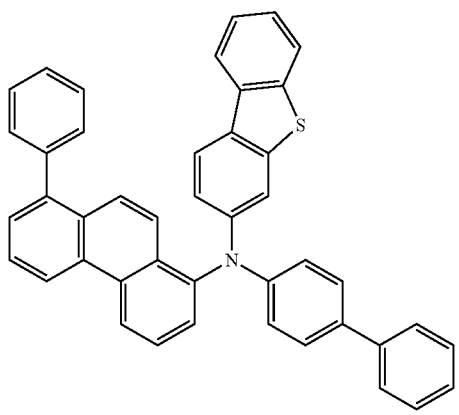
18
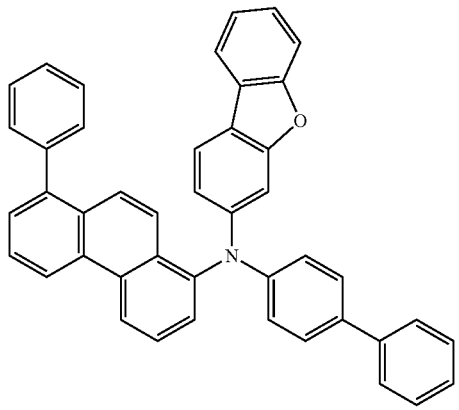
19
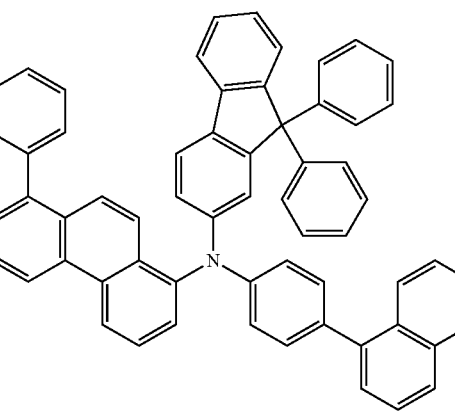
20
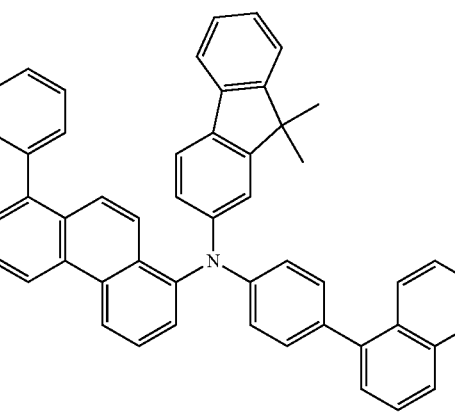

-continued
21
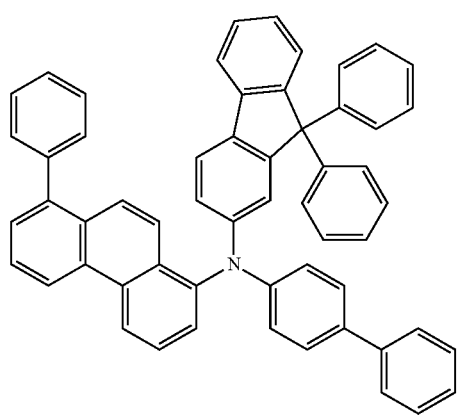
22
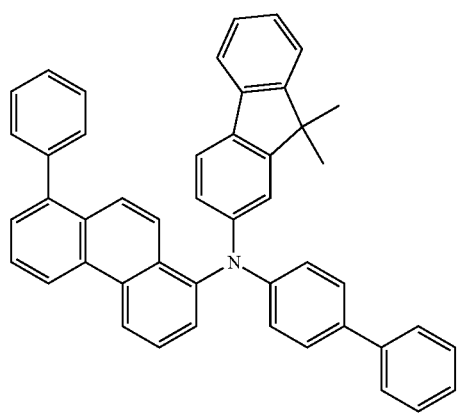
23
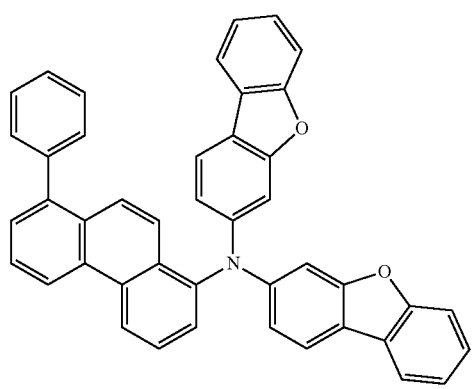
24
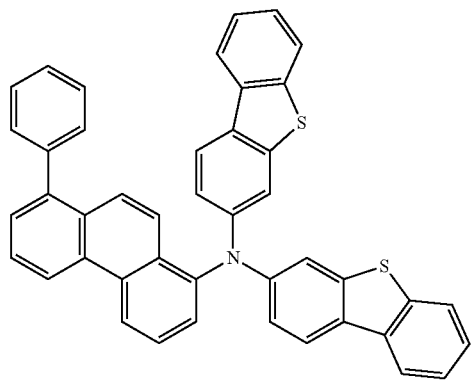
-continued
25
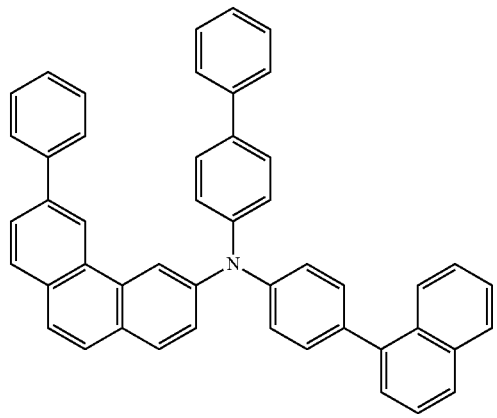
26
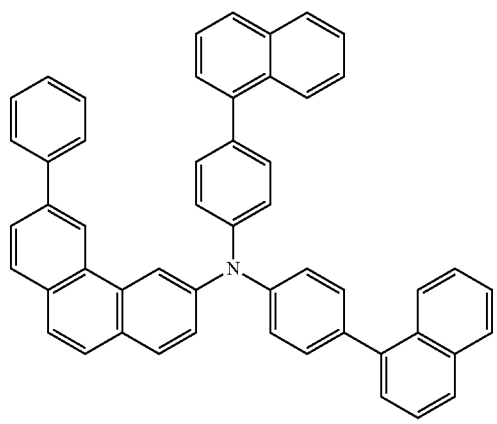
27
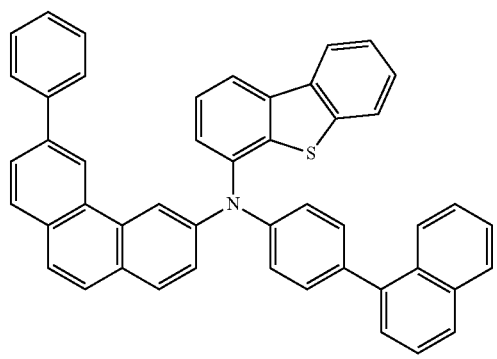
28
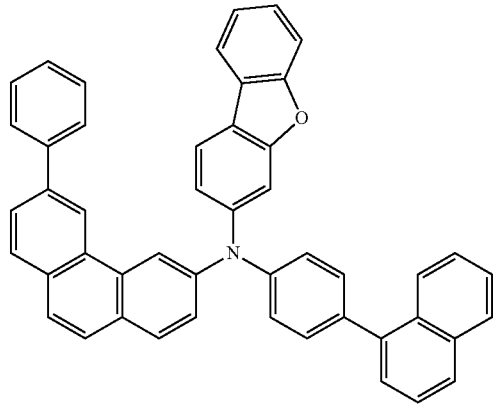

29
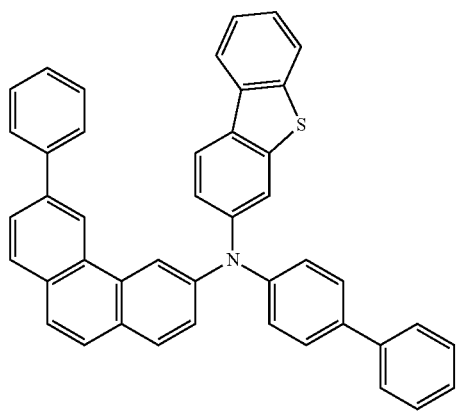
30
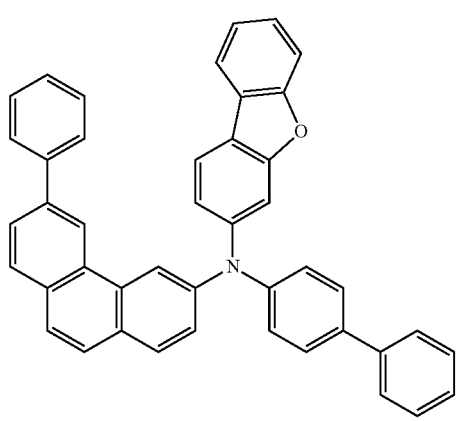
31
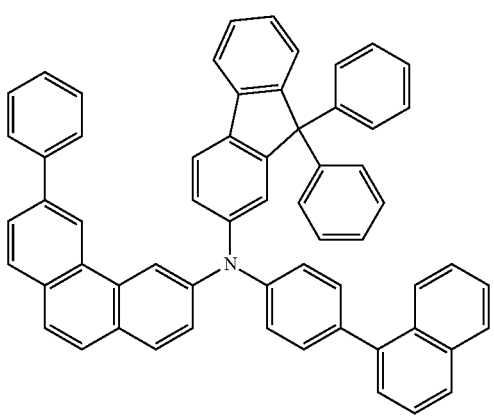
32
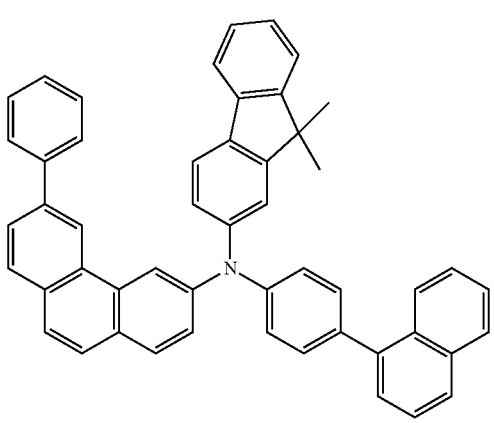
33
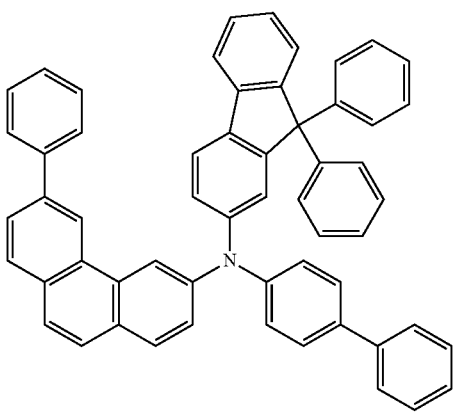
34
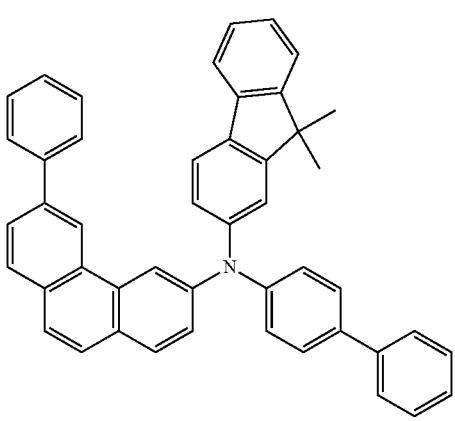
35
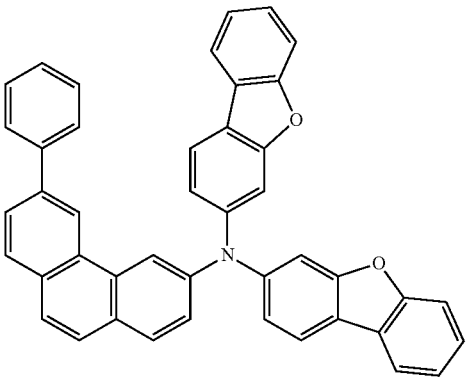
36
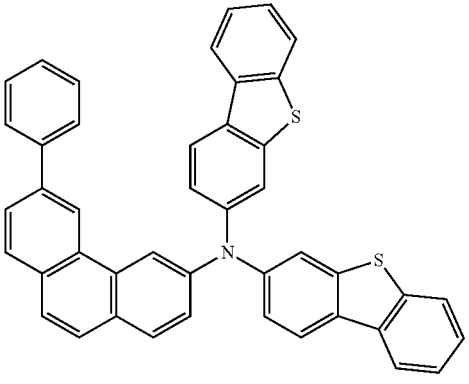

[Compound Group 2]
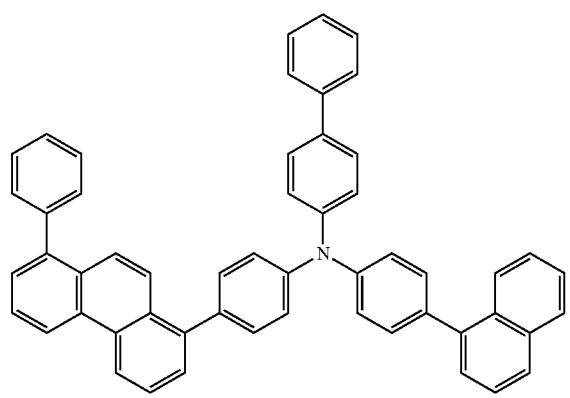
49
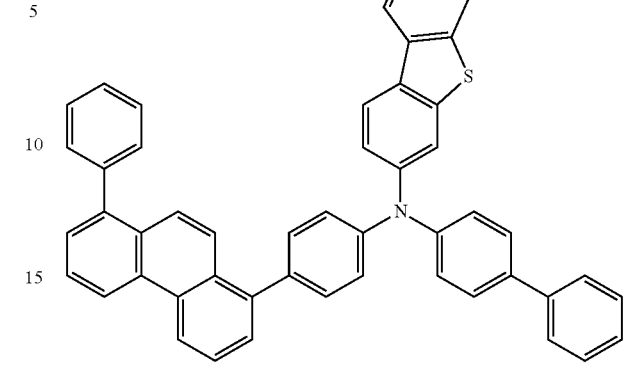
53
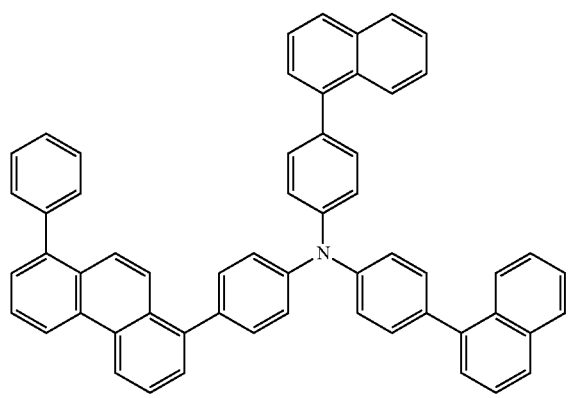
50
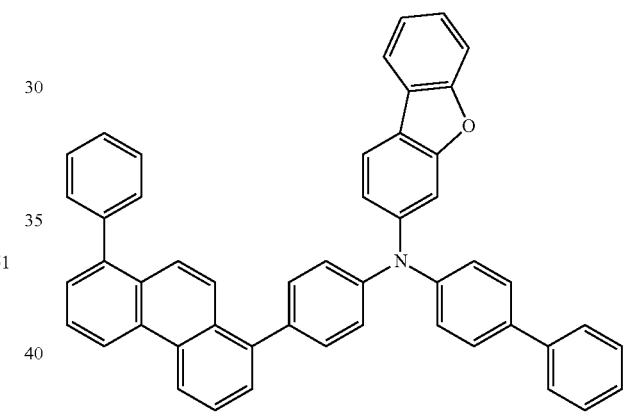
54
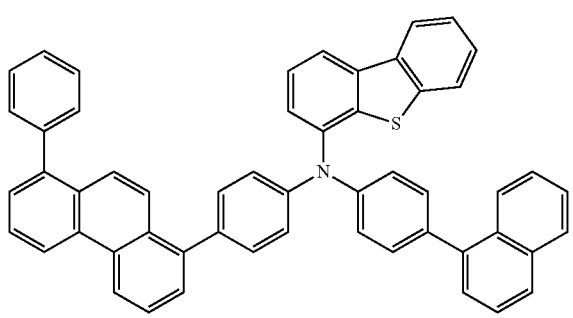
51
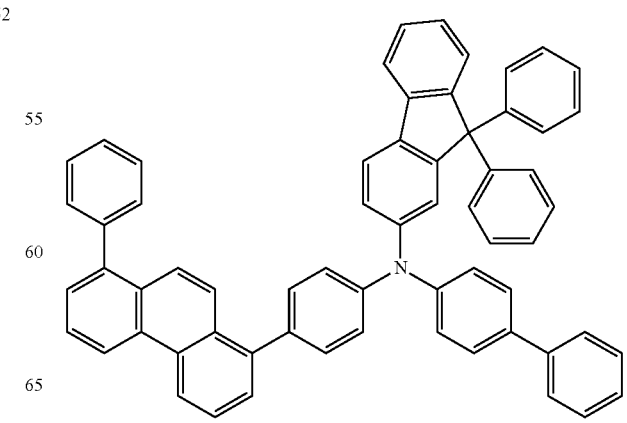
55
52

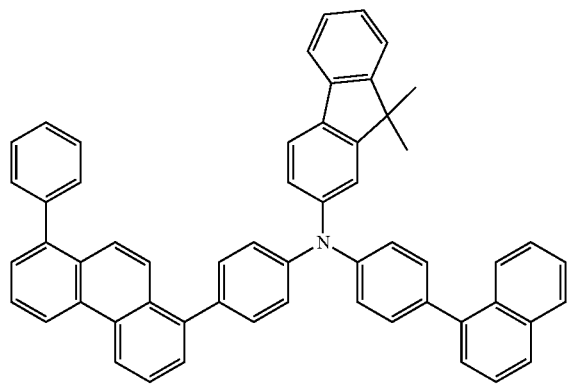
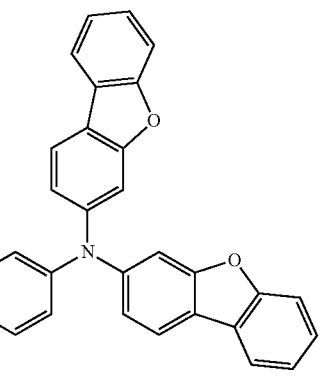
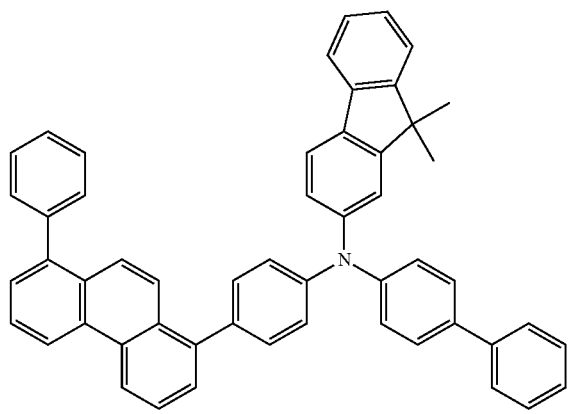
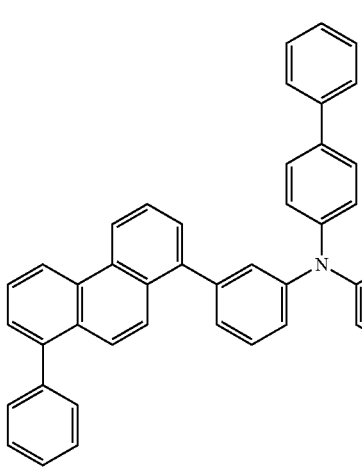

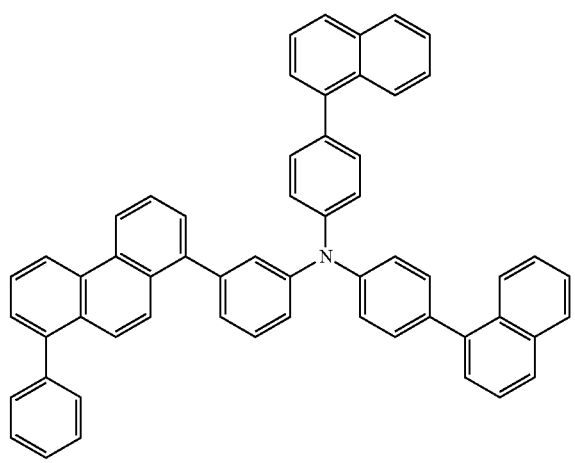
62
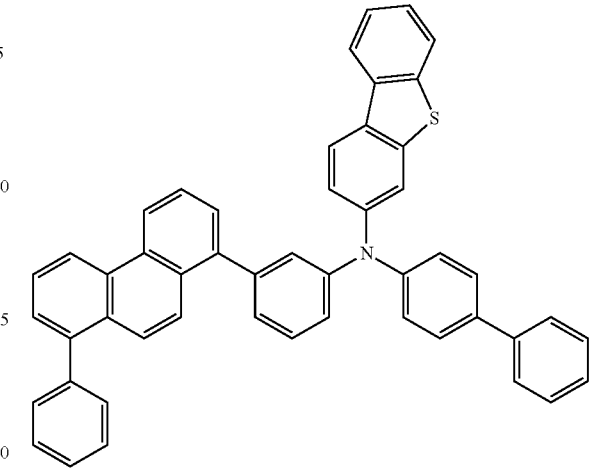
65
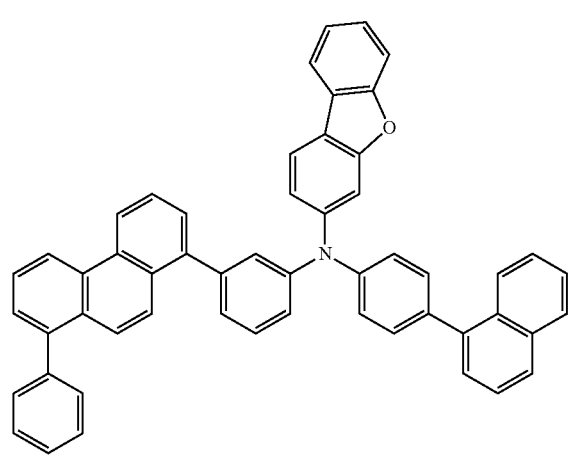
63
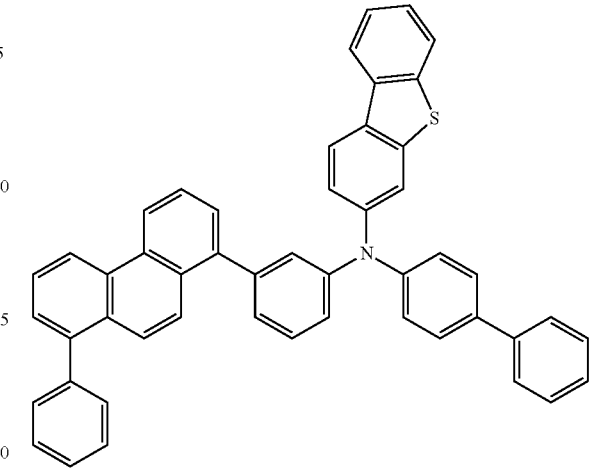
66

68
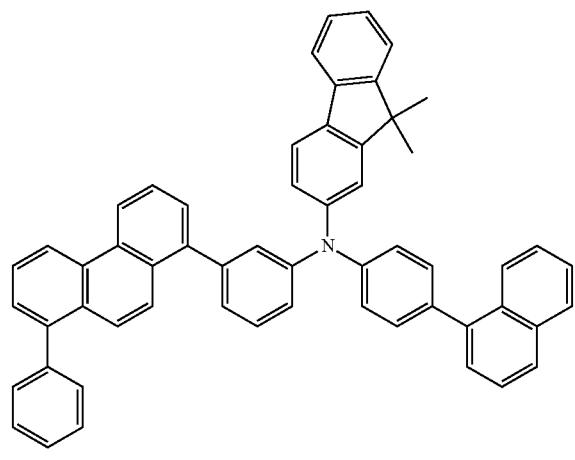
69
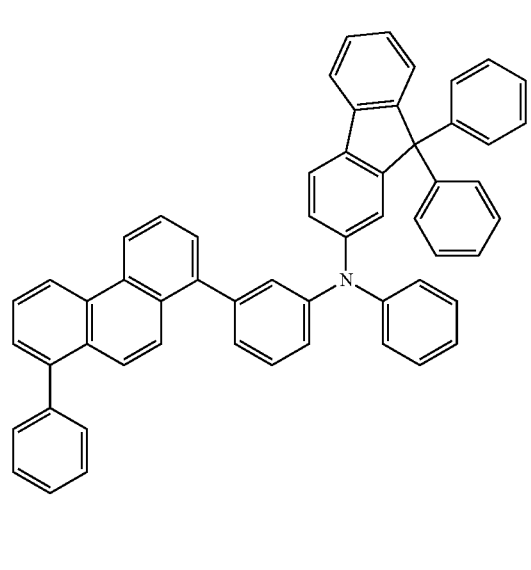
70
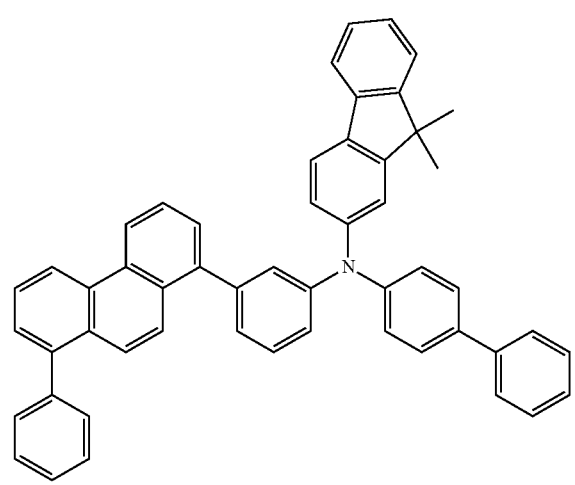
71
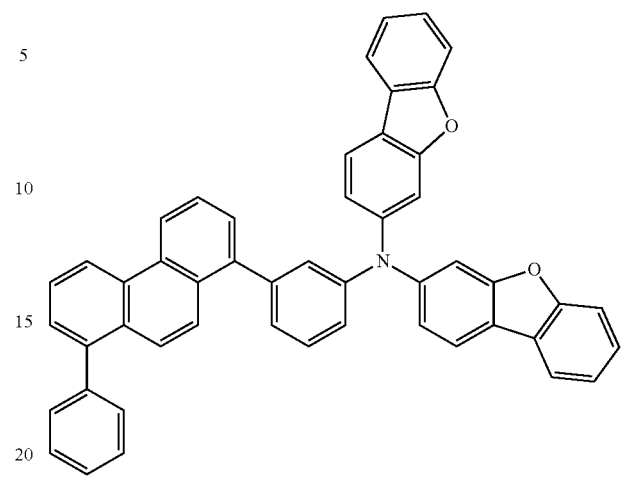
72
73

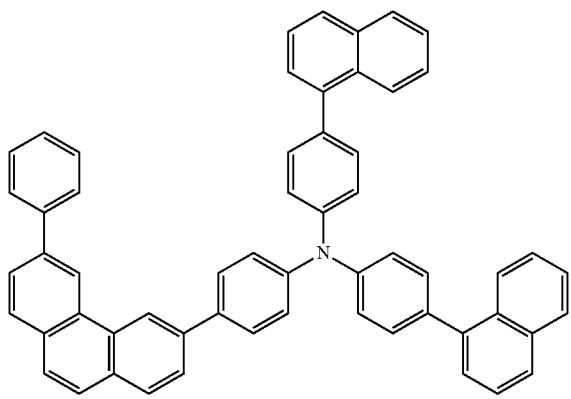
74
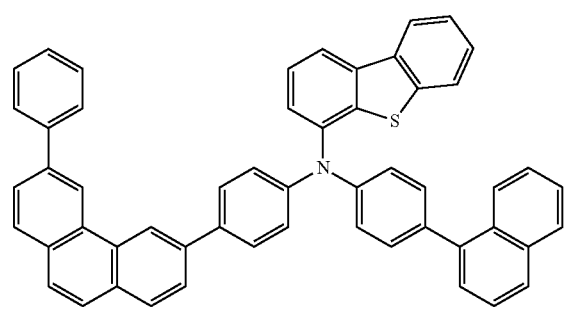
75
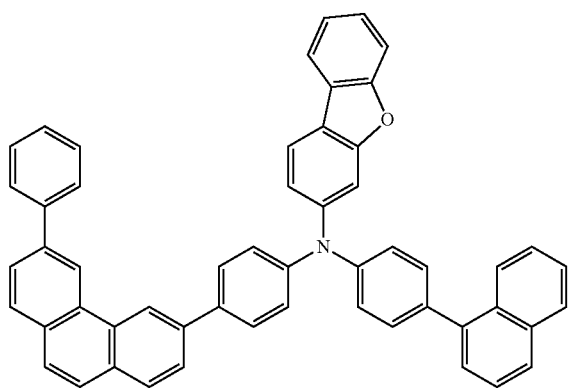
76
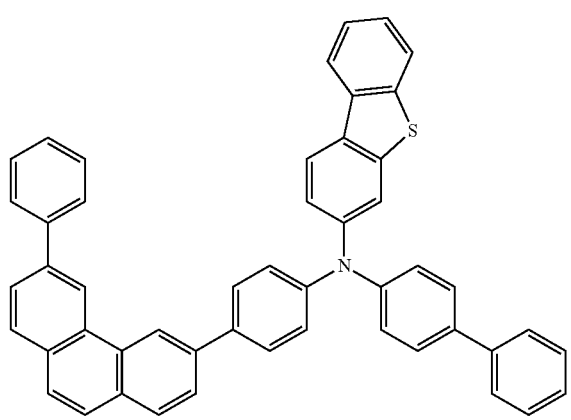
77
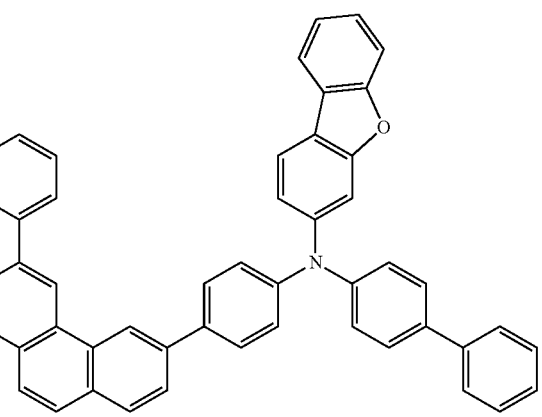
78
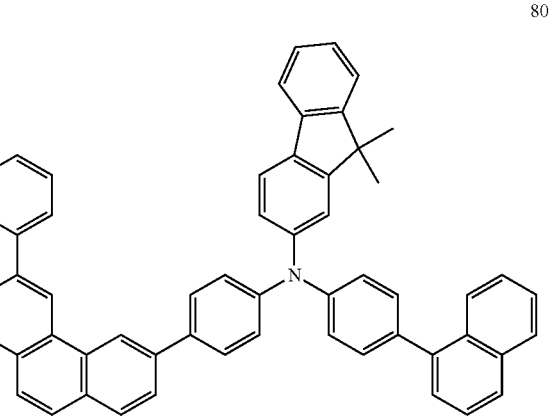
79
80

93
-continued
81
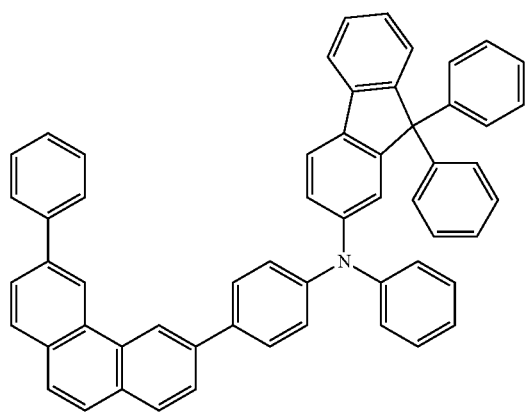
82
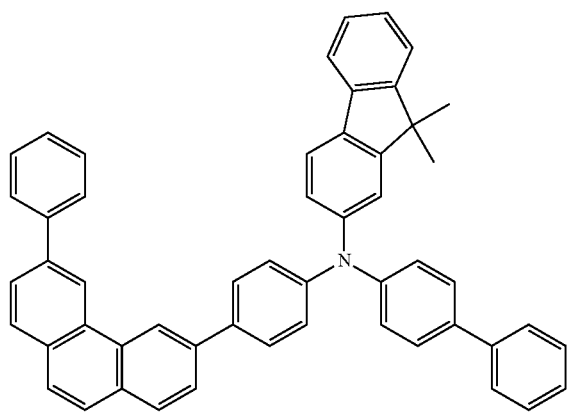
83
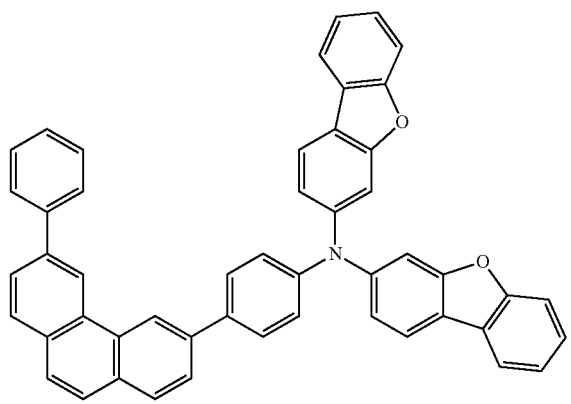
94
-continued
84
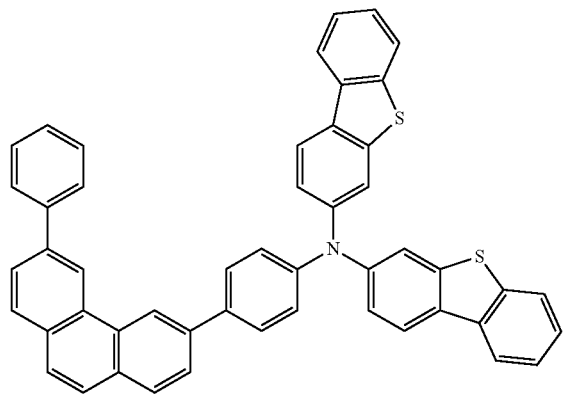
85
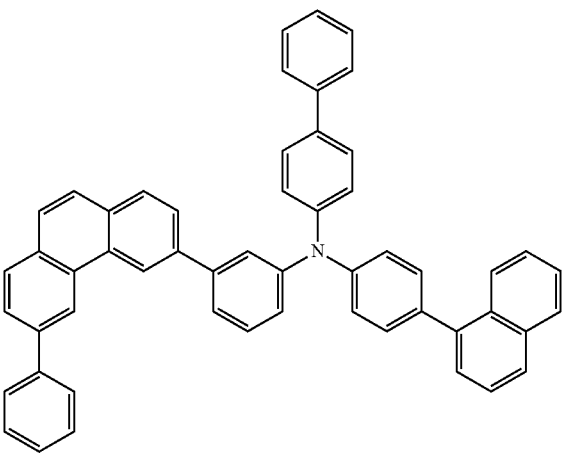
86
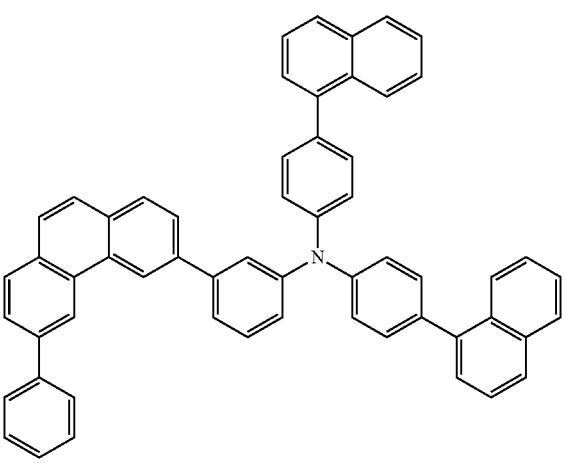

87
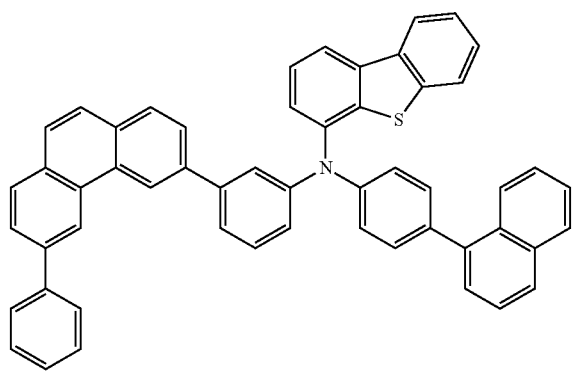
90
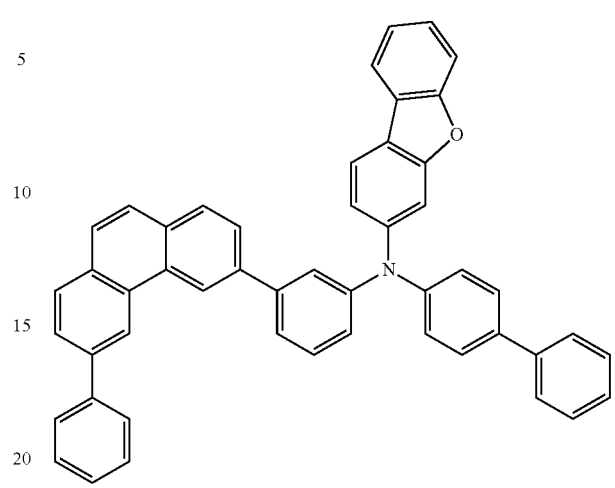
88
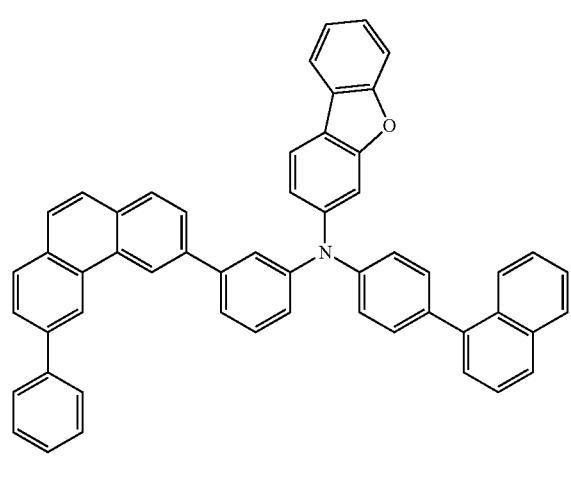
91
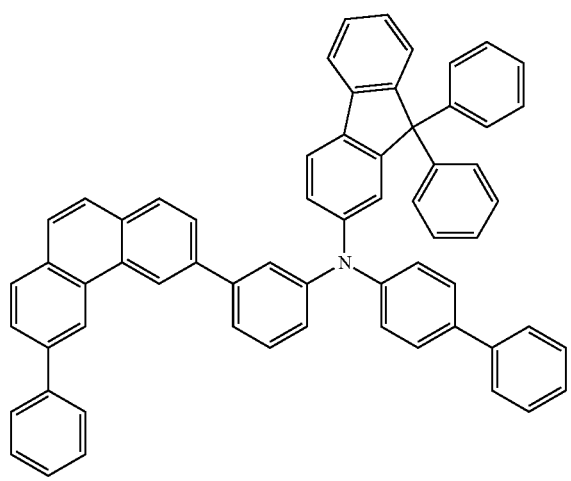
89
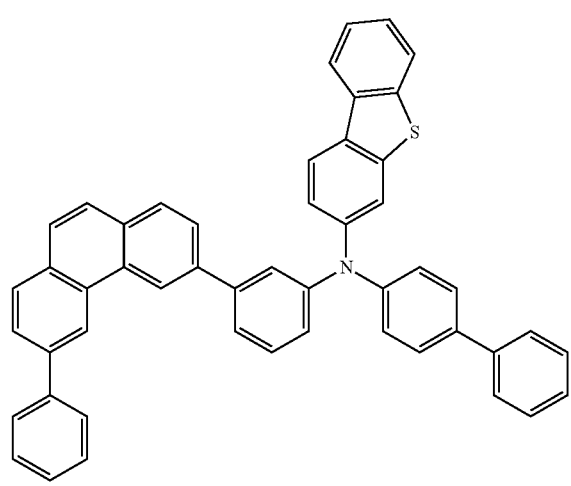
92
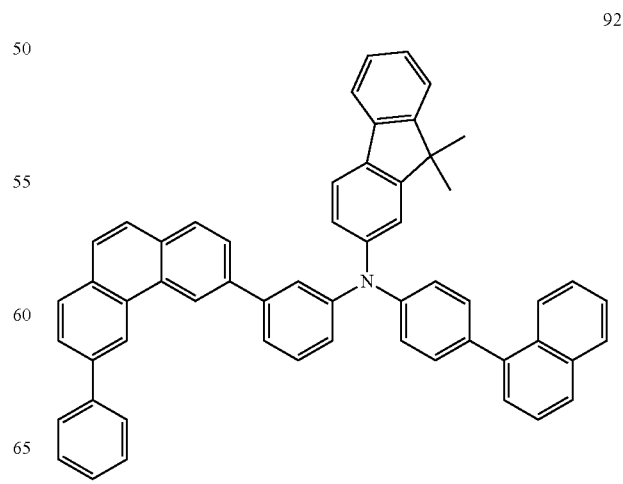

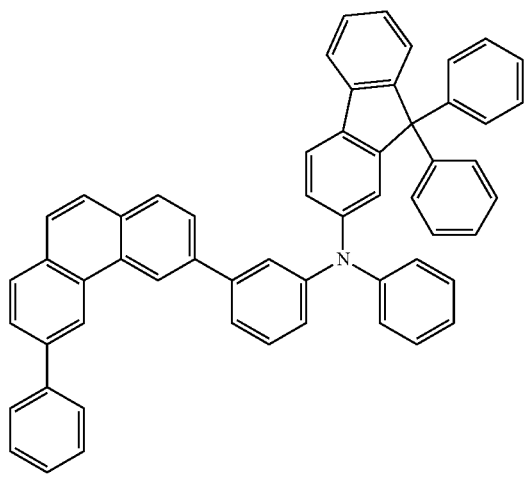

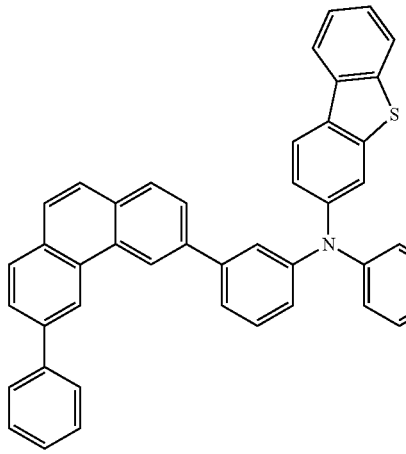

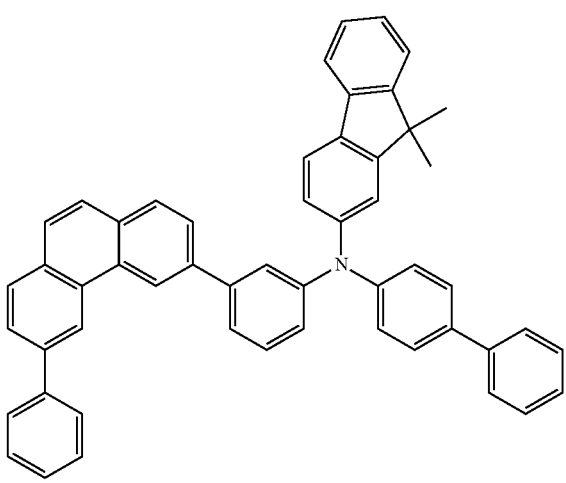

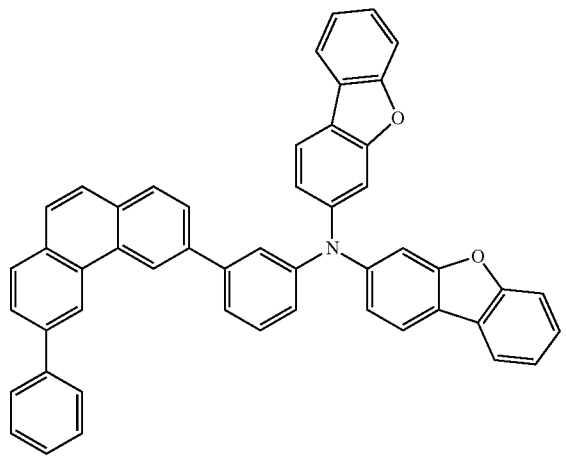

7. A monoamine compound, represented by the following Formula 1:

[Formula 1]

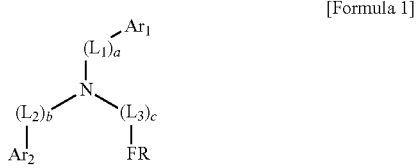

wherein in Formula 1,

L$_2$ and L$_3$ are each independently a direct linkage or an unsubstituted arylene group having 6 to 12 carbon atoms for forming a ring, "b" to "c" are each independently an integer of 0 to 2, Ar$_2$ is a substituted or unsubstituted aryl group having 6 to 30 carbon atoms for forming a ring, or a substituted or unsubstituted heteroaryl group having 5 to 12 carbon atoms for forming a ring, and FR is represented by one of the following Formulae 3-1 or 3-3:

[Formula 3-1]

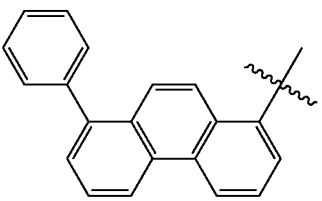

[Formula 3-3]

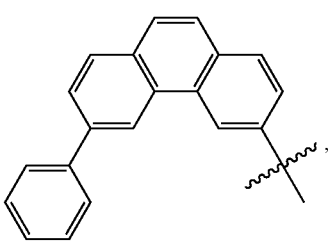

and -$(L_1)_a$-$Ar_1$ is represented by one of the following structures:

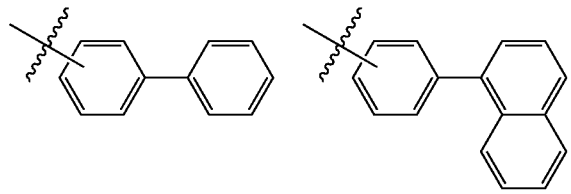

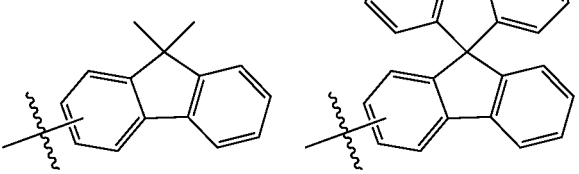

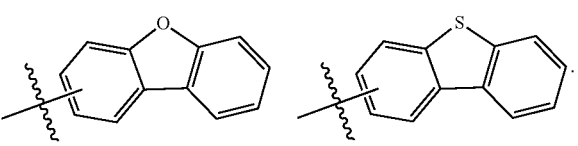

8. The monoamine compound of claim 7, wherein "c" is 1, and $L_3$ is a substituted or unsubstituted phenylene group, or a substituted or unsubstituted naphthylene group.

9. The monoamine compound of claim 7, wherein the monoamine compound represented by Formula 1 is one selected from compounds represented in the following Compound Group 1:

[Compound Group 1]

13

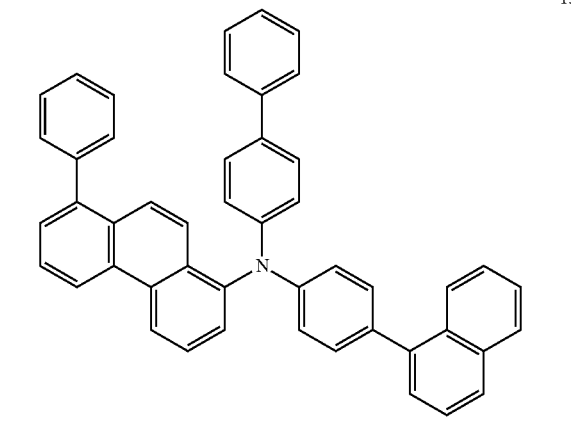

14

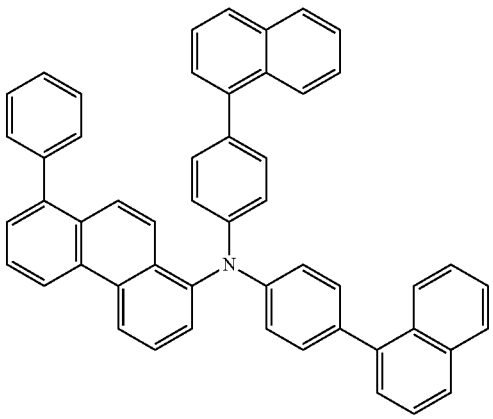

15

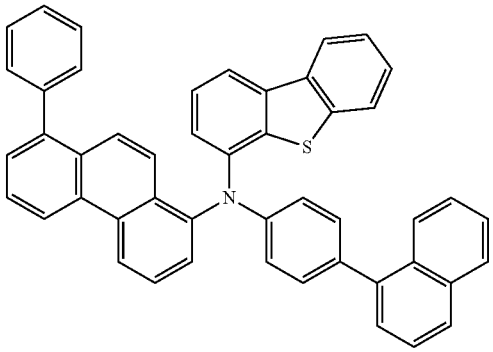

16

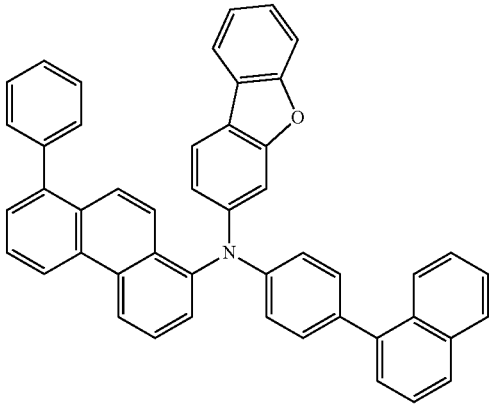

17

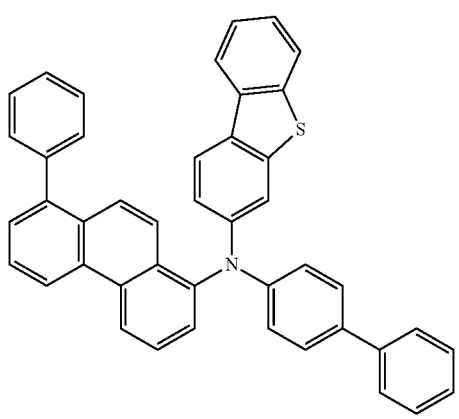

-continued
18
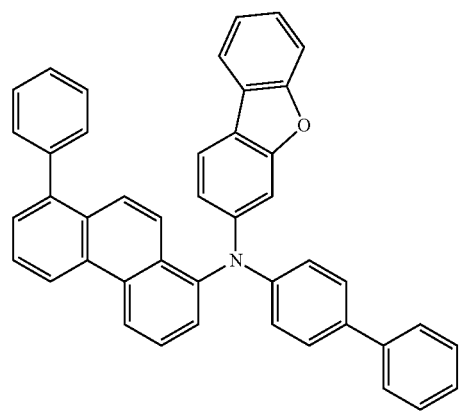
19
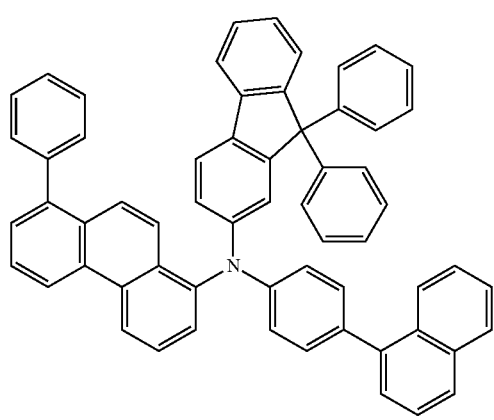
20
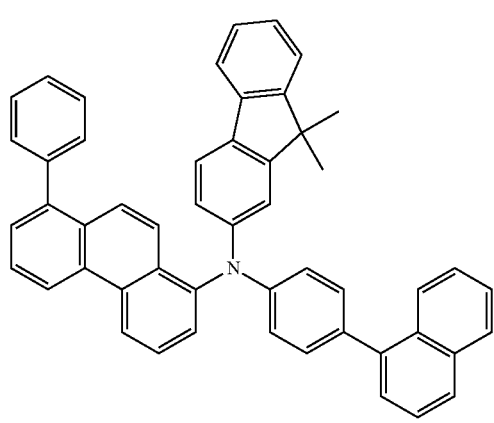
21
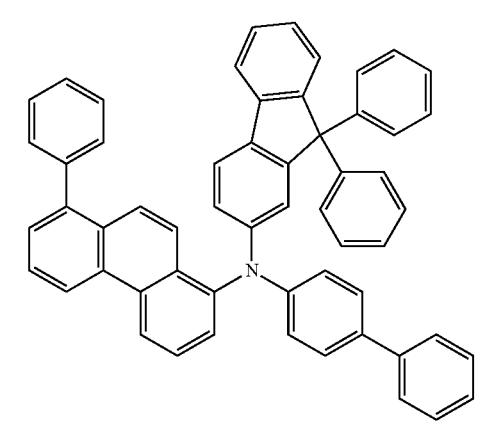
-continued
22
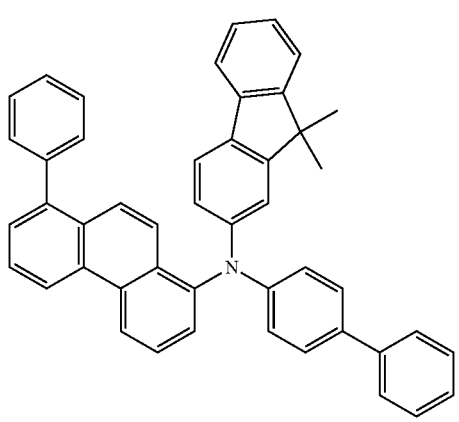
23
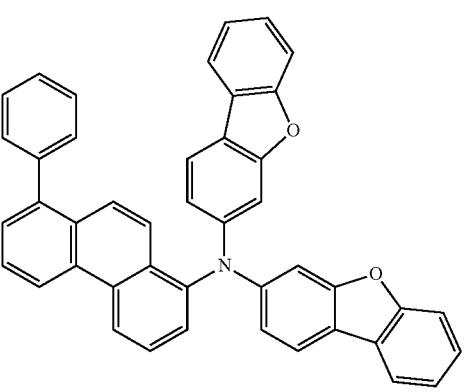
24
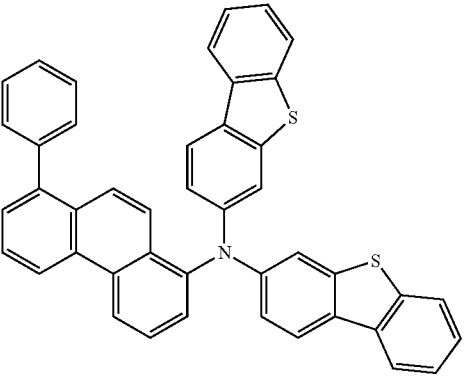
25
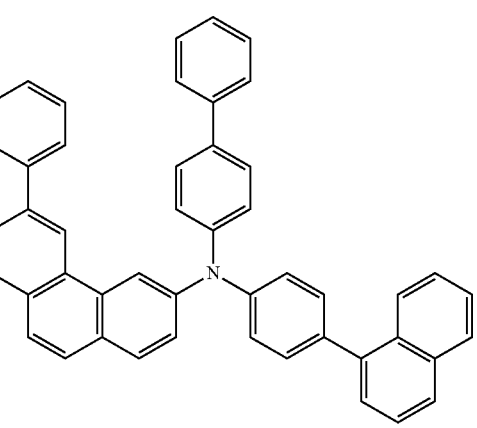

103
-continued
26
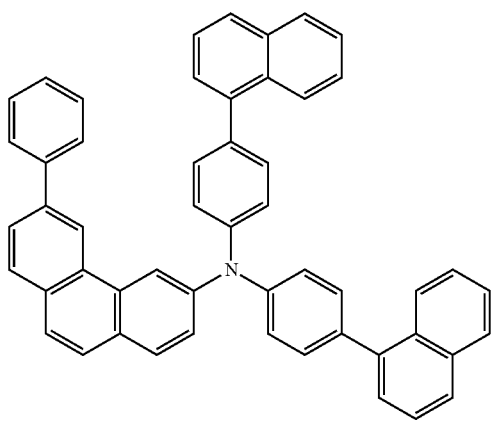
27
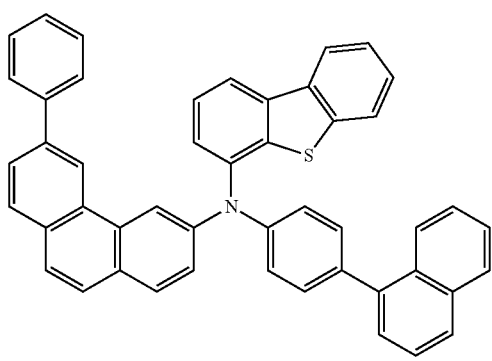
28
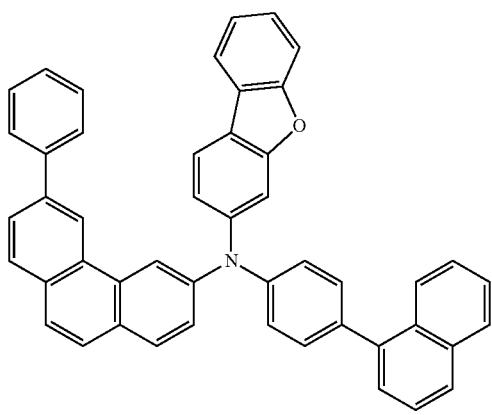
29
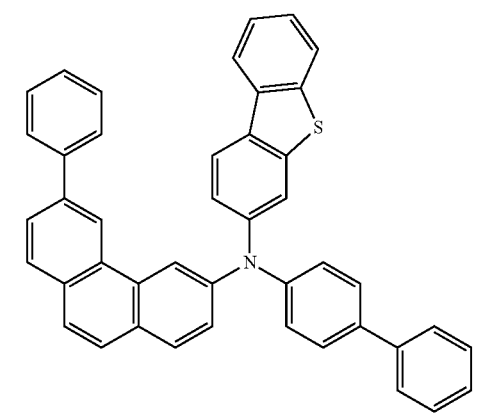
104
-continued
30
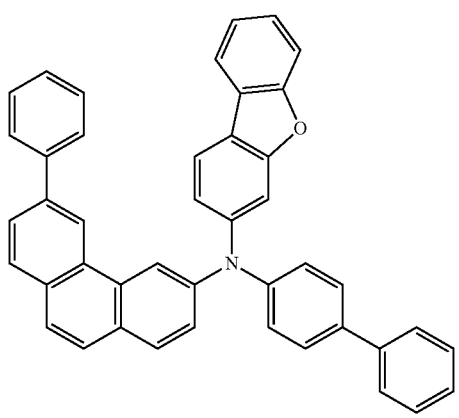
31
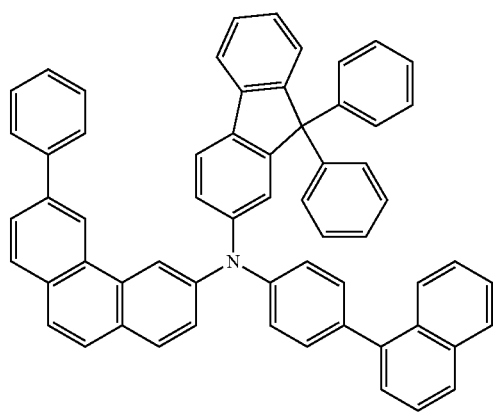
32
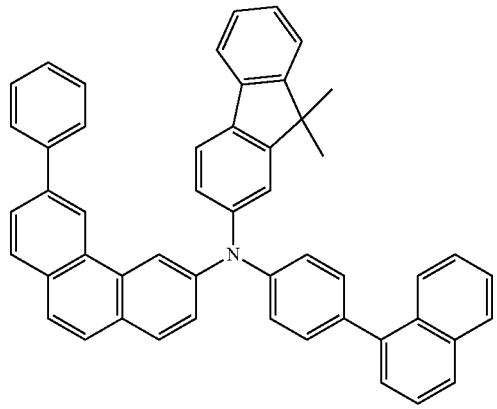
33
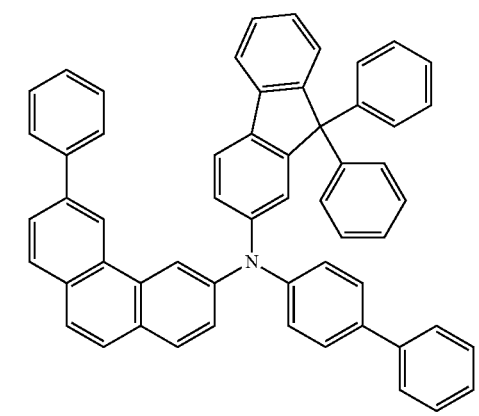

34
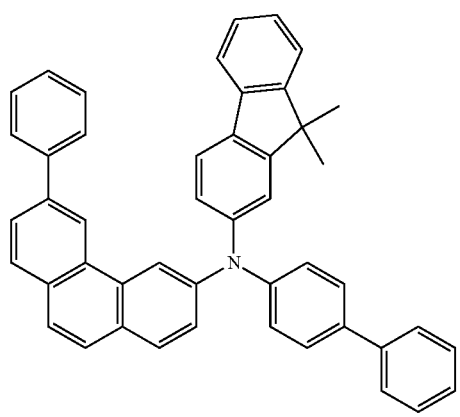
[Compound Group 2]
49
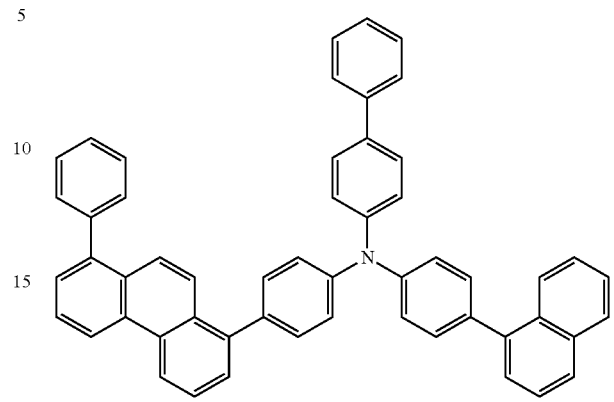
50
35
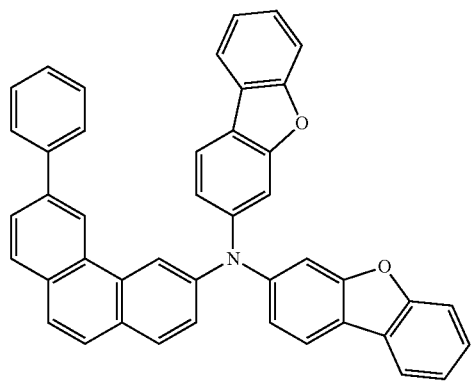
51
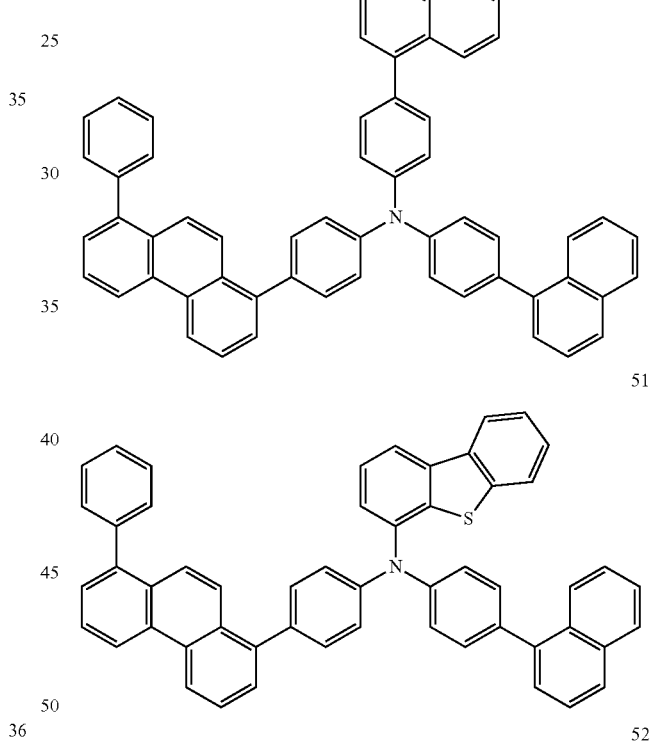
36
52
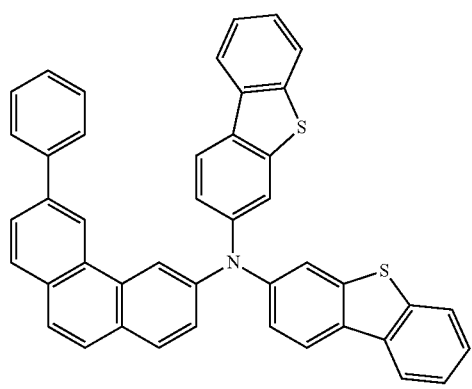
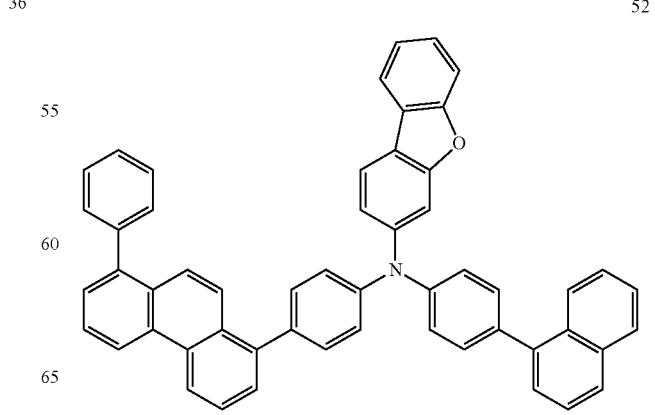

53
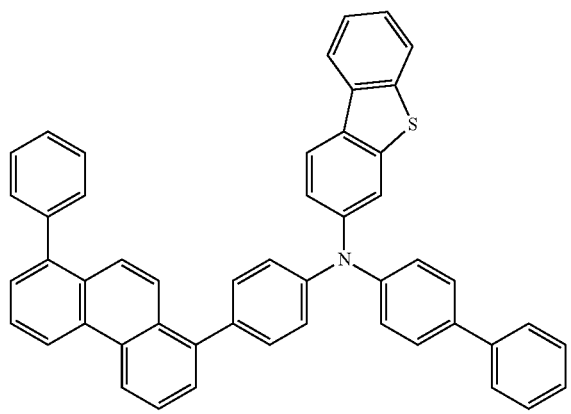
54
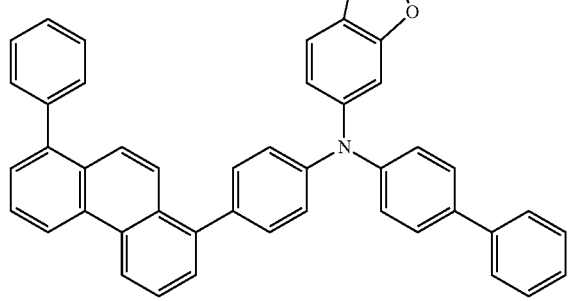
55
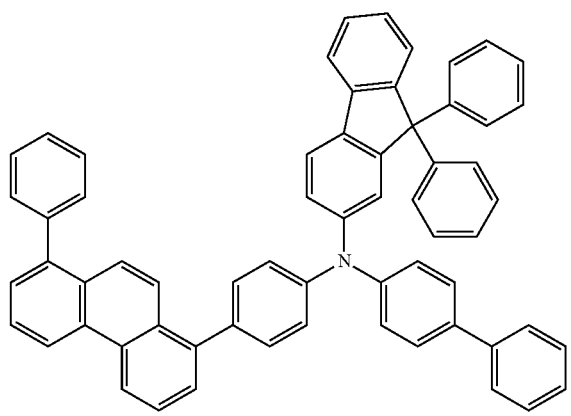
56
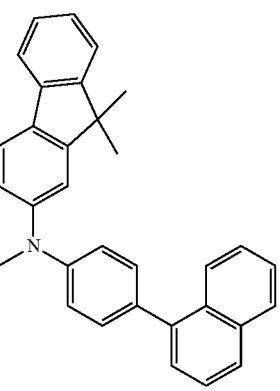
57
58

59
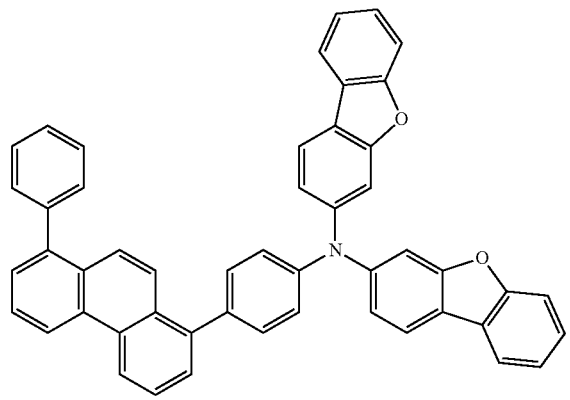
60
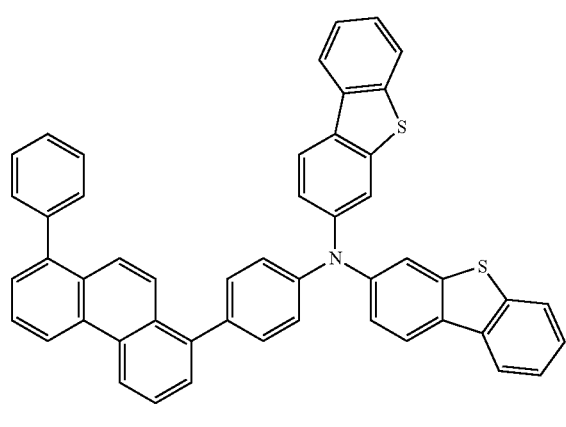
61
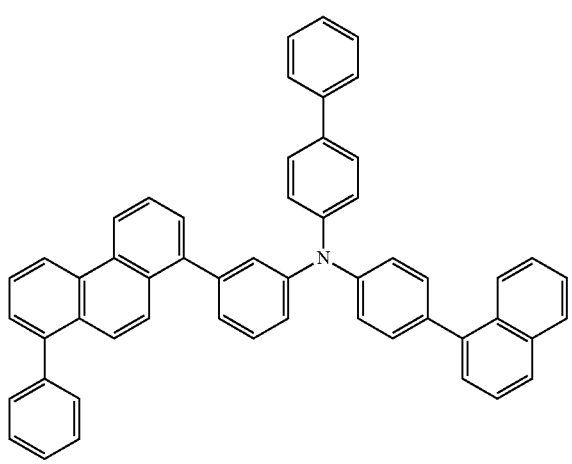
62
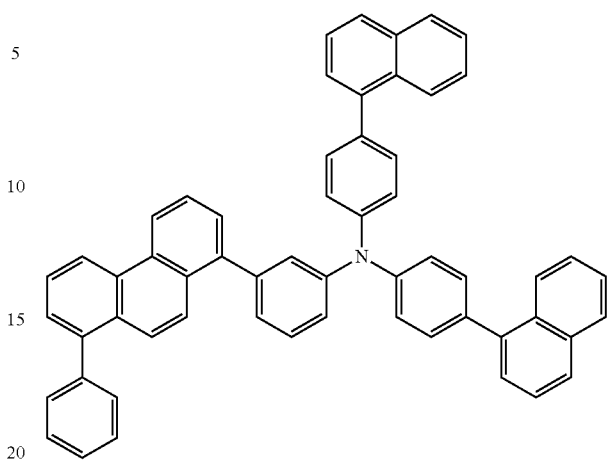
63
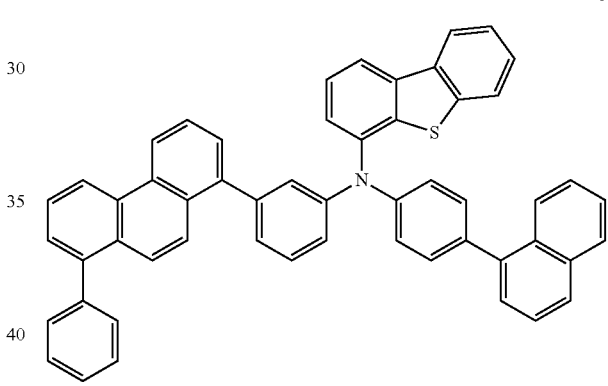
64
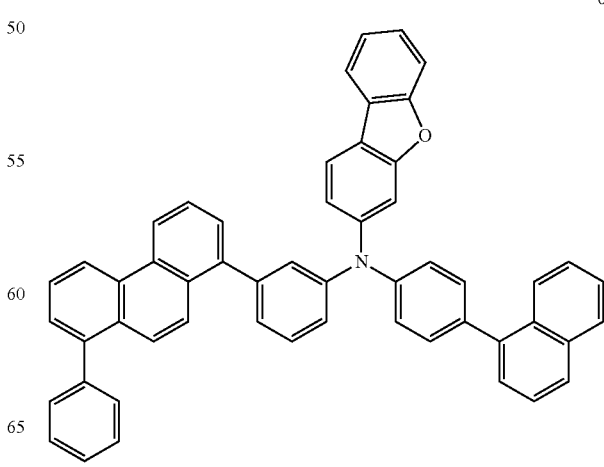

111
-continued
65
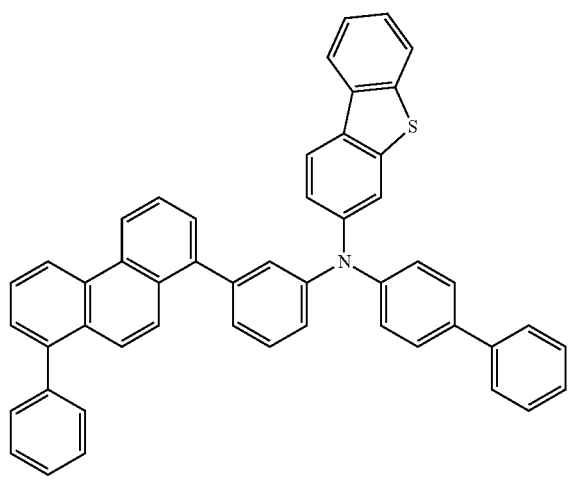
66
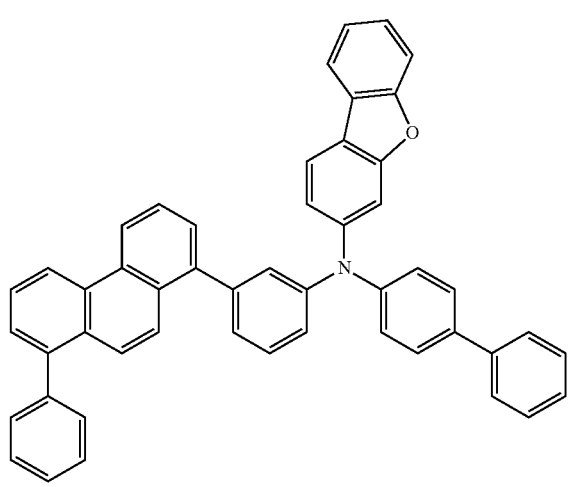
67
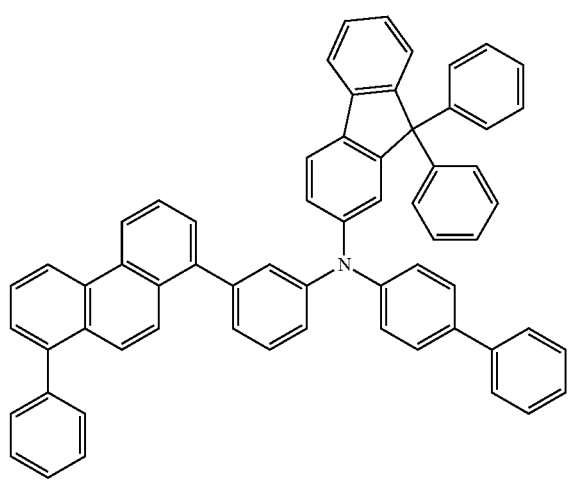
112
-continued
68
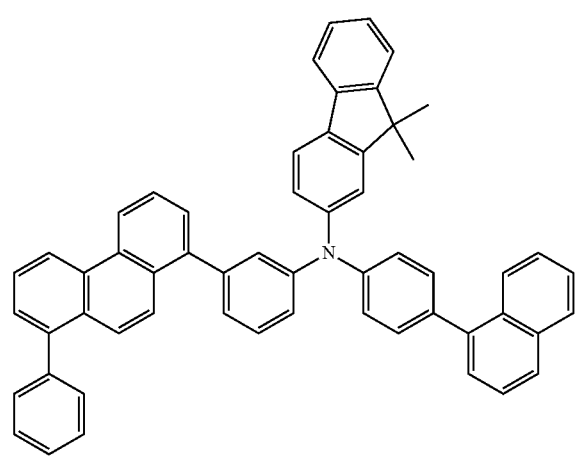
69
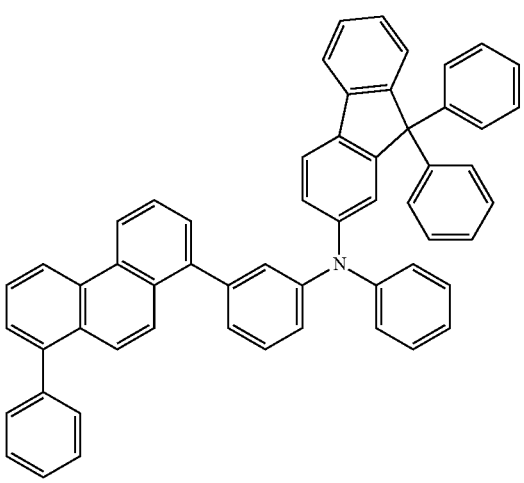
70
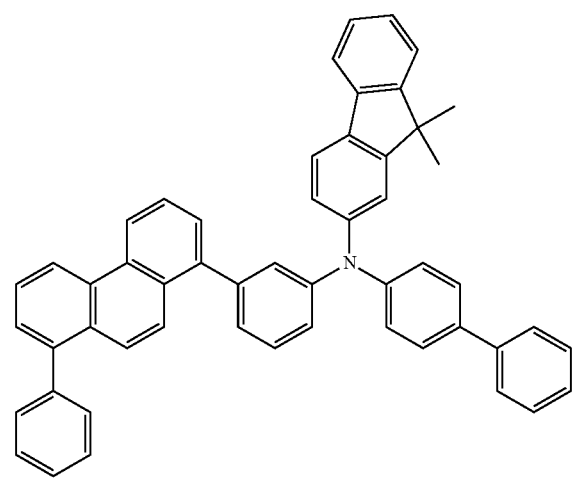

71
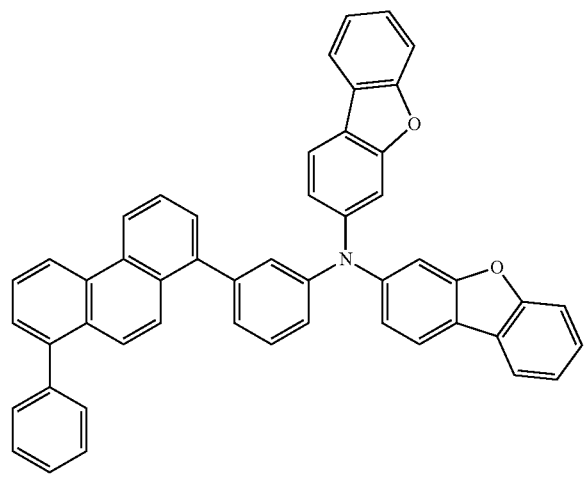
72
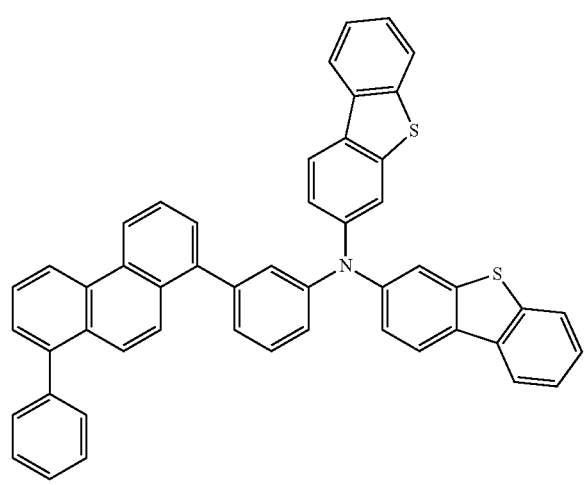
73
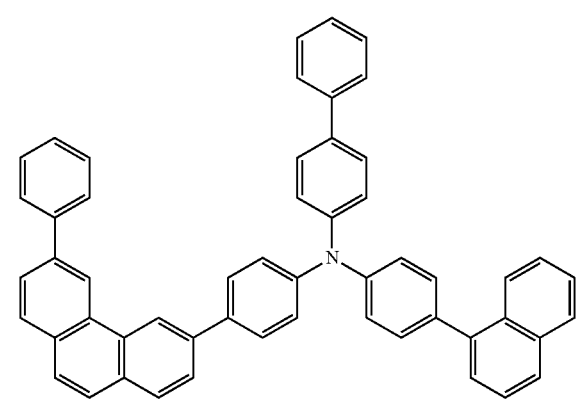
74
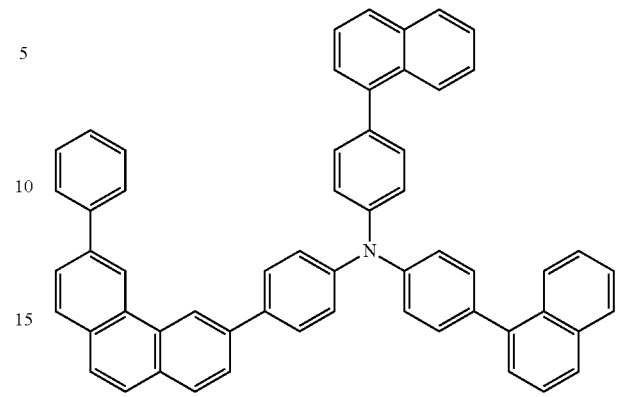
75
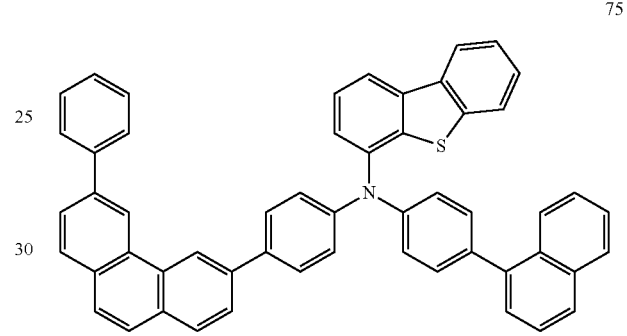
76
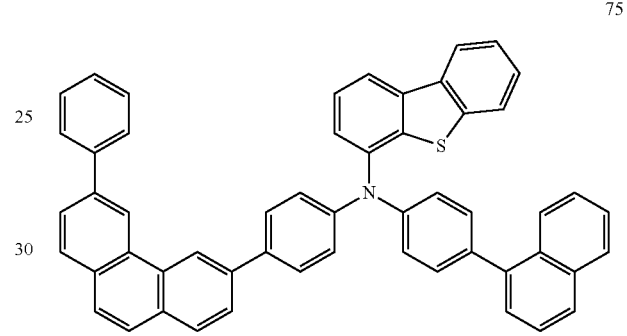
77
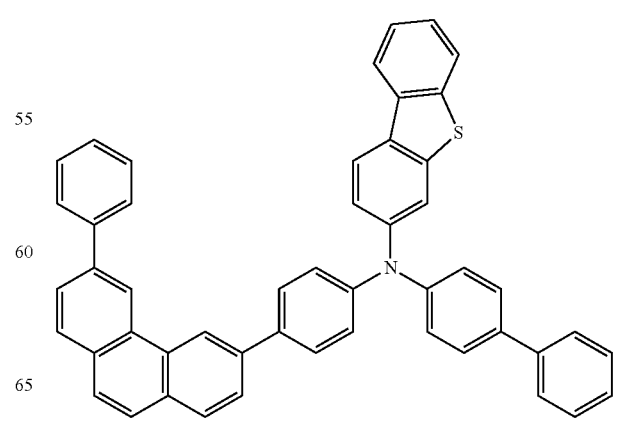

78
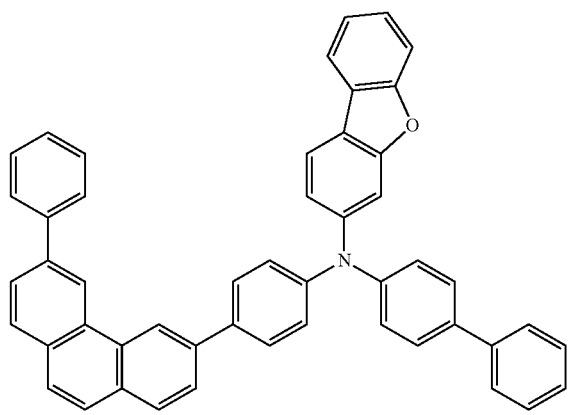
79
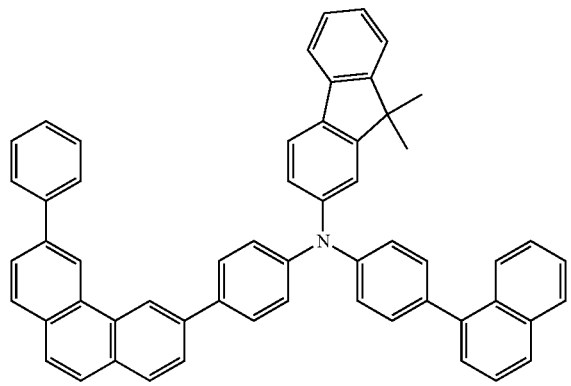
81
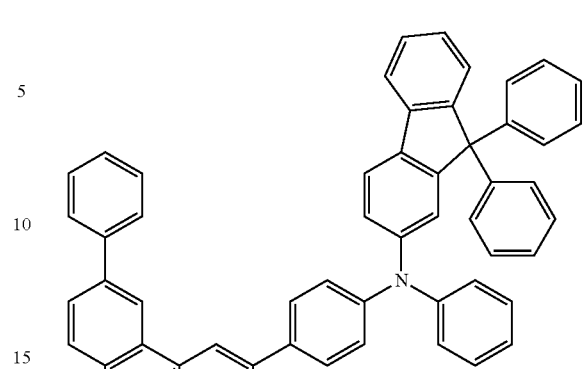
82
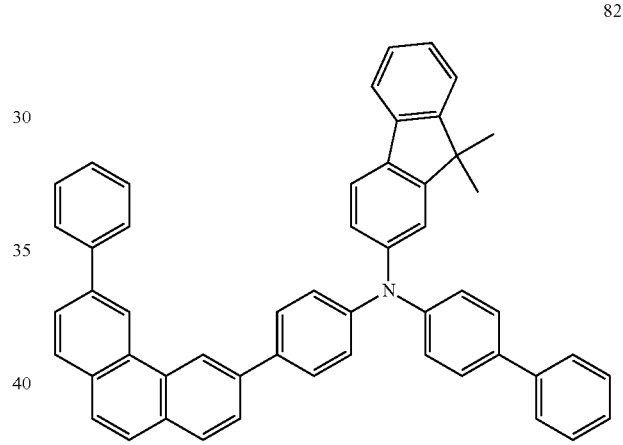
83
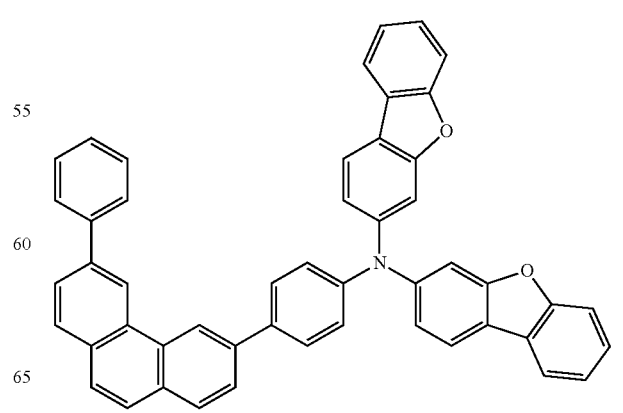

84
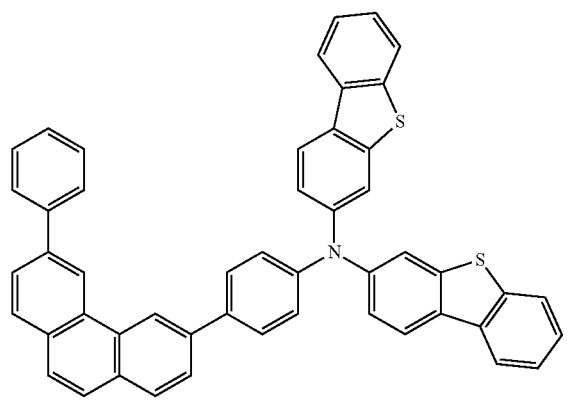
85
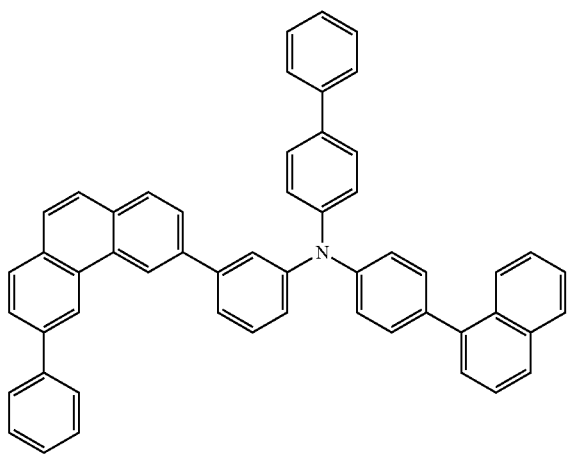
86
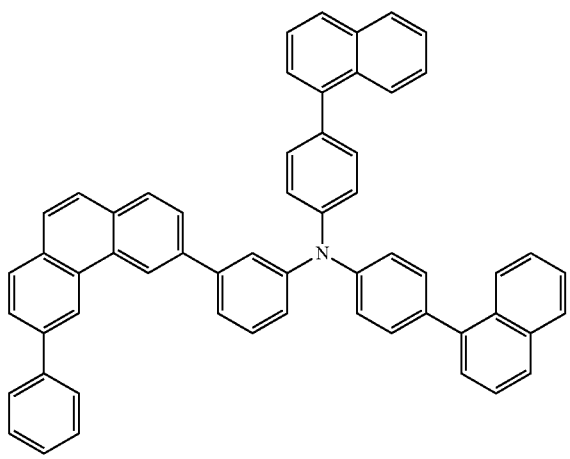
87
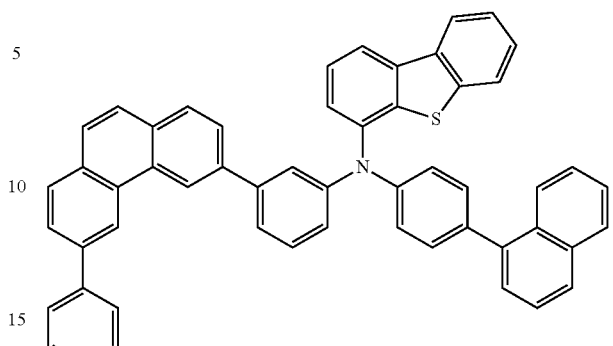
88
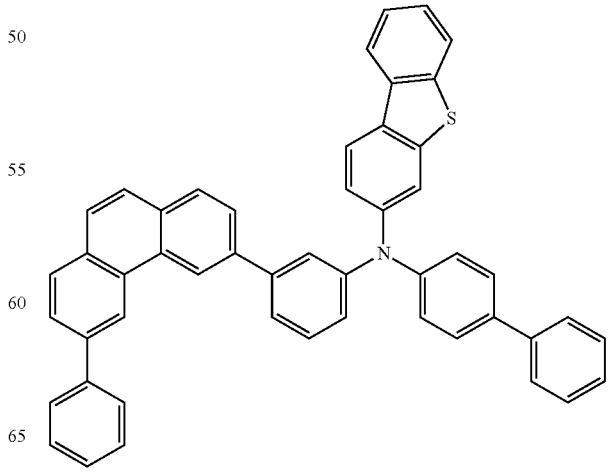
89

119
90
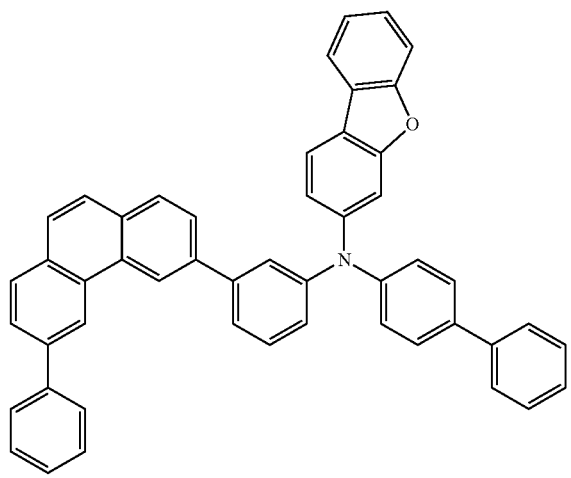
91
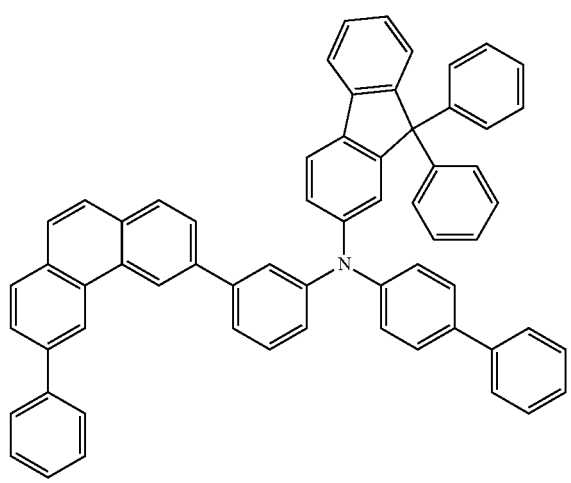
92
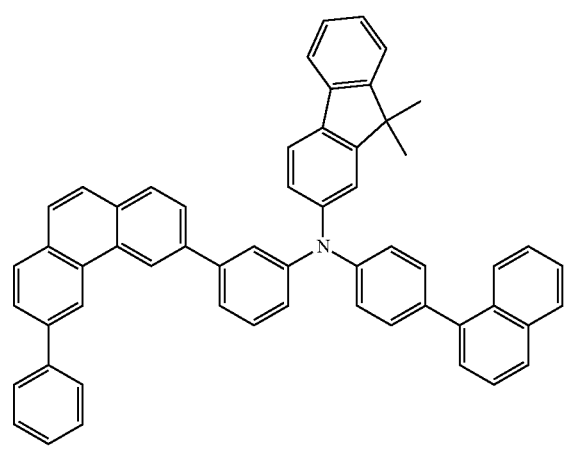
120
93
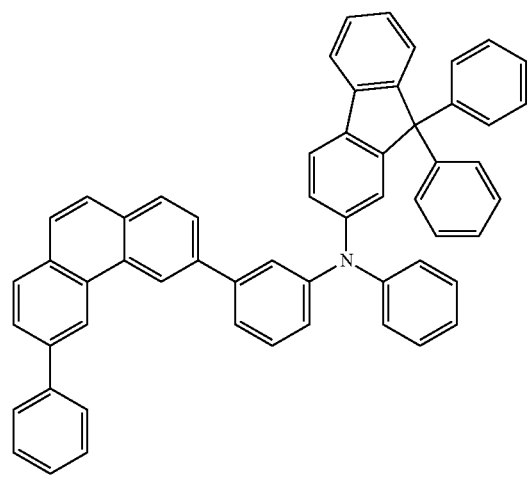
94
95
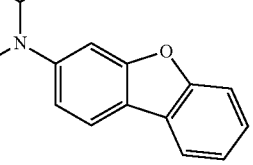

96
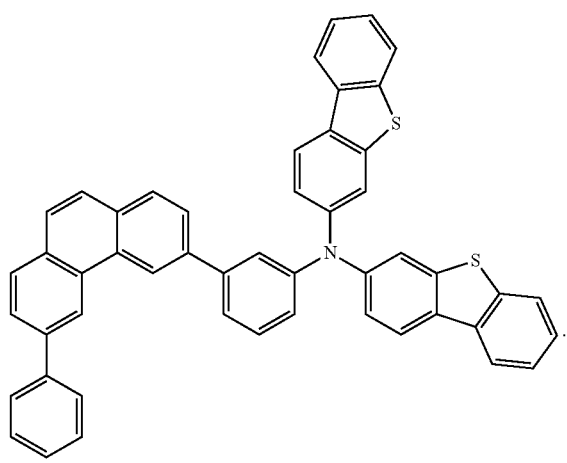
10. A monoamine compound consisting of at least one selected from compounds represented in the following Compound Group 1 and Compound Group 2:
[Compound Group 1]
1
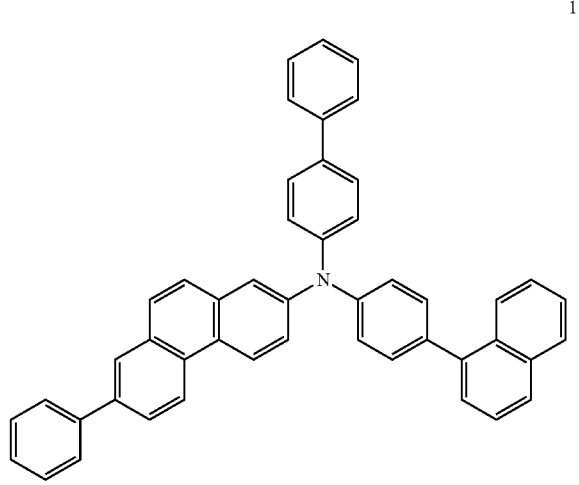
2
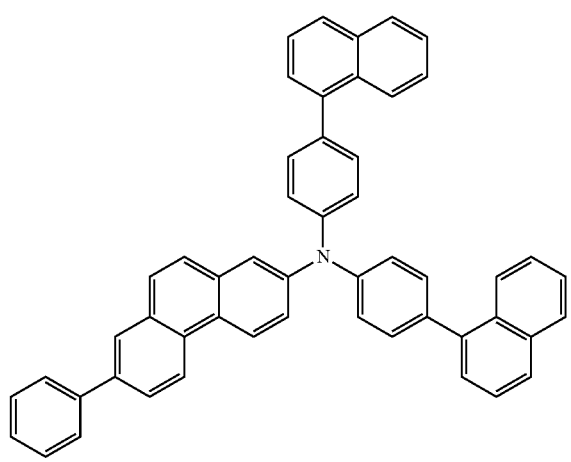
3
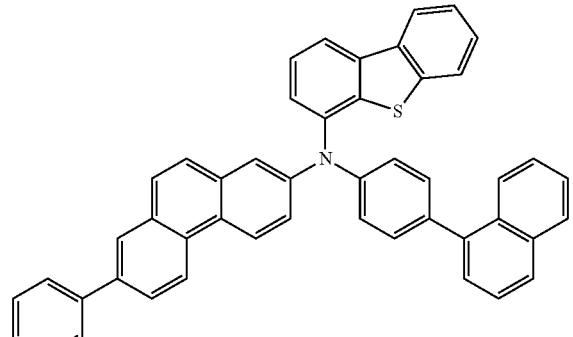
4
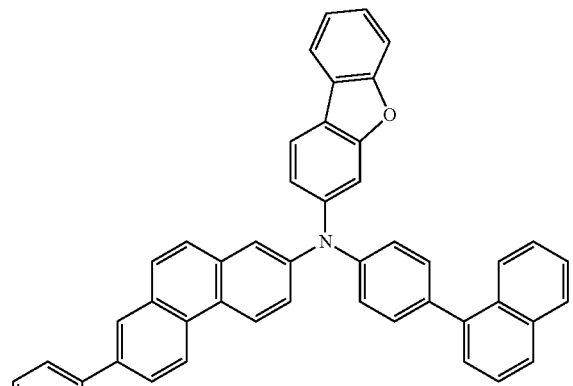
5
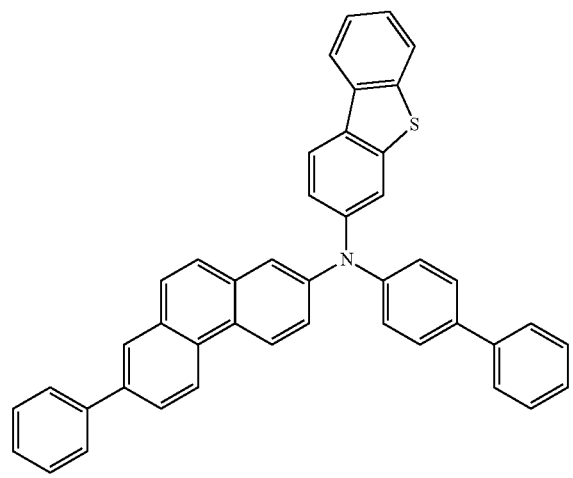

123
-continued
6
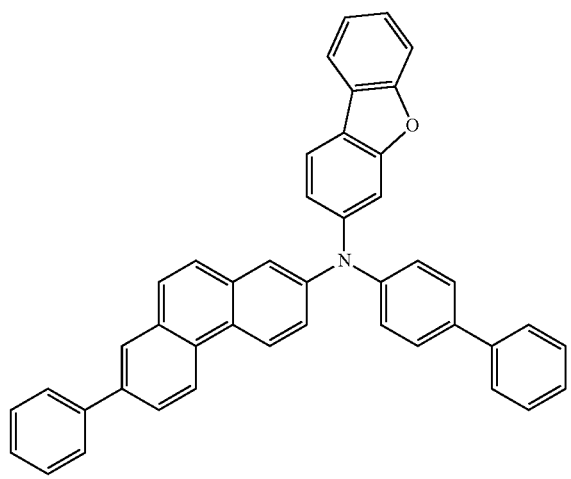
7
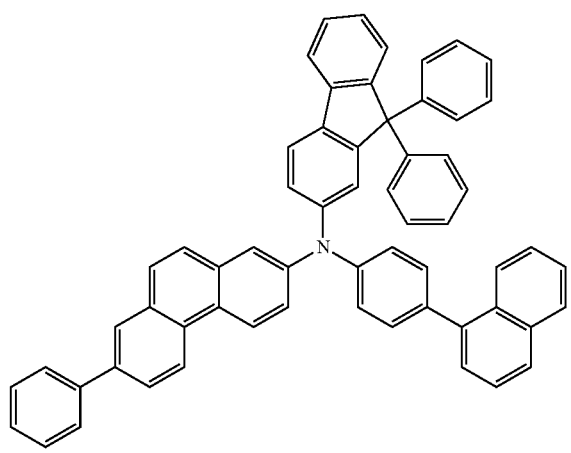
8
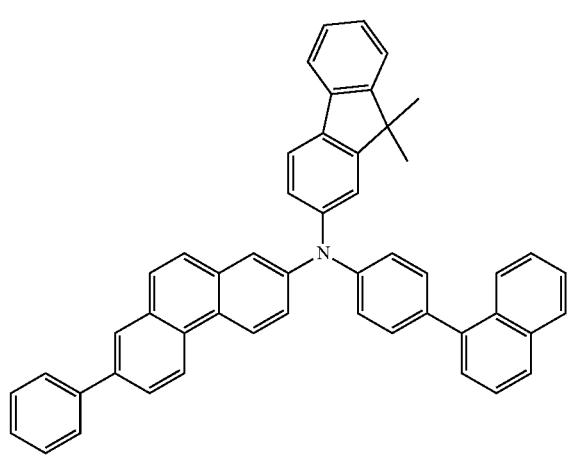
124
-continued
9
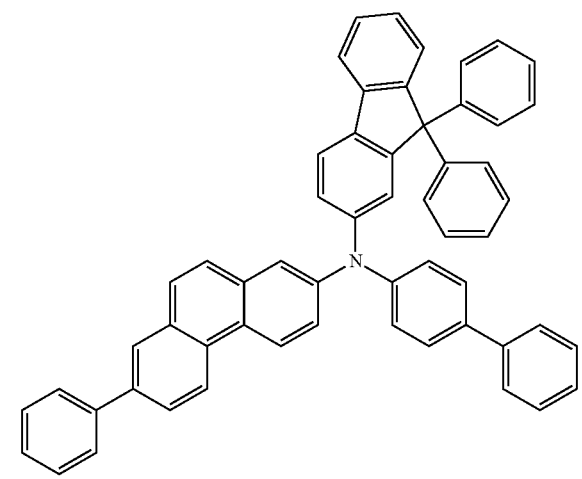
10
11

12
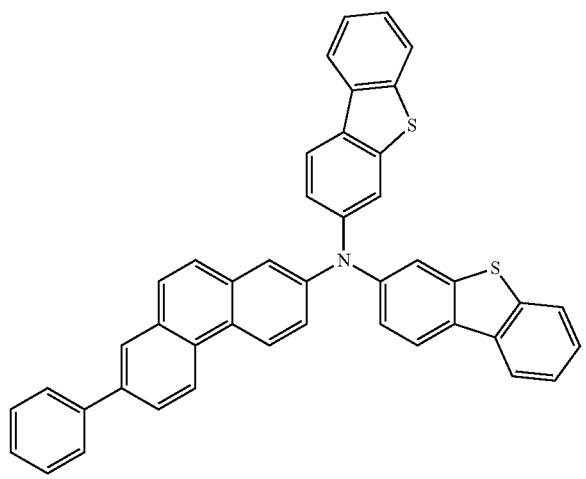
13
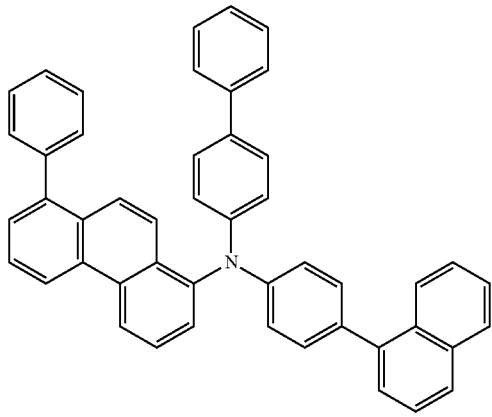
14
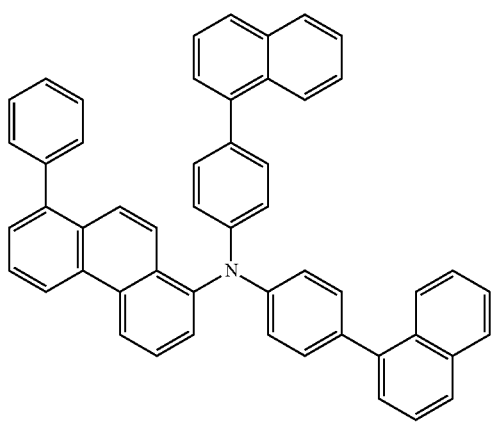
15
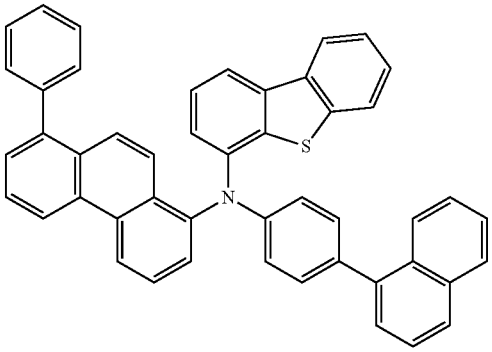
16
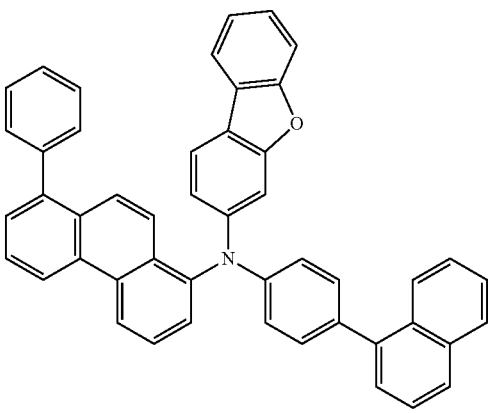
17
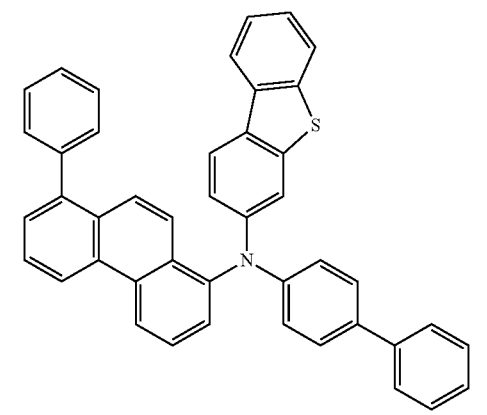
18
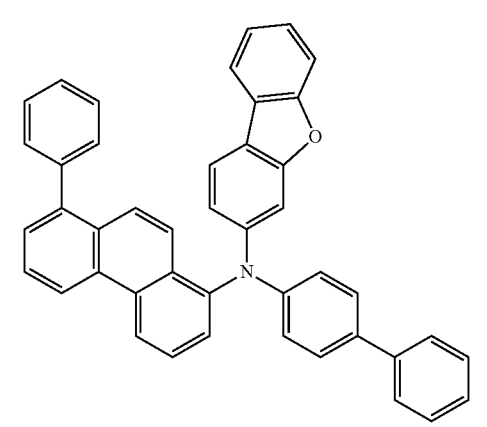

127
-continued
19
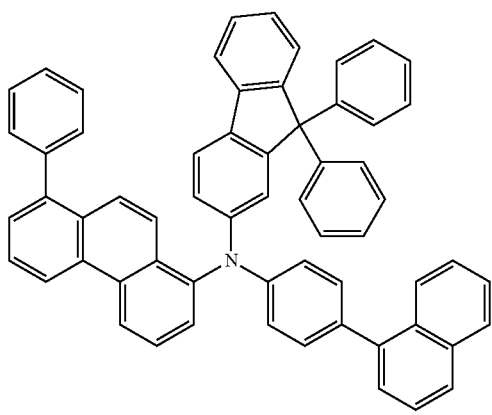
20
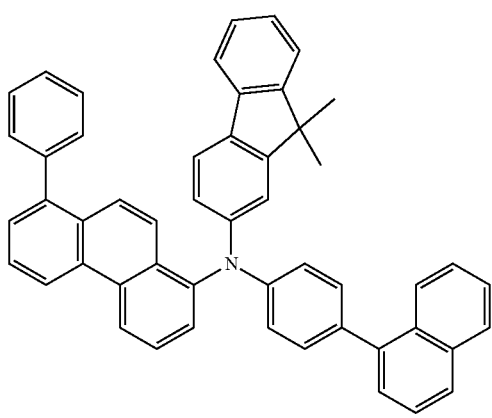
21
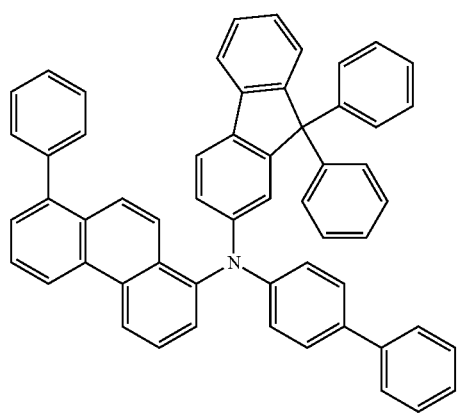
22
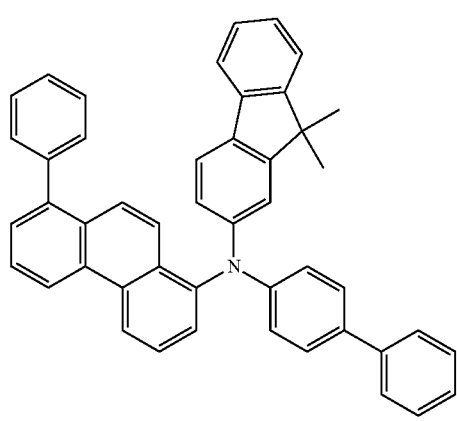
128
-continued
23
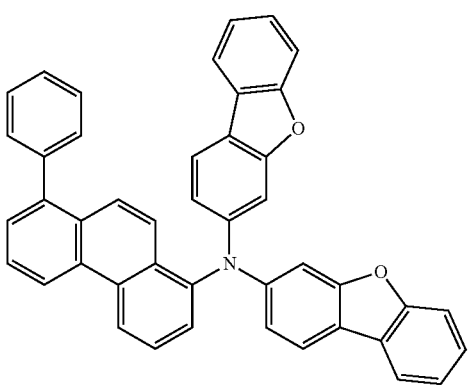
24
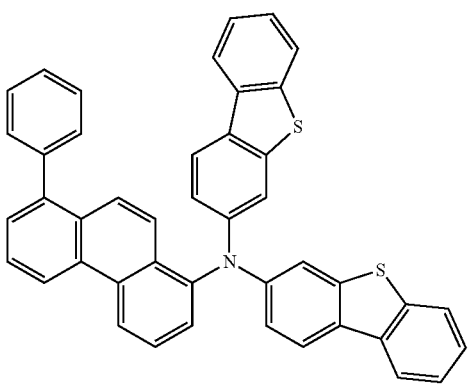
25
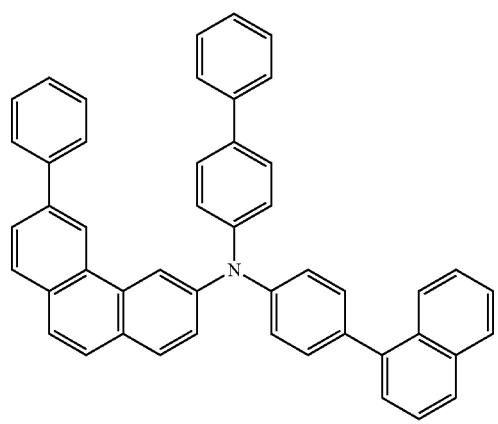
26
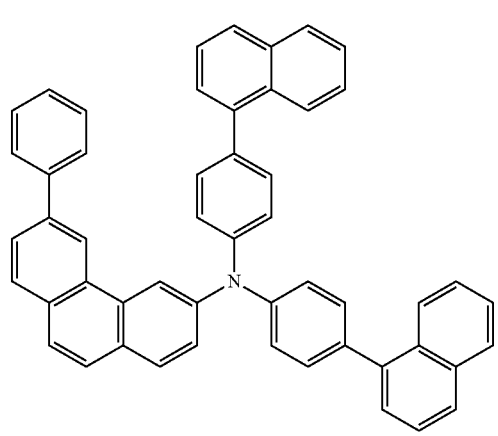

-continued
27
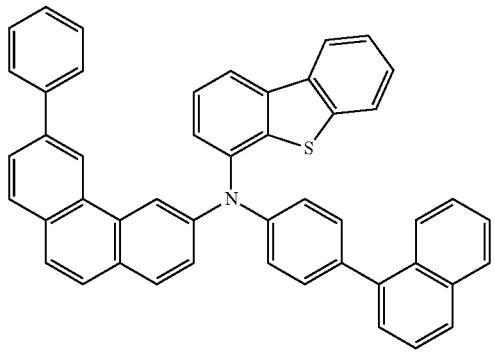
28
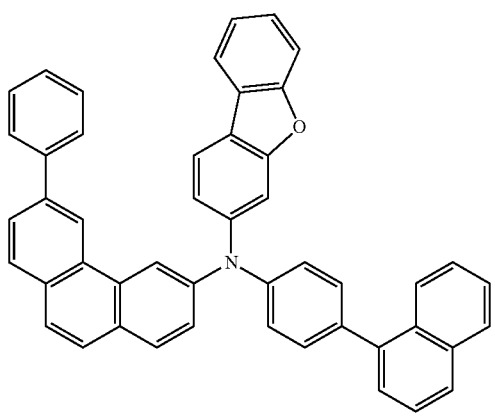
29
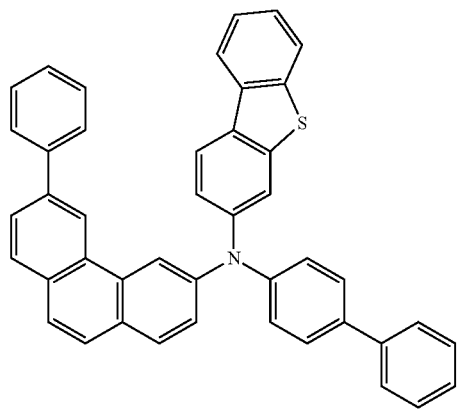
30
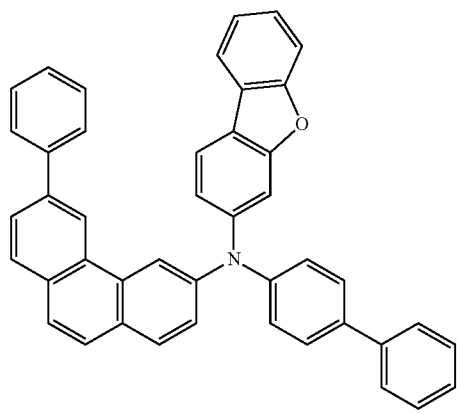
-continued
31
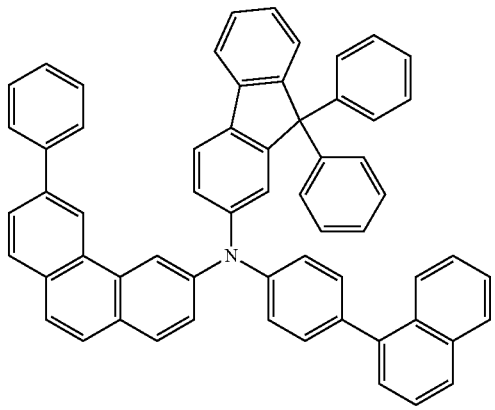
32
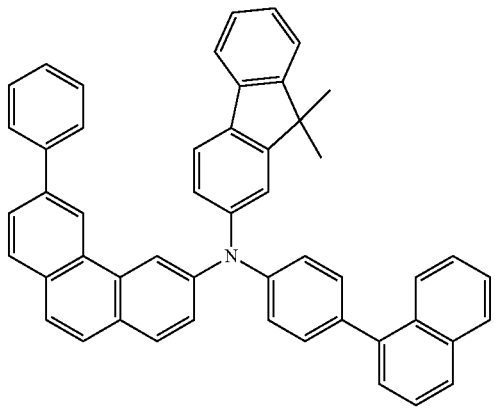
33
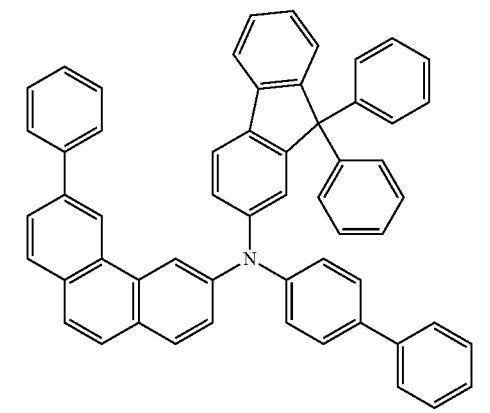
34
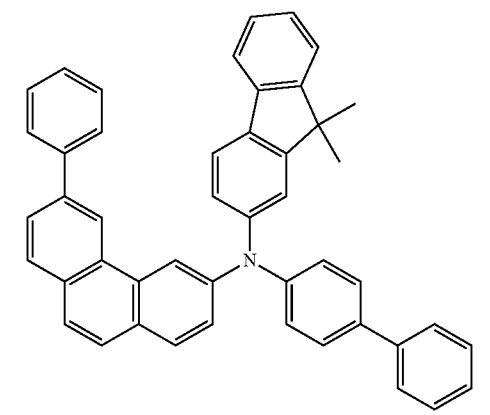

-continued
35
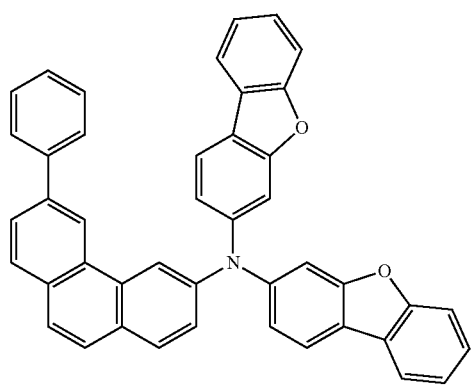
38
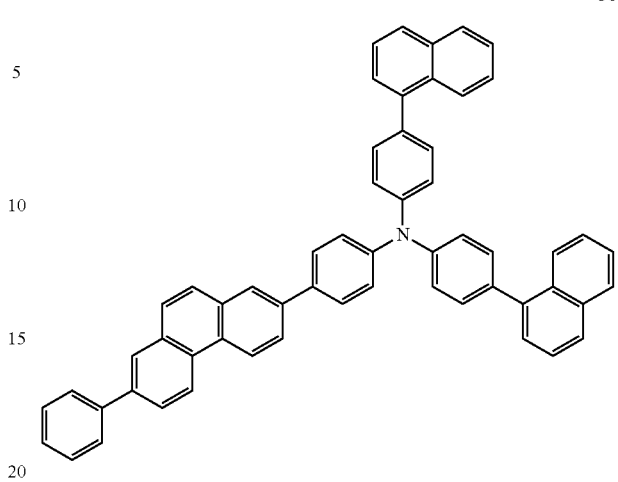
36
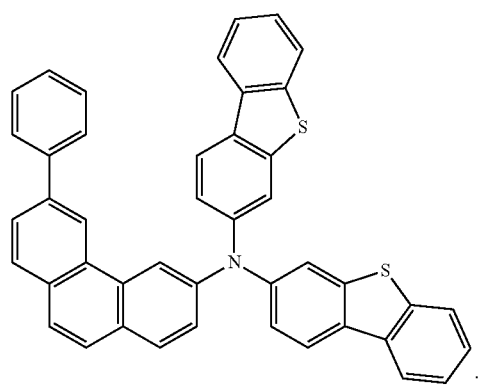
39
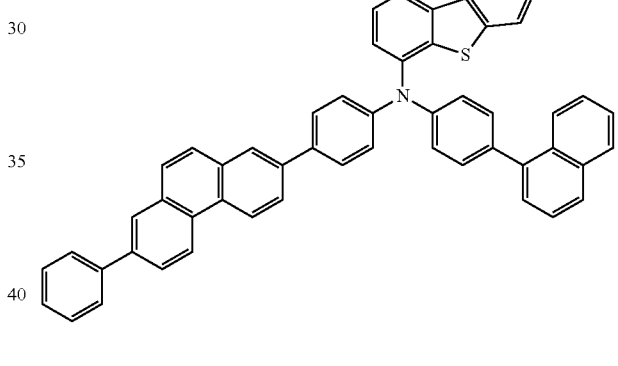
[Compound Group 2]
37
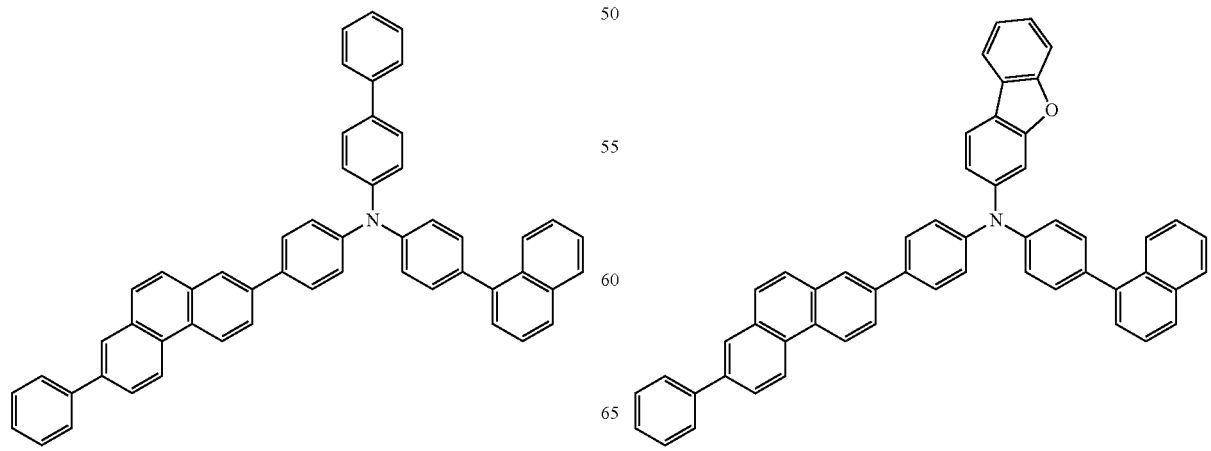
40
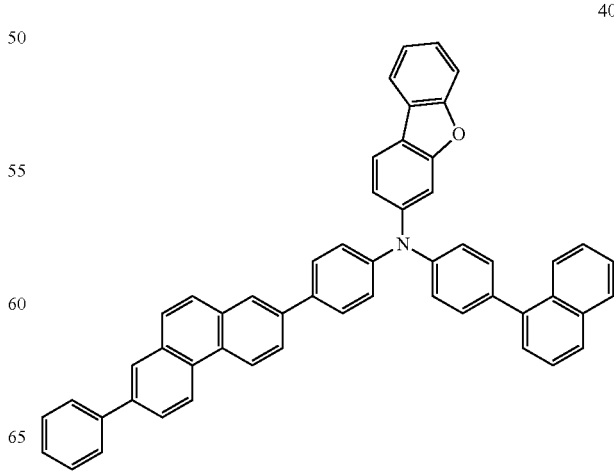

41
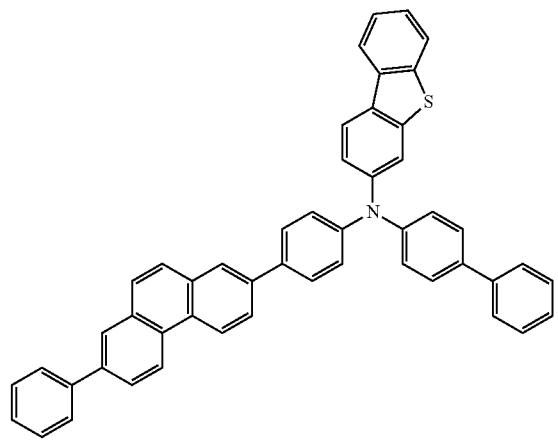
42
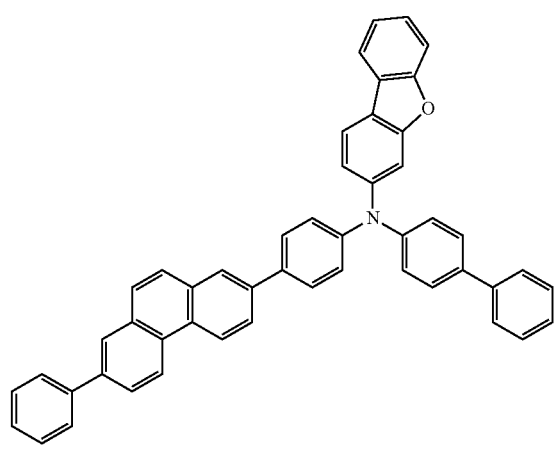
43
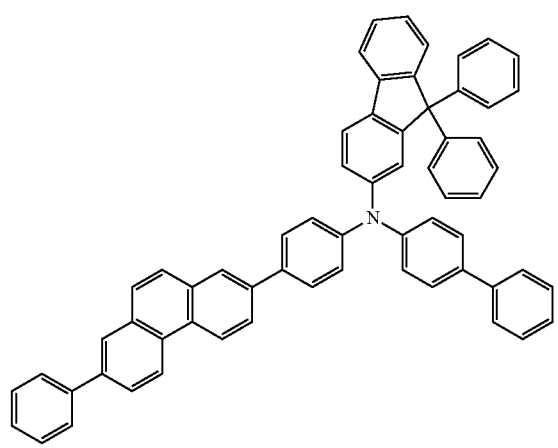
44
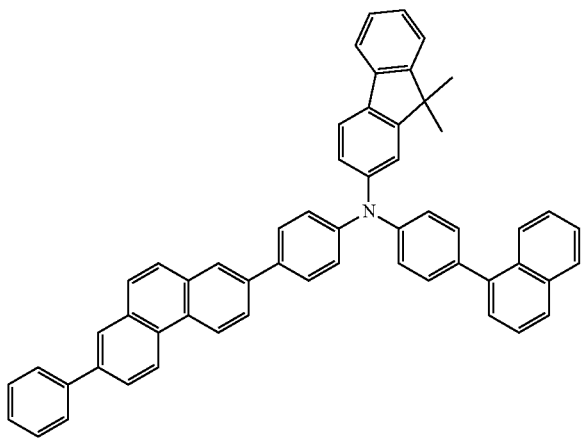
45
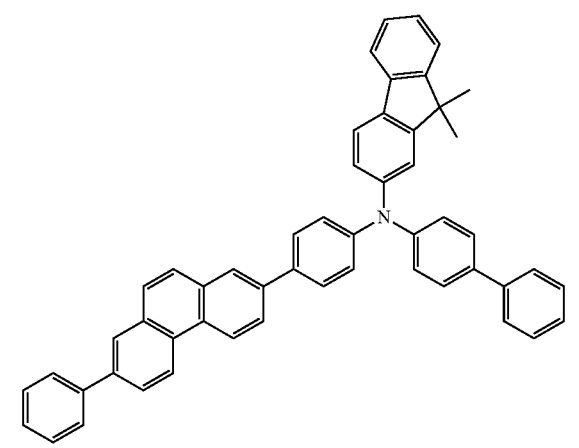
46

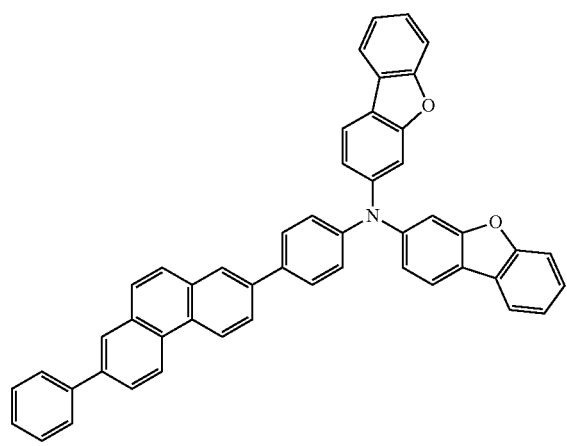
47
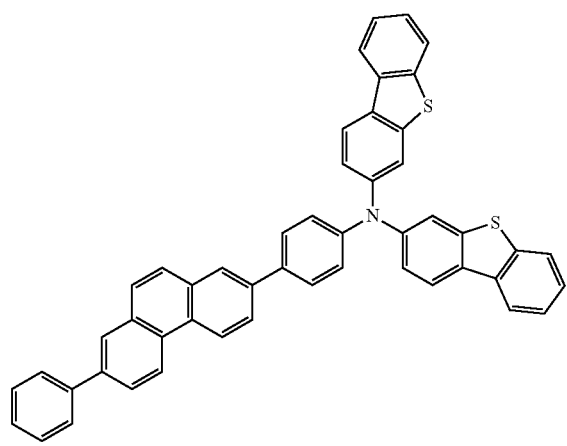
48
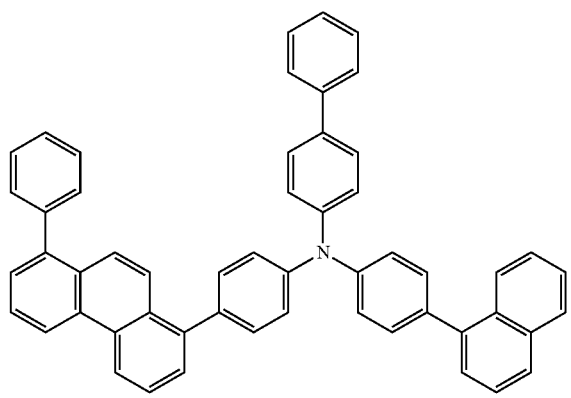
49
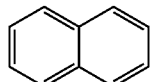
50
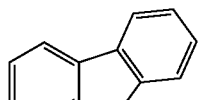
51
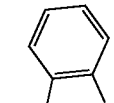
52
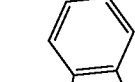
53

54
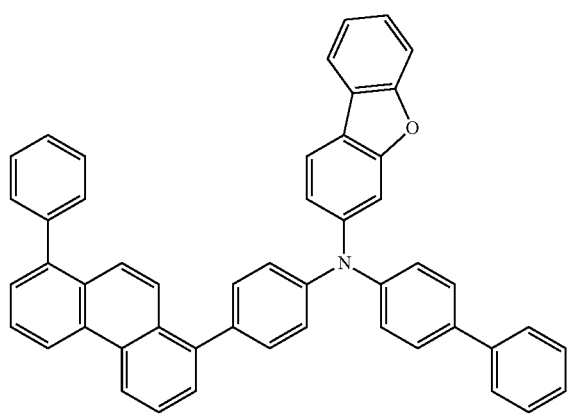
55
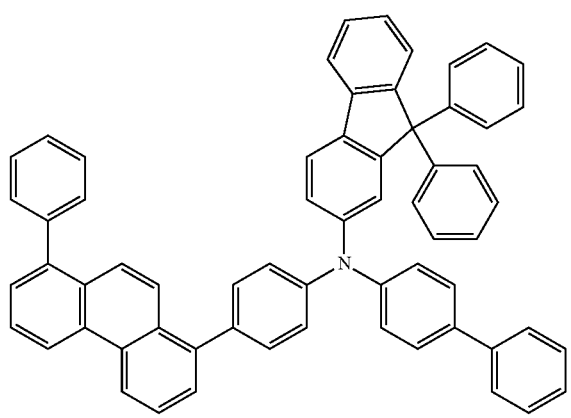
56
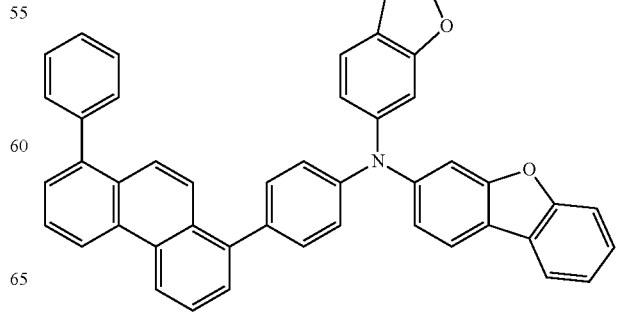
57
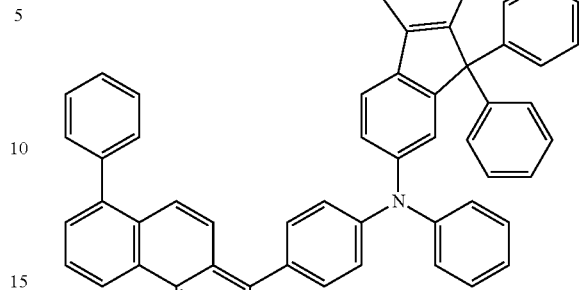
58
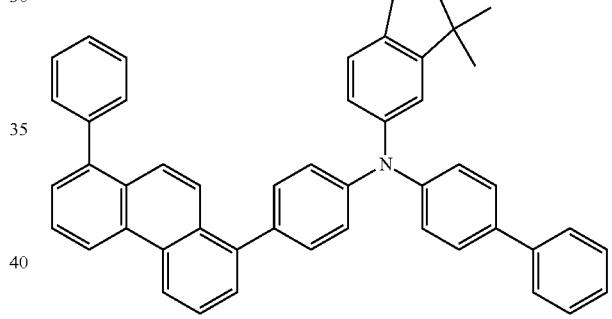
59

139
-continued
60
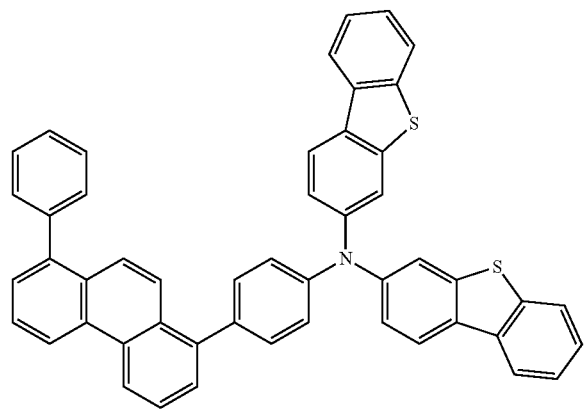
61
62
140
-continued
63
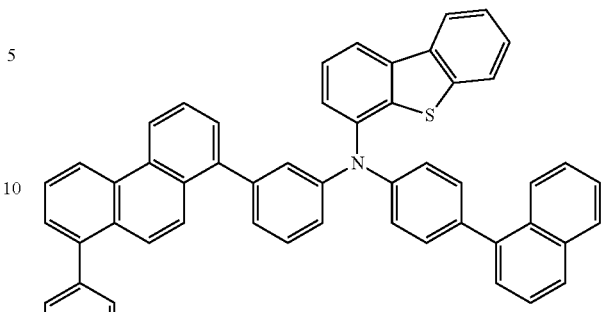
64
65
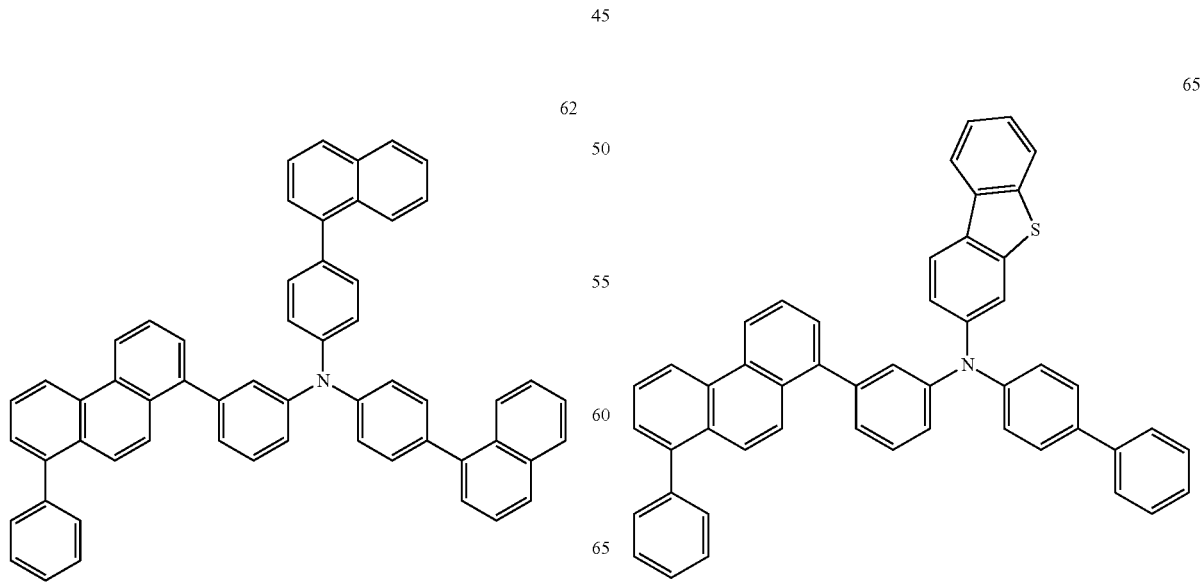

66
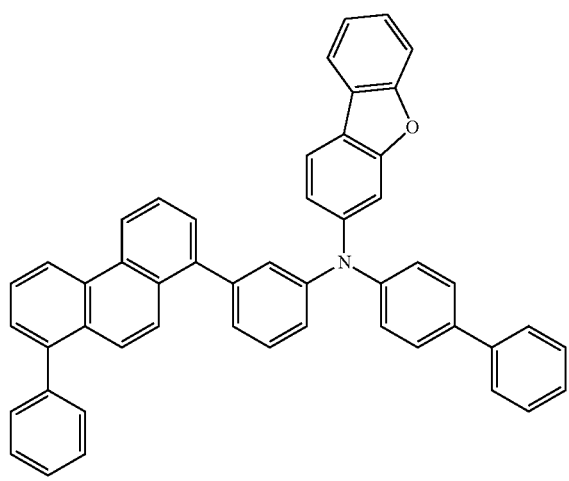
67
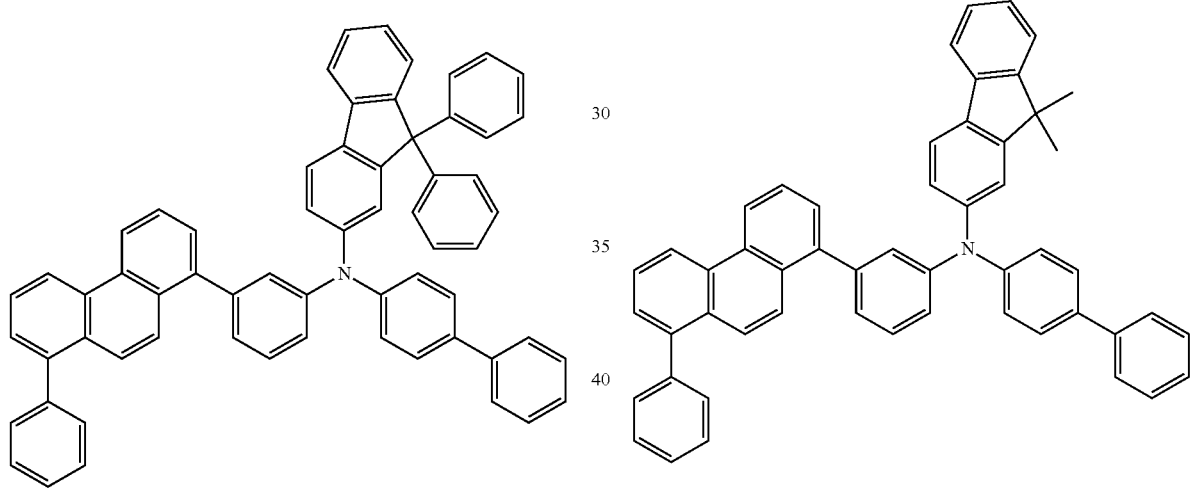
68
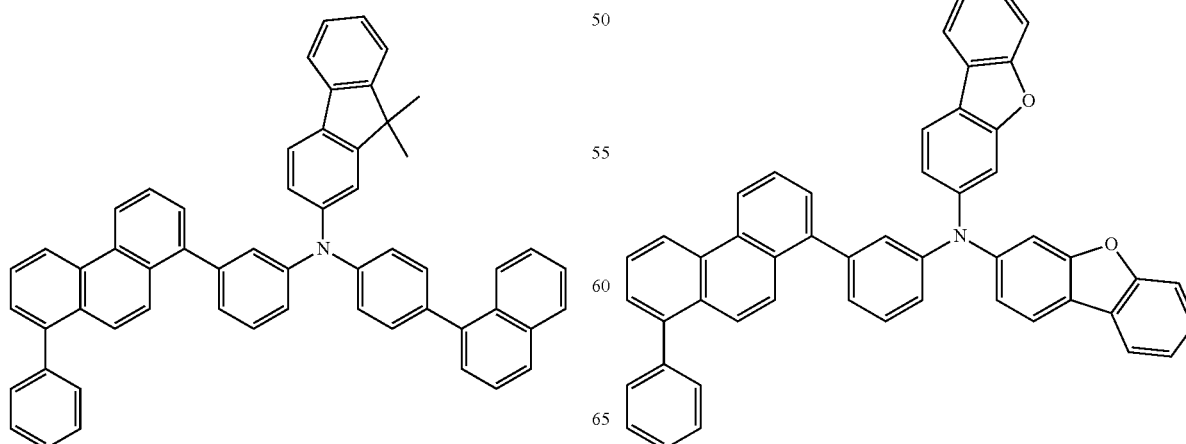
69
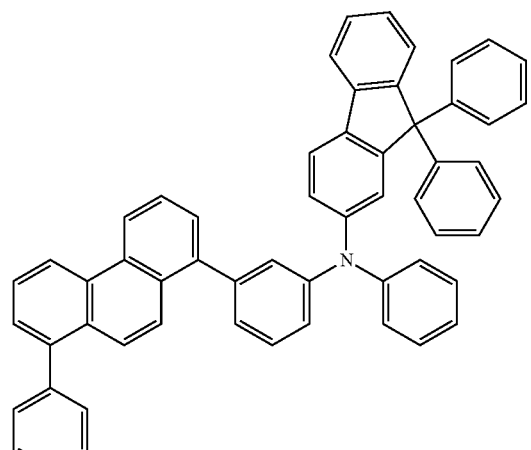
70
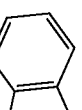
71
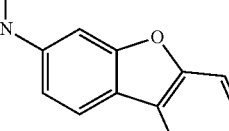

72
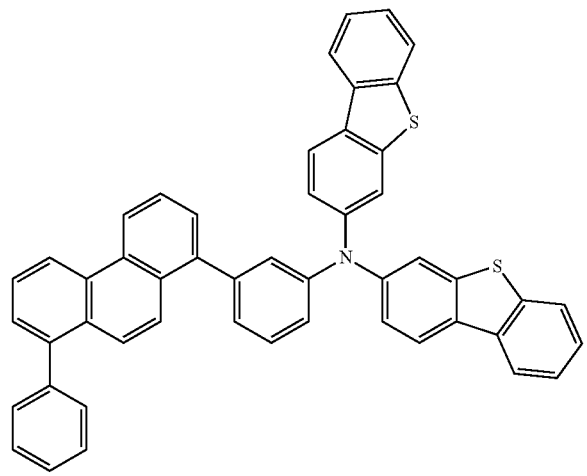
73
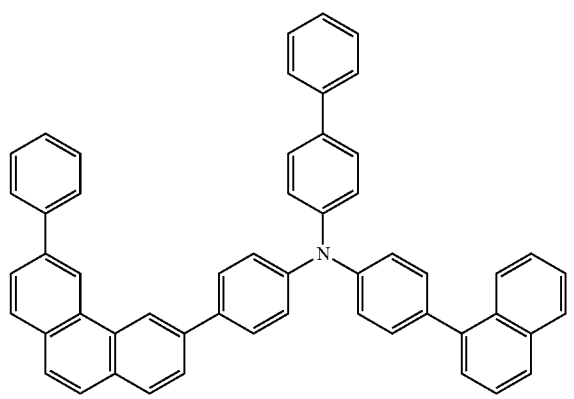
74
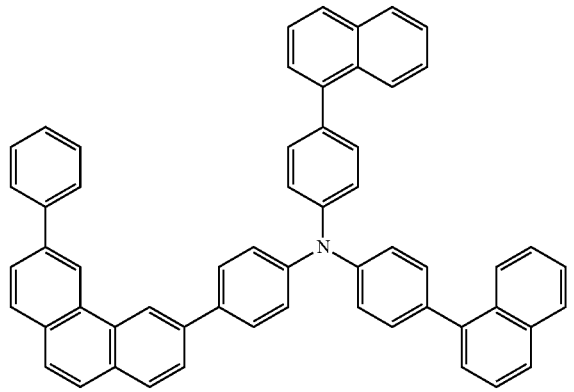
75
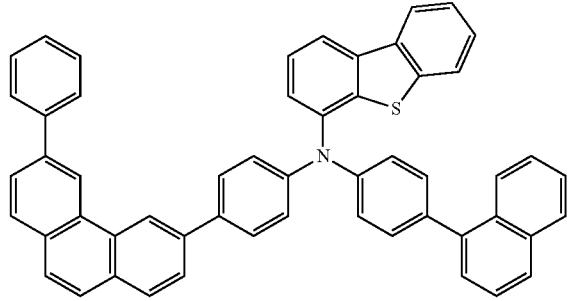
76
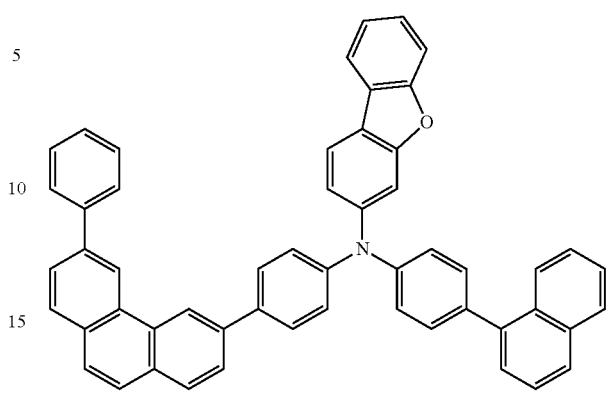
77
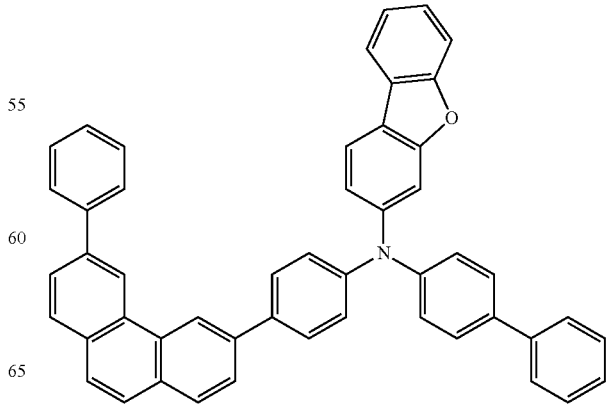
78

79
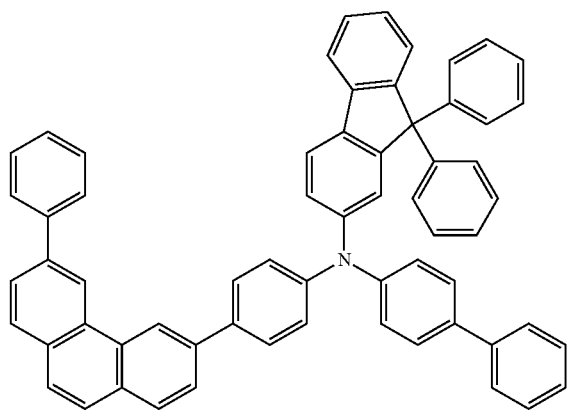
80
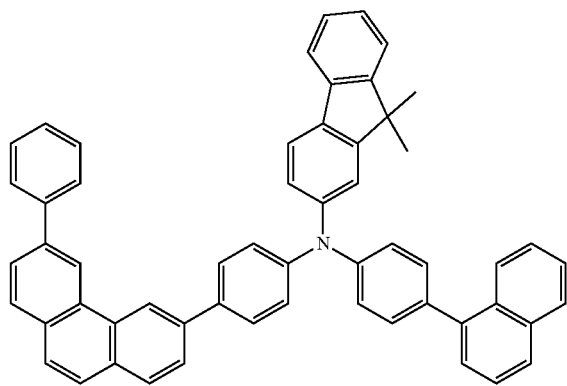
81
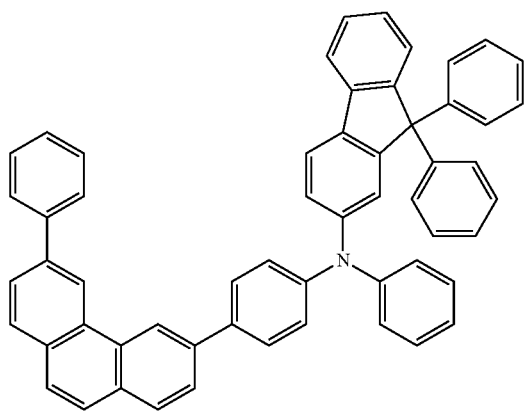
82
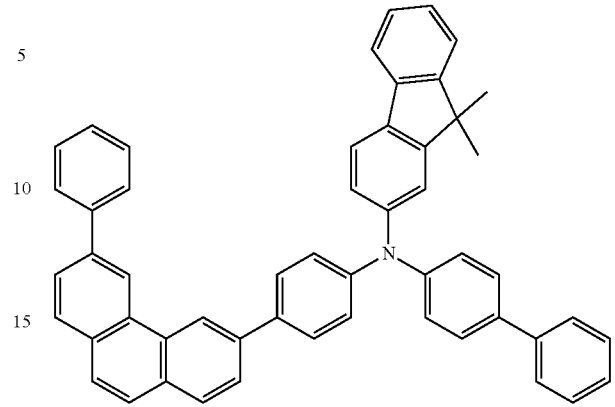
83
84
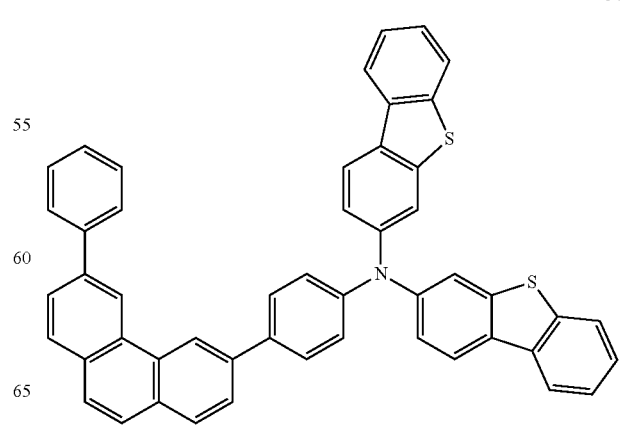

147
-continued

85

86

87

148
-continued

88

89

90

149
-continued
91
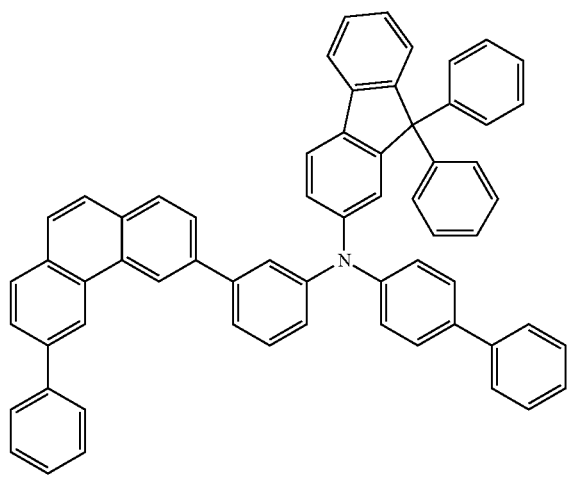
92
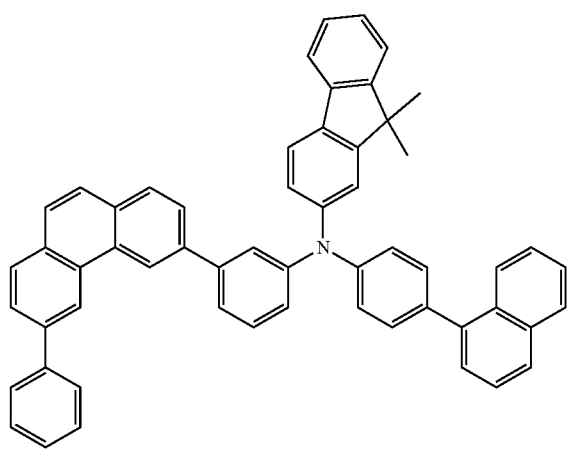
93
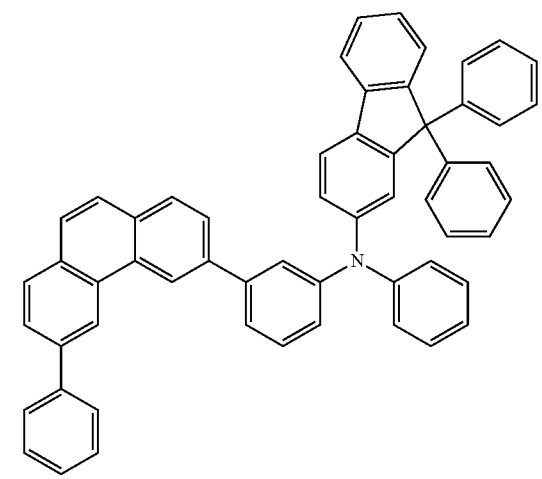
150
-continued
94
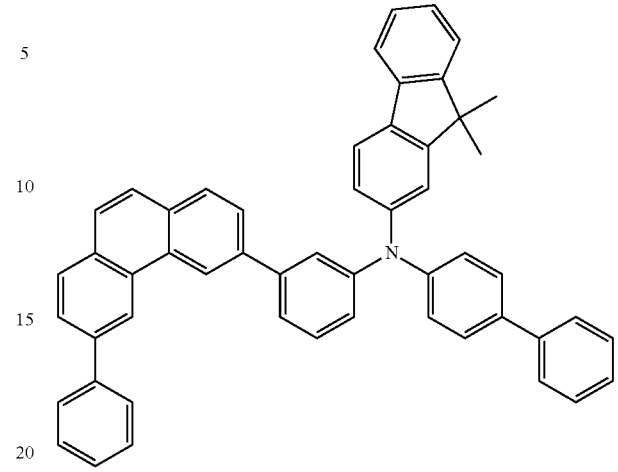
95
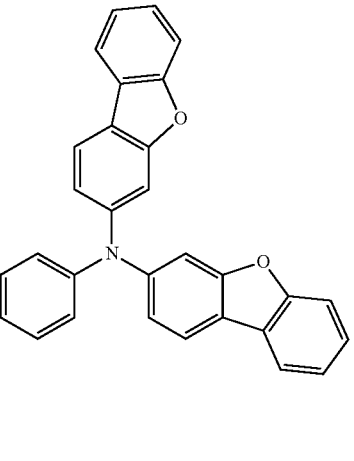
96
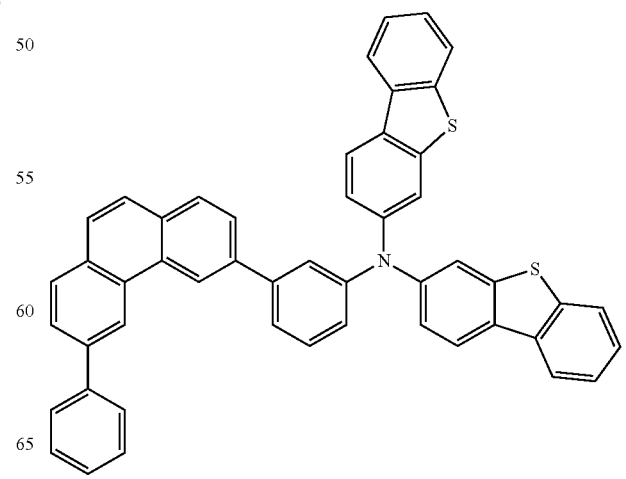

97
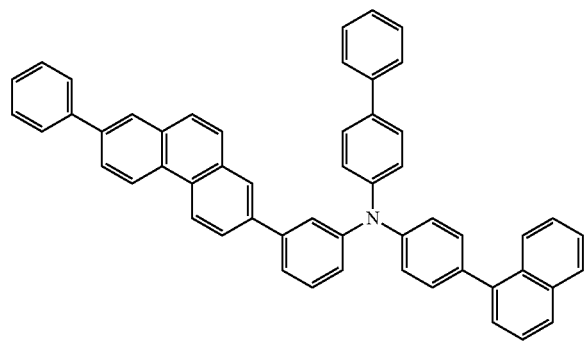
98
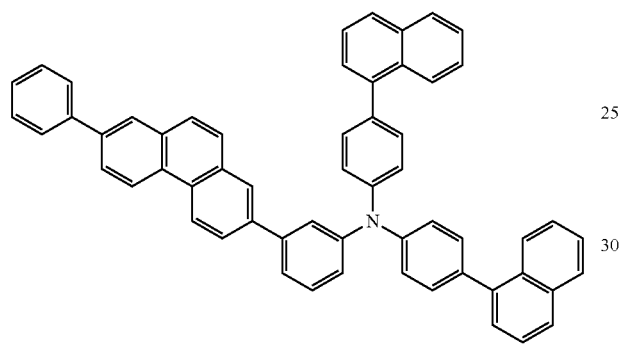
99
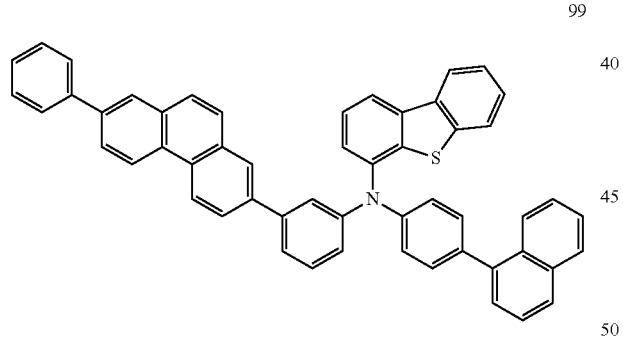
100
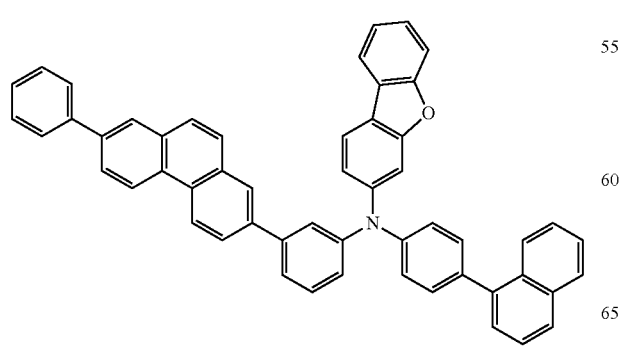
101
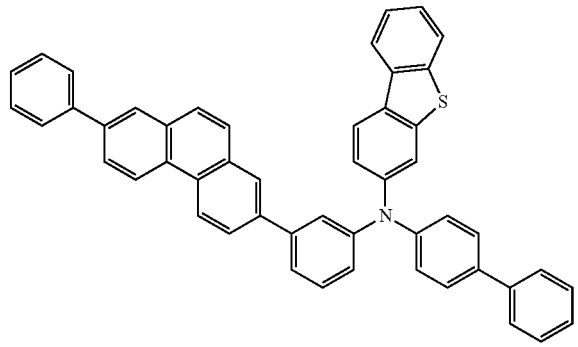
102
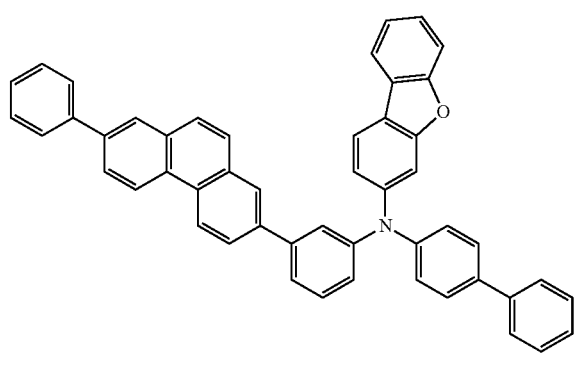
103
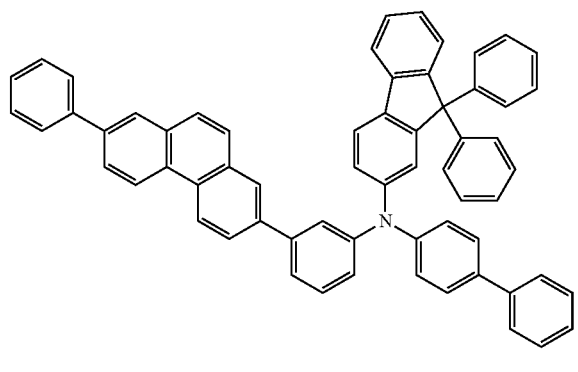
104
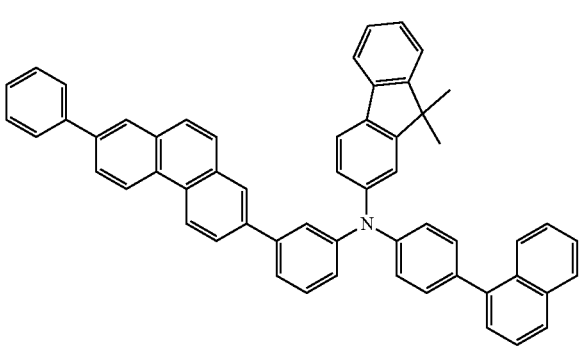

153
-continued
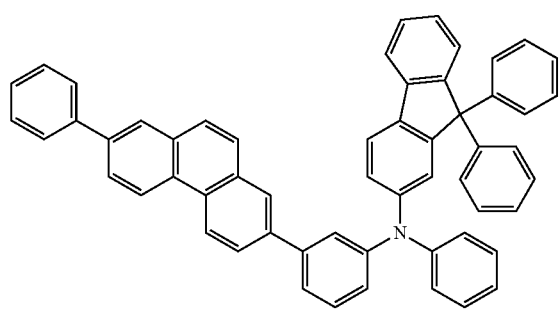
105
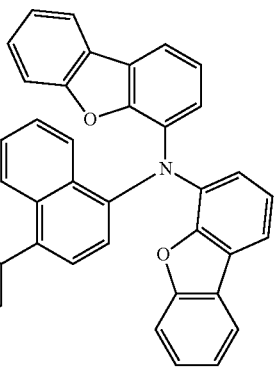
106
107
154
-continued
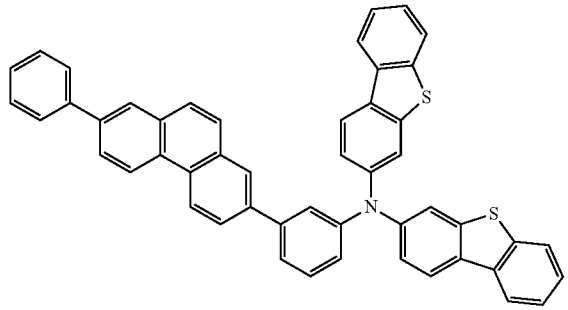
108
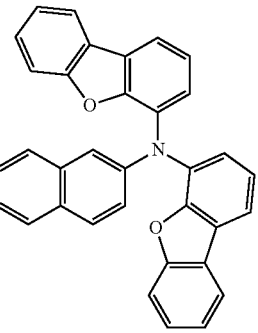
109
110
* * * * *

UNITED STATES PATENT AND TRADEMARK OFFICE
CERTIFICATE OF CORRECTION

PATENT NO. : 12,096,682 B2
APPLICATION NO. : 16/214132
DATED : September 17, 2024
INVENTOR(S) : Hideo Miyake et al.

It is certified that error appears in the above-identified patent and that said Letters Patent is hereby corrected as shown below:

In the Claims

In Column 75, Line 15, in Claim 1, delete "LiF/AI," and insert -- LiF/Al, --.

In Column 99, Line 46, in Claim 9, delete "1:" and insert -- 1 and Compound Group 2: --.

In Column 131, Lines 29-43, in Claim 10, Compound 36, delete

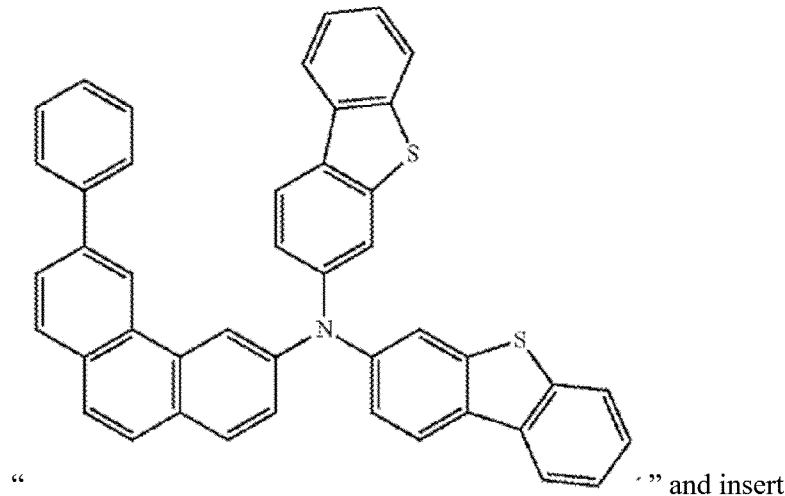

" " and insert

Signed and Sealed this
Fourth Day of February, 2025

Coke Morgan Stewart
*Acting Director of the United States Patent and Trademark Office*